(12) United States Patent
Sewalt et al.

(10) Patent No.: US 6,639,126 B1
(45) Date of Patent: Oct. 28, 2003

(54) PRODUCTION OF MODIFIED POLYSACCHARIDES

(75) Inventors: Vincent J. H. Sewalt, West Des Moines, IA (US); George W. Singletary, Ankeny, IA (US)

(73) Assignee: Pioneer Hi-Bred International, Inc., Des Moines, IA (US)

(*) Notice: Subject to any disclaimer, the term of this patent is extended or adjusted under 35 U.S.C. 154(b) by 0 days.

(21) Appl. No.: 09/731,166

(22) Filed: Dec. 6, 2000

Related U.S. Application Data

(60) Provisional application No. 60/169,993, filed on Dec. 6, 1999.

(51) Int. Cl.[7] .................. C12N 15/29; C12N 15/56; C12N 15/82; A01H 5/00; C12P 19/00
(52) U.S. Cl. ................ 800/284; 800/278; 800/286; 800/320.1; 800/263; 435/69.1; 435/101; 435/210; 435/320.1; 435/412; 435/419; 435/468
(58) Field of Search ................. 800/278, 284, 800/286, 320.1, 263; 435/69.1, 101, 210, 320.1, 419, 412, 468

(56) References Cited

U.S. PATENT DOCUMENTS

| | | |
|---|---|---|
| 4,734,364 A | 3/1988 | Line et al. |
| 5,378,830 A | 1/1995 | Yeh |
| 5,514,576 A | 5/1996 | Bower |
| 5,576,048 A | 11/1996 | Hauber et al. |
| 5,675,064 A | 10/1997 | Pearlstein et al. |
| 5,721,127 A | 2/1998 | Deweer et al. |
| 5,736,375 A | 4/1998 | Deweer et al. |
| 5,750,876 A | 5/1998 | Barry et al. |
| 5,824,790 A | 10/1998 | Keeling et al. |
| 5,849,090 A | 12/1998 | Haralampu et al. |
| 5,874,265 A | 2/1999 | Adams et al. |
| 5,879,509 A | 3/1999 | Sharyo et al. |

FOREIGN PATENT DOCUMENTS

| | | |
|---|---|---|
| WO | WO 91/19808 A1 | 12/1991 |
| WO | WO 98/50562 A1 | 11/1998 |
| WO | WO 00/11192 A3 | 3/2000 |

OTHER PUBLICATIONS

Kossmann et al. Progress Biotechnol. 10: 271–278, 1995.*
Kull et al. J. Genet. Breed. 49(1):69–76, Mar. 1995.*
Flipse et al. Planta 198(3):340–347, 1996.*
Beatty et al. Plant Physiology 119:255–266, 1999.*
Sulehuzzaman et al. Plant Mol. Biol. 23: 947–962, 1993.*
Anderson et al. (1990) "Enhancing Carbon Flow into Starch: the Role of ADPglucose Pyrophosphorylase" In: Vada, M.E., W.D. Parks (eds.) *Molecular and Cellular Biology of the Potato* (pp. 159–180). C.A.B. International, Wallingford, UK.
Ball et al. (1996) "From Glycogen to Amylopectin: A Model for the Biogenesis of the Plant Starch Granule" *Cell* 86:349–352.
Baulcombe (1983) "Wheat α–Amylase Genes: Cloning of a Developmentally Regulated Gene Family" *Genetic Engineering* 5:93–108.
Beatty et al. (1999) "Purification and Molecular Genetic Characterization of ZPU1, a Pullulanase–Type Starch–Debranching Enzyme from Maize" *Plant Physiol.* 119:255–266, No. 1.
Brink et al. (1984) "Maize Endosperm Mutants Affecting Soluble Carbohydrate Content as Potential Additives in Preparing Silage from Protein Forages" *Maydica* 29:265–286.
Fuwa et al. (1977) "Comparative Susceptibility to Amylases of Starches from Different Plant Species and Several Single Endosperm Mutants and Their Double–Mutant Combinations with Opaque–2 Inbred OH43 Maize" *Cereal Chem.* 54:230–237.
Fuwa et al. (1979) "Comparative Susceptibility of Starch Granules of Double– and Triple–Mutants Containing Amylose–Extender, Waxy, Sugary–1, Sugary–2, and Dull Genes of Maize Inbred OH43 (*Zea mays L.*) to Amylase" *J. Nutr. Sci. Vitaminol.* 25:103–114.
James et al. (1995) "Characterization of the Maize Gene Sugary1, a Determinant of Starch Composition in Kernels" *The Plant Cell* 7:417–429, No. 4.
Khursheed et al. (1988) "Barley α–Amylase Genes" *J. Biol. Chem.* 263(35):18953–18960.
Nakamura et al. (1996) "Some Properties of Starch Debranching Enzymes and Their Possible Role in Amylopectin Biosynthesis" *Plant Sci.* 121:1–18.
Nakamura et al. (1997) "Correlation between Activities of Starch Debranching Enzyme and Alpha–Polyglucan Structure in Endosperms of Sugary–1 Mutants of Rice" *Plant J.* 12:143–153.
Pan et al. (1984) "A Debranching Enzyme Deficiency in Endosperms of the Sugary–1 Mutants of Maize" *Plant Physiol.* 74:324–328.
Rahman et al. (1998) "Characterization of SU1 Isoamylase, a Determinant of Storage Starch Structure in Maize" *Plant Physiol.* 117:425–435.
Visser et al. (1989) "Molecular Cloning and Partial Characterization of the Gene for Granule–Bound Starch Synthase from a Wildtype and an Amylose–Free Potato (*Solanum tuberosum L.*)" *Plant Sci.* 64:185–192.

* cited by examiner

*Primary Examiner*—David T. Fox
(74) *Attorney, Agent, or Firm*—Alston & Bird LLP

(57) ABSTRACT

The invention alters the physical characteristics of storage polyglucans including starch. Methods are provided to modify the polyglucan biosynthesis pathway by simultaneously altering the activity of a pullulanase debranching enzyme and the activity of another polypeptide in the polyglucan biosynthesis pathway. Compositions of the invention include transgenic plants and seeds having a modified polyglucan structure and/or content and elevated phytoglycogen levels. Additional compositions include a grain with increased energy availability for improved feed quality and industrial uses. Further compositions include a polyglucan with improved functional properties useful in a wide range of food and industrial applications.

45 Claims, No Drawings

PRODUCTION OF MODIFIED POLYSACCHARIDES

CROSS-REFERENCE TO RELATED APPLICATIONS

This application claims the benefit of U.S. Provisional Application No. 60/169,993, filed on Dec. 6, 1999, herein incorporated by reference.

FIELD OF THE INVENTION

The invention relates to the production of modified polyglucans through the alteration of the polyglucan biosynthesis pathway.

BACKGROUND OF THE INVENTION

Starch constitutes 65–75% of the corn kernel and is the main source of energy for livestock and poultry fed corn-based feed rations. Energy availability from corn is limited to a certain degree by endosperm matrix factors that prevent the release of intact starch granules during digestion. Protein and fiber characteristics may be manipulated to facilitate the release of starch granules, thereby enhancing energy availability.

Energy availability from corn is also determined by starch and oil content, starch structure (amylose:amylopectin ratio), and interactions among these different factors. Degradation characteristics of isolated starch are largely determined by the polyglucan structure. Waxy starch (all amylopectin), once gelatinized, is more rapidly digested than normal starch (70–75% amylopectin, 25–30% amylose). High amylose (70%) starch is more slowly and less expensively digested. Highly branched polysaccharides such as phytoglycogen are soluble and very rapidly digested. The enhanced in vitro digestibility of isolated starch from waxy corn over isolated starch from normal corn does not always translate to improved digestibility of ground corn (e.g., Ertl and Dale (1997) *Appl. Poul. Res.* 6:432–435), which is possibly caused by component interactions.

Starch can be converted into simple sugars by an enzymatic process carried out in two stages: the liquefaction of starch and the saccharification of the liquefied starch. See, for example, Manners (1985) "Structural Analysis of Starch Components by Debranching Enzymes," in *New Approaches to Research on Cereal Carbohydrates*, ed. Hill (Amsterdam), pp. 45–54; and Enevoldsen (1985) "Aspects of the Fine Structure of Starch", in *New Approaches to Research on Cereal Carbohydrates*, ed. Hill (Amsterdam), pp. 55–60.

Amylopectin is a branched glucose polymer that is a major constituent of plant starch granules and the primary determinant of their structural and physical properties. The spatial positioning of α(1→6) glycosidic bonds, i.e., branch linkages, is a critical aspect of the three dimensional structure of amylopectin. Branch linkages are introduced by the actions of starch branching enzymes (BEs) and are hydrolyzed by the, actions of starch debranching enzymes (DBEs). See, for example, Preiss (1996) *Starch Synthesis in Sinks and Sources* (Marcell Dekker, Inc., New York), pp. 63–96; Smith et al. (1997) *Annu. Rev. Plant Physiol. Plant Mol. Biol.* 48:67–87. Mutations that result in DBE deficiencies, such as the sugary1 (su1) mutations of maize and rice (James et al. (1995) *Plant Cell* 7:417–429; Nakamura et al. (1996) *Physiol. Plant.* 97:491–498; Pan et al. (1984) *Plant Physiol.* 74:324–328; Rahman et al. (1998) *Plant Physiol.* 117:425–435), alter the number and spatial distribution of branches in amylopectin. DBEs, therefore, are believed to be involved in branch pattern determination, possibly providing an editing function (Ball. et al. (1996) *Cell* 86:349–352).

The two classes of DBEs that have been identified in plants and are distinguishable by their substrate specificity (Doehlert et al. (1991) *J. Plant Physiol.* 138:566–572; Lee et al. (1971) *Arc. Biochem. Biophys.* 143:365–374; and Lee et al. (1971) "Glycogen and Starch Debranching Enzymes," *The Enzymes*, Vol. 3, ed. Boyer (Academic Press, New York), pp. 191–234. Isoamylases cleave α(1→6) branch linkages in amylopectin and glycogen but do not hydrolyze the chemically identical bonds in pullulan, an α(1→6)-linked maltotriose polymer. In contrast, pullulanases, also referred to as R-enzymes or limit-dextrinases (Manners (1997) *J. Appl. Glycosci.* 44:83–85), readily hydrolyze α(1→6) linkages of pullulan or amylopectin, but have little activity toward glycogen. Biochemical fractionation experiments identified both isoamylase and pullulanase activities in developing maize kernels during the starch biosynthetic period (Doehlert et al. (1991) *J. Plant Physiol.* 138:566–572; Pan et al. (1984) *Plant Physiol.* 74:324–328), but the specific functions of these two DBEs in polyglucan biosynthesis have not yet been established.

The primary sequences of a pullulanase from rice and maize endosperm are known from cloned cDNAs. Rice R-enzyme (RE) was purified biochemically and characterized as a pullulanase-type DBE, and the cDNA coding for RE was cloned (Nakamura et al. (1996) *Planta* 199:209–218; Toguri (1991) *J. Plant Physiol.* 137:541–546). A maize pullulanase, ZPU1, has also been cloned (Beatty et al. (1999) *Plant Physiol.* 119:255–266). In addition, a maize cDNA identified from a cloned fragment of the su1 gene codes for a protein similar to bacterial isoamylases (James et al. (1995) *Plant Cell* 7:417–429). The su1 gene product, SU1, functions as an isoarnylase-type DBE and is present in developing maize endosperm during the time that starch is synthesized (Rahman et al. (1998) *Plant Physiol.* 117:425–435).

Expression of the isoamylase- and pullulanase-type DBEs of maize seemingly is coordinately controlled. Even though the su1 gene codes for an isoamylase (Rahman et al. (1998) *Plant Physiol.* 117:425–435), previous studies have demonstrated a reduction in the activity of a pullulanase-type DBE in su1—mutant endosperms. (Pan et al. (1984) *Plant Physiol.* 74:324–328). Consistent with these data, a protein related immunologically to rice RE is present in nonmutant maize kernels at 20 days after pollination (DAP) but deficient in su1—mutant kernels of the same age (Rahman et al. (1998) *Plant Physiol.* 117:425–435). Thus, su1—mutations apparently result in the deficiency of two distinct DBEs. In rice, the su1 mutation controlling RE expression maps to a chromosomal location that is distinct from the gene that codes for RE (Nakamura et al. (1996) *Planta* 199:209–218). Accordingly, coordinated control of the amount of isoamylase and pullulanase protein (and activity) is seemingly operative in rice as well (Kubo et al. (1999) *Plant Physiol.* 121:399–409).

Mutations in su1 increase phytoglycogen content and produce several advantageous physical characteristics of polyglucan. For example, the accumulation of phytoglycogen in su1 mutants is associated with smaller and more numerous starch granules. In addition, a polyglucan containing a high phytoglycogen content has a reduced temperature of gelatinization compared to that of waxy or normal starch (Wang et al. (1992) *Cereal Chem.* 69:328–334). The reduced gelatinization temperature increases starch solubility after processing (grinding, pelleting, steam flaking) at temperatures below the gelatinization temperature of normal starch. The smaller granule size and reduced temperature of gelatinization may both contribute to the high digestibility of starch from sugary1 mutant corn. See, for example, Fuwa et al. (1979) *J. Nutr. Sci. Vitaminol.* 25:103–114 and Fuwa et al. (1979) *Cereal Chem* 54:230–237.

The relative importance of SU1 and ZPU1 in polyglucan debranching and the production of phytoglycogen is unclear, since protein levels and debranching activities of both enzymes are reduced in the su1 mutant. However, in rice the su1 mutation is primarily associated with a reduction in pullulanase activity and the reduction in the ratio of debranching to branching enzyme activities (Nakamura et al. (1997) *Plant J.* 12:143–153). This phenotype suggests that the reduction in pullulanase activity is important to the rice su1 phenotype (Kubo et al. (1999) *Plant Physiol.* 121:399–409).

The present invention combines the altered expression of a pullulanase debranching enzyme, preferably with various other alterations in the polyglucan biosynthesis pathway, to produce modified polyglucan having optimized energy availability for different classes of livestock and optimized adduct modification of glucan production for food and industrial use.

SUMMARY OF INVENTION

Methods and compositions are provided to modify the physical characteristics of polyglucan. In particular, the methods of the invention provide a method for modulating polyglucan biosynthesis in a plant or plant cell. The method comprises stably introducing into the genome of the plant or plant cell at least two DNA constructs. The first DNA construct comprises a nucleotide sequence operably linked to a promoter active in the plant. Expression of the nucleic molecule decreases pullulanase-type activity in the plant. The nucleotide sequence of the first DNA construct can further comprise: a nucleic acid molecule comprising a nucleotide sequence encoding a plant pullulanase-type polypeptide or fragment thereof; a nucleic acid molecule comprising a nucleic acid sequence of SEQ ID NO:1; a nucleic acid molecule comprising a nucleotide sequence having at least 70% identity to the sequence of SEQ ID NO:1; a nucleic acid molecule comprising a nucleotide sequence hybridizing under stringent conditions to the sequence of SEQ ID NO:1; and a nucleic acid molecule comprising a nucleotide sequence having an antisense sequence corresponding to one of the above-mentioned sequences. The second DNA construct comprises a nucleotide sequence operably linked to a promoter active in the plant. Expression of the nucleic acid sequence of the second DNA construct modulates the activity of a polypeptide involved in polyglucan synthesis.

In one embodiment, the nucleic acid sequence of the second DNA construct decreases starch synthase activity in the plant. In another embodiment, the nucleic acid sequence of the second DNA construct decreases the activity of a starch branching enzyme in the plant. In another embodiment, the nucleic acid sequence of the second DNA construct decreases the activity of an isoamylase in the plant. In another embodiment, the nucleic acid sequence of the second DNA construct increases the activity of a glucan synthase in the plant. In another embodiment, the nucleic acid sequence of the second DNA construct increases the activity of an isoamylase in the plant.

The methods of the invention find use in increasing the rate of polyglucan digestion. The methods of the invention also find use in creating two distinct pools of polyglucan comprising soluble phytoglycogen and amylose-enriched starch. In addition, the methods of the invention find use in the production of cationic polyglucan and amphoteric polyglucan. Furthermore, methods find use in increasing extractable polyglucan content. Methods also include an improved method of wetmilling.

Compositions of the invention include an expression cassette comprising at least two DNA constructs. The first DNA construct comprises a nucleotide sequence operably linked to a promoter active in the plant, wherein expression of the nucleic acid sequence decreases pullulanase-type activity in the plant. The nucleotide sequence of the first DNA construct comprises a sequence that modulates the activity of a plant pullulanase-like enzyme or fragment thereof. In other embodiments, the nucleotide sequence comprises a sequence of SEQ ID NO:1 or fragment and variants thereof. The second DNA construct comprises a nucleotide sequence operably linked to a promoter active in the plant. Expression of the sequences of the second DNA construct modulates the activity of a polypeptide involved in polyglucan biosynthesis.

Compositions of the invention further include plants and plant cells having modified polyglucan structures. Compositions further comprise the seed and the polyglucan of the above mentioned plant and plant cells. Compositions of the invention further include beverages having carbohydrate compositions comprising the phytoglycogen produced from the methods of the present invention.

DETAILED DESCRIPTION OF THE INVENTION

Compositions and methods are provided for the modification of polyglucan structure to produce a polyglucan or a grain with improved functional properties useful in a wide range of food and industrial applications. By "polyglucan" is intended any polyglucan structure comprising glucose molecules connected by $\alpha 1-4$ glycosidic bonds or $\alpha 1-4$ and $\alpha 1-6$ glycosidic bonds. Constituents of polyglucan comprise phytoglycogen and starch. Starch accumulates as a complex granular structure composed of polyglucan chains comprising amylopectin and amylose. Characteristics of Amylopectin include a high molecular weight ($10^7-10^6$Da) and a polyglucan chain containing approximately 5% $\alpha-1,6$ branches. Amylose is a smaller linear molecule (molecular weight of 105–106Da) and contains very few α1,6 branches (less than 1%) (Ball et al. (1996) *Cell* 86:340–352). Another polyglucan structure is phytoglycogen, characterized as a highly branched water-soluble polysaccharide. The characteristics of amylose, amylopectin and phytoglycogen are further described in Nakamura et al. (1996) *Plant Science* 121:1–18 and in Helt et al. (1997) *Plant Biochemistry and Molecular Biology*, Oxford University Press, both of which are herein incorporated by reference. Modifications of polyglucan structure include but are not limited to a change in the branching pattern of the polyglucan (i.e. a change in the number of branches or the branch length), a change in the overall charge of the branches (for example, through an increase in glucan phosphorylation or an increase in glucan amine content), or any other modification that alters the solubility properties of the polyglucan when compared to an unmodified plant. Modification may also refer to an increase in the overall level of polyglucan produced when compared to an unmodified plant.

The present invention provides methods and compositions to simultaneously modulate the function of multiple proteins involved in the polyglucan biosynthesis pathway. Specifically, methods and compositions to modulate the activity of pullulanase are provided. More specifically, methods and compositions are provided to modulate the activity of pullulanase and the activity of another protein in the polyglucan biosynthesis pathway. The "polyglucan biosynthesis pathway" is intended to comprise any protein involved, either directly or indirectly, in the synthesis of the polyglucan molecule. Furthermore, the proteins of the polyglucan biosynthesis pathway can be obtained from any organism which synthesizes polyglucan either in the form of starch or glycogen.

Modifications in the pathway refer to a modulation in activity of a protein in the pathway. By "modulating activity" is intended that the expression or the activity of a protein in the polyglucan biosynthesis pathway is altered in some manner. Modulating activity will result in either a decrease or an increase in the native protein levels of an enzyme in the polyglucan biosynthesis pathway and/or an increase or decrease in protein activity of the enzyme. Modulating activity also comprises expression of an enzyme normally not found in the plant. Thus, plants and plant cells are obtained that have altered levels of proteins of the polyglucan biosynthesis pathway. Such plants, plant cells, and plant tissues are "modified" in that the activities of proteins in the polyglucan biosynthesis pathway are altered. As noted below, various methods are available for creating modified plants, plant cells, and plant tissues including transformation and transfection and breeding. Such techniques will lead to altered expression of proteins in the polyglucan biosynthesis pathway in the modified plant, plant cell or tissue.

The present invention provides methods to alter a "pullulanase-type" enzyme. By "pullulanase-type" enzyme is intended an enzyme that hydrolyzes $\alpha(1\rightarrow 6)$ linkages of pullulan or amylopectin. The enzyme is therefore a debranching or deramifying enzyme. The pullulanase enzyme, according to the invention, breaks down pullulan into maltotriose and amylopectin into linear polyglucan segments. The amino acid sequence of a pullulanase protein is characterized by six motifs conserved in all debranching enzymes (i.e. pullulanase and isoamylase). The pullulanase class of debranching enzymes contains five additional conserved amino acid motifs not found in the isoamylase class. Pullulanase activity has been identified in both plants and bacteria. Plants exhibiting pullulanase activity include maize, rice, oat, sorghum, barley, broad bean, spinach, pea, sugar beet, potato and wheat. For review see Nakamura (1996) *Plant Science* 121:1–18 and references cited therein. Nucleotide sequences encoding plant pullulanases have been isolated, for example, in maize (ZPU1) (Genbank Accession No. AF080567)(SEQ ID NO:1), barley (Genbank Accession No. AF022725), and spinach (Genbank Accession No. X83969). Each of these Genbank Accession Nos. is herein incorporated by reference.

In specific embodiments of the present invention the activity of the maize pullulanase, ZPU1, is modulated. The corn pullulanase gene (Zpu1) is weakly expressed as early as 12 and 14 DAP, and is strongly and uniformly expressed from 18 to at least 32 DAP. ZPU1 is related to rice DBE termed R-enzyme or limit-dextrinase. The proteins are immunologically cross-reactive and are approximately 77% identical in their amino acid sequences. The debranching enzyme is of the pullulanase-type, hydrolyzing alpha-$(1\rightarrow 6)$ branch linkages in branched polysaccharides. The ZPU1 protein is approximately 100 kD in size. ZPU1 is the product of the single-copy maize Zpu1 gene, which has been mapped to the central region of chromosome 2. The Zpu1 gene is transcribed in developing maize endosperm, and to a slight extent in maize embryo and tassel, but not leaves.

The present invention provides methods to simultaneously modulate the function of plant pullulanase and at least one other protein in the polyglucan biosynthesis pathway. Such proteins include, but are not limited to, soluble starch synthase, granule bound starch synthase, starch debranching enzymes, ADP glucose pyrophosphorylase, isoamylases, and starch branching enzymes. Other enzymes that may also be modulated and which can interact, either directly or indirectly, in polyglucan biosynthesis are glutamine:fructose-6-phosphate amidotransferase (GFAT), phosphoglucomutase, UDP-glucose pyrophosphorylase and glycogen synthase (Tarentino and Maley (1976) *FEBS Lett.* 69:175–178; Kirkman et al. (1989) *BioFactors* 2:123–126, both of which are herein incorporated by reference).

Starch synthase transfers a glucose residue from ADP-glucose to the OH-group in the 4-position of the terminal glucose molecule in the polysaccharide chain. Several plant granule-bound starch synthases are known in the art. Examples of granule-bound starch synthases include, but are not limited to, pea (Genbank Accession No. AF031162), barley (Genbank Accession No. X07931), potato (Genbank Accession Nos. 58453 and A23741), maize (Genbank Accession Nos. X03935 and 22509)(SEQ ID NO:3), sorghum (Genbank Accession No. U23945), sweet potato (Genbank Accession Nos. AF068834 and AF 111157), wheat (Genbank Accession No. D10657, AB019623), sugar beet (Genbank Accession No. AF173652), and rice (Genbank Accession Nos. AF092444, AF092443, and A1736032). Each of these Genbank Accession Nos. is herein incorporated by reference.

Variants of plant starch synthases include both loss of function, recessive, and gain of function, dominant, mutant alleles. For example, the major granule-bound starch synthase in maize is encoded by the Wx gene. Recessive mutations in Wx resulting in either the absence or a decrease in the granule-bound starch synthase activity have been identified (Nelson et al. (1968) Genetics 60:507–524, Shure et al. (1983) *Cell* 35:225–233, Wessler et al. (1985) PNAS 82:4177–4181, and Klosgen et al. (1986) *Mol Gen Genet* 203:237–244). Other variant of plant granule bound starch synthases include: the amf-1 from potato (Visser et al. (1989) *Plant Science* 64:185–192), the Wx-D1b null allele from wheat (Genbank Accession No. AF113844), and the Wx-A1 allele from wheat (Genbank Accession No. AF113843). Each of these Genbank Accession Nos. is herein incorporated by reference.

Glucan synthases incorporate UDP glucose into the polyglucan chain. Such enzymes are optimized for incorporation of amine-containing sugars and include, but are not limited to, glutamine:fructose-6-phosphate amidotransferase and mammalian glycogen synthase. See for example, Tarentino and Maley (1976) *FEBS Lett.* 69:175–178. Maize glutamine:fructose-6-phosphate amidotransferase sequences (SEQ ID NO:5) can be found in U.S. patent application Ser. No. 09/379,779, filed Aug. 24, 1999, herein incorporated by reference. Mammalian glycogen synthases are also known in the art and include, but are not limited to glycogen synthase from Mus Musculus (Genbank Accession No. X94616) and human liver glycogen synthase (Genbank Accession No. D29685)(SEQ ID NO:7). Each of these Genbank Accession Nos. is herein incorporated by reference. Branches on polyglucan are formed by branching enzymes. At certain chain lengths the polysaccharide chain is cleaved at the $(\alpha 1\rightarrow 4)$ glycosidic bond and the chain fragment thus separated is connected via a newly formed (α1→6) to a neighboring chain. These chains are elongated further by starch synthase until a new chain develops. Starch branching enzymes from plants are composed of two isoforms, BEI and BEII. The two isoforms exhibit different kinetic and physio-chemical properties and their relative distribution depends on the plant species and the tissue. Nucleotide sequences encoding branching enzymes in plants are available, for example: barley starch branching enzyme IIb (Genbank Accession No. AF06456), and starch branching enzyme IIa (Genbank Accession No. AF064560), maize starch branching enzyme IIa (SBEIIa) (Genbank Accession Nos. 465948 and U65948)(SEQ ID NO:9), a potato starch branching enzyme (Genbank Accession No. A43341, A43340), rice branching enzyme-1 (Genbank Accession No. D11082), maize starch branching enzyme-1 (SBE1) (Genbank Accession Nos. D11081 and 217959)(SEQ ID NO:13), rice branching enzyme II (Genbank Accession No. X80010), rice branching enzyme I (Genbank Accession No. X80009), and maize starch branching enzyme IIb (SBEIIb) (Genbank Accession Nos. AAC33764 and AF02725)(SEQ ID NO:11). Each of these Genbank Accession Nos. is herein incorporated by reference.

Variants of plant starch branching enzymes include both dominant and recessive mutant alleles. For example, the maize amylose extender mutation (ae) gene, encodes branching enzyme IIb. See, for example, Gao et al. (1997) *Plant Physiol* 114:69–78; Burton et al. (1995) *Plant J*. 7:3–15). In addition, a transgenic mutation of maize starch branching enzyme I has also been identified (Lightner et al. (1999)415$^{st}$ Annual Maize Genetics Conference, March 11–14, Lake Geneva, Wis).

ADP-glucose pyrophosphorylase comprises multiple subunits and catalyzes the formation of ADP glucose. The subunits comprising this enzyme are known in the art and include, for example, sugar beet (Genbank Accession Nos. X78900 and X78899), sweet potato (Genbank Accession Nos. AJ24925 and AJ249256), barley (Genbank Accession No. AJ239130), sorghum (Genbank Accession No. U87452), rice U87450, maize (Genbank Accession Nos. M81603, S48563, and M79333) and soybean (Genbank Accession No. A1900360). Variant of ADP-glucose pyrophosphorylase include both dominant and recessive mutant alleles and include, for example, the alleles of the maize shrunken (Genbank Accession Nos. AF162682 and L35934) or alleles of the brittle gene from soybean (Genbank Accession No. A1900360) or from maize (Genbank Accession No. M79333). Each of these Genbank Accession Nos. is herein incorporated by reference.

Isoamylases cleave α(1→6) branch linkages in amylopectin and glycogen but do not hydrolyze the chemically identical bonds in pullulan. Plant isoamylases include, but are not limited to, potato (Genbank Accession No. AF142591), maize (SU1) (Genbank Accession Nos. D90908 and AF030882)(SEQ ID NO:15), and barley (Genbank Accession No. AF142589) are also known in the art. Each of these Genbank Accession Nos. is herein incorporated by reference.

It is recognized that the activity of a protein in the polyglucan biosynthesis pathway may be modulated indirectly. For example, mutations in the Dull gene of maize modulate expression of a maize soluble starch synthase isoform and a starch branching enzyme. See, for example, U.S. Pat. No. 5,675,064. Alternatively, activity may be indirectly modulated by altering the activity of a protein involved in a transcriptional or post-transcriptional regulatory event of a protein in the polyglucan biosynthesis pathway.

Several methods are available in the art for modulating the activity of the pullulanase and other polypeptides of the polyglucan biosynthesis pathway. Such methods include, but are not limited to: antisense downregulation, cosuppression, or overexpression via the insertion of one or more extra copies of the selected sequence into the genome.

Methods to assay for either an increase or decrease in activity of the various polypeptides involved in polyglucan biosynthesis are known in the art. For example, transcript levels can be assayed using standard molecular biology techniques. Alternatively, assays for enzymatic activity are also known in the art. For example, isoamylase activity can be measured by incubating the extract containing the isoamylase polypeptide with amylopectin in 50 mM Hepes-NaOH, pH 7.0, for 2 hours at 30° C. An aliquot of this reaction is subsequently mixed with water and a 0.01 M $I_2$/0.5 M KI solution. The change in $A_{550}$ is measured relative to a blank amylopectin reaction lacking protein extract. See, for example, Beatty et al. (1999) *Plant Physiology* 119:255–266, herein incorporated by reference. Further assays for isoamylase activity can be found in U.S. Pat. No. 5,750,876, herein incorporated by reference.

Pullulanase-type activity can be assayed by incubating the extract containing the enzyme with pullulan and 50 mM citrate, pH 5.5, at 37° C. Activity is assayed as a change of absorption ($A_{550}$) relative to a blank pullulan reaction. See, for example, Beatty et al. (1999) *Plant Physiology* 119:255–266. Further assays for pullulanase-type enzymatic activity can be found in, for example, U.S. Pat. No. 5,736,375, herein incorporated by reference.

Assays for granule-bound starch synthases are also known in the art. Such assays include measuring the affinity for ADP glucose and glucan substrates, activation by amylopectin, and the processivity of glucan chain extension. Such assays can be found in, for example, Edwards et al. (1999) *European J. Biochem.* 266:724–736, herein incorporated by reference. Activity of starch branching enzymes can be assayed by monitoring the rate of branching amylose and the rate of branching amylopectin. Details regarding these assays can be found in, for example, Guan et al. (1994) *Plant Physiology* 104:1449–1453 and Guan et al. (1994) *Cell Mol. Biol.* 40:981–988, both of which are herein incorporated by reference. Assays for liver glycogen synthase are described in, for example, Wang et al. (1998) *Chin. Med. J.* 111:32–34, herein incorporated by reference.

Glutamine:fructose-6-phosphate amidotransferase catalyzes the rate-limiting step of the hexosamine biosynthetic pathway. Specifically, a GFAT enzyme catalyzes the formation of glucasamine-6-phosphate and glutamate from fructose-6-phosphate in glutamine. Assays to measure this activity in vitro are known in the art. For example, the-GFAT enzyme is incubated with substrate and the product glucosamine-6-phosphate is measured with a standard assay, such as a colorimetric assay. For example, Bessal et al. (1972) *Plant Physiology* 49:977 describe an assay in which a sample containing the GFAT enzyme is mixed with D-fructose-6-phosphate and L-glutamine. The mixture is incubated at 30° C. for 1.5 hours and boiled for 2 minutes to stop the reaction. Following centrifugation, an aliquot of the supernatant was analyzed for D-glucosamine-6-phosphate using a modification of the colormetric assay by Ghosh et al. (1960) *J. Biol. Chem.* 235:1265. Alternatively, GFAT enzyme activity can be measured using a radioenzymatic assay in which the enzyme converts radiolabeled fructose-6-phosphate to radiolabeled glucosamine-6-phosphate. Such assays are described in U.S. application Ser. No. 09/379,779 filed Aug. 24, 1999, herein incorporated by reference.

Fragments and variants of the nucleotide sequences and proteins encoded thereby can be used in the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence modulate polyglucan structure. Use of such fragments will increase the activity of the polypeptide in the cell. Alternatively, fragments of a nucleotide sequence that are useful as hybridization probes generally do not encode proteins retaining biological activity. Furthermore, fragments used to decrease the activity of a polypeptide involved in polyglucan biosynthesis using antisense or cosuppression technology also may not encode a polypeptide having biological activity. However, expression of such fragments do result in a decrease in activity of a polypeptide involved in polyglucan synthesis. Thus, fragments of a nucleotide sequence may range from at least about 20 nucleotides, about 50 nucleotides, about 100 nucleotides, and up to the full-length nucleotide sequence encoding the proteins of the invention.

A fragment of a nucleotide sequence that encodes a biologically active portion or a non-biologically active portion of a polyglucan biosynthesis protein of the invention will encode at least 15, 25, 30, 50, 100, 150, 200, or 250 contiguous amino acids, or up to the total number of amino acids present in a full-length protein of the invention. Fragments of a nucleotide sequence encoding a polyglucan biosynthesis protein that are useful as hybridization probes or PCR primers generally need not encode a biologically active portion of the protein. Similarly, nucleic acid fragments used to decrease the activity of the polyglucan biosynthesis polypeptide using antisense or cosuppression technology need not encode a polypeptide having biological activity. Such fragments of a nucleotide sequence may range from at least about 20 nucleotides, about 50 nucleotides, about 100 nucleotides, and up to the full length nucleotide sequence of the invention.

Thus, a fragment of a nucleotide sequence may encode a biologically active portion of a polyglucan biosynthesis protein, or it may be a fragment that can be used as a hybridization probe/PCR primer or using cosuppression or antisense technology as disclosed in more detail below. A biologically active portion of a polyglucan biosynthesis protein can be prepared by isolating a portion of one of the nucleotide sequences encoding a polyglucan biosynthesis protein, expressing the encoded portion of the protein (e.g., by recombinant expression in vitro), and assessing the activity of the encoded portion of the polyglucan biosynthesis protein. Nucleic acid molecules that are fragments of a nucleotide sequence that modulate the activity of a polypeptide involved in polyglucan biosynthesis comprise at least 16, 20, 50, 75, 100, 150, 200, 250, 300, 350, 400, 450, 500, 550, 600, 650, 700, 800, 900, 1,000, 1,100, 1,200, 1,300, or 1,400 nucleotides, or up to the number of nucleotides present in a full-length nucleotide sequence of the protein.

Alternatively, variants of nucleotide sequences that encode polypeptides involved in polyglucan biosynthesis need not retain biological activity of the encoded protein. Such sequences find use in cosuppression, antisense technology and breeding techniques using recessive mutations. Expression of such variant nucleotide sequences will result in a decrease in the activity of the targeted polypeptide involved in polyglucan biosynthesis. Assays to measure a decrease in activity include, for example, a decrease in transcript levels or enzymatic activity using various assays known in the art. Such variants will have about 40%, 50%, 60%, 65%, 70%, 75%, 80%, 85%, 90%, 91%, 92%, 93%, 95%, 96%, 97%, 98%, 99% or more sequence identity.

By "variants" is intended substantially similar sequences. For nucleotide sequences, conservative variants include those sequences that, because of the degeneracy of the genetic code, encode the amino acid sequence of a protein in the polyglucan biosynthesis pathway. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a protein in the polyglucan biosynthesis pathway. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, they modulate polyglucan structure. Such variants may result from, for example, genetic polymorphism or from human manipulation. Biologically active variants of a native protein in the polyglucan biosynthesis pathway will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the polyglucan biosynthesis proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences used in the present invention include both the naturally occurring sequences as well as mutant forms. Likewise, the proteins of the invention encompass both naturally occurring proteins as well as variations and modified forms thereof. Such variants will continue to possess the desired ability to modulate polyglucan structure. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assaying the characteristics of the polyglucan synthesized. See Experimental section for methods to analyze the physical properties of polyglucan. Alternatively, the enzymatic activity can be assayed using methods described herein.

Variant nucleotide sequences and proteins also encompass sequences and proteins derived from a mutagenic and recombinogenic procedure such as DNA shuffling. With such a procedure, one or more different polyglucan biosynthesis protein coding sequences can be manipulated to create a new protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a gene encoding a polyglucan biosynthesis protein of the invention and other known polyglucan biosynthesis genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Cramen et al. (1997) *Nature Biotech.* 15:436–438; Moore et al. (1997) *J. Mol. Biol.* 272:336–347; Zhang et al. (1997) *Proc. Nall. Acad. Sci. USA* 94:4504–4509; Crameri et al. (1998) *Nature* 391:288–291; and U.S. Pat. Nos. 5,605,793 and 5,837,458.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res*.16:10881–90; Huangetal. (1992) *CABIOS*8:155–65; and Pearson et al. (1994) *Meth. Mol. Biol.* 24:307–331. The ALIGN program is based on the algorithm of Myers and Miller (1988) supra. A PAM 120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.hlm.nih.gov. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J Mol. Biol.* 48:443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff(1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 56C lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}p$, or any other detectable marker. Thus, for example, probes for hybridization can be made by labeling synthetic oligonucleotides based on the sequence encoding proteins of the polyglucan biosynthesis pathway. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60?C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 hours to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point $(T_m)$ for the specific sequence and its complement at a defined ionic strength and pH. However, severely stringent conditions can utilize a hybridization and/or wash at 1, 2, 3, or 4° C. lower than the thermal melting point $(T_m)$; moderately stringent conditions can utilize a hybridization and/or wash at 6, 7, 8, 9, or 10° C. lower than the thermal melting point $(T_m)$; low stringency conditions can utilize a hybridization and/or wash at 11, 12, 13, 14, 15, or 20° C. lower than the thermal melting point $(T_m)$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for a protein of the polyglucan biosynthesis pathway and which hybridize under stringent conditions to the sequences encoding the polyglucan biosynthesis proteins disclosed herein, or to fragments thereof, are encompassed by the present invention. Such sequences will be at least about 40% to 50% homologous, about 60%, 65%, or 70% homologous, and even at least about 75%, 80%, 85%, 90%, 91%, 92%, 93%, 94%, 95%, 96%, 97%, 98%, 99% or more homologous with the disclosed sequences. That is, the sequence identity of sequences may range, sharing at least about 40% to 50%, about 60%, 65%, or 70%, and even at least about 75%, 80%, 85%, 90%, 91%, 92%, 93%, 94%, 95%, 96%, 97%, 98%, 99% or more sequence identity.

The nucleotide sequence of the present invention that modulate the polyglucan biosynthesis pathway can be provided in expression cassettes for expression in a plant of interest. The expression cassette will include 5' and 3' regulatory sequences operably linked to a nucleic acid sequence encoding a pullulanase polypeptide or a nucleic acid sequence which, upon expression, downregulates the activity of the endogenous pullulanase enzyme. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Specific embodiments of the present invention require at least one additional gene to be co-transformed into the organism. A single expression cassette may contain a pullulanase nucleic acid sequence that, upon expression, modulates activity of the nucleic acid sequence and at least one additional gene. Alternatively, the additional gene(s) can be provided on multiple expression cassettes. In specific embodiments, the additional genes co-transformed into the plant include nucleic acid sequences that, upon expression, modulate the activity of a polypeptide involved in the polyglucan biosynthesis pathway.

Such an expression cassette is provided with a plurality of restriction sites for insertion of the nucleic acid sequence encoding a protein of the polyglucan biosynthesis pathway to be under the transcriptional regulation of the regulatory regions. The expression cassette may additionally contain selectable marker genes.

The expression cassette will include in the 5'-3' direction of transcription, a transcriptional and translational initiation region, a coding sequence of the pullulanase protein and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced.

While it may be preferable to express the sequences using heterologous promoters, the native promoter sequences may be used. Such constructs would change expression levels of the polyglucan biosynthesis proteins in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.*17:7891–7903; and Joshi et al. (1987) *Nucleic Acid Res.* 15:9627–9639.

Where appropriate, the nucleic acid sequence may be optimized for increased expression in the transformed plant. That is, the nucleic acid sequence can be synthesized using plant-preferred codons for improved expression. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences-in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also.be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants.

Such constitutive promoters include, for example, the core promoter of the Rsyn7 (PCT application Serial No. U.S. Ser. No. 99/03,863); the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Tissue-preferred promoters can be utilized to target the expression of the pullulanase protein within a particular plant tissue. Tissue-preferred promoters include Yamamoto et al. (1997) *Plant J.* 12(2):255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini etal. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol Biol.*

23(6):1129–1138; Matsuoka et al. (1993) *Proc Natl. Acad. Sci. USA* 90(20):9586–9590, and Guevara-Garcia et al. (1993) *Plant J* 4(3):495–505. Such promoters can be modified, if necessary, for weak expression. "Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and ce1A (cellulose synthase). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc.

Root-specific promoters are known and can be selected from the many available from the literature or isolated de novo from various compatible species. See, for example, Hire et al. (1992) *Plant Mol. Biol.* 20(2):207–218 (soybean root-specific glutamine synthetase gene); Keller and Baumgartner (1991) *Plant Cell* 3(10):1051–1061 (root-specific control element in the GRP 1.8 gene of French bean); Sanger et al. (1990) *Plant Mol. Biol.* 14(3):433–443 (root-specific promoter of the mannopine synthase (MAS) gene of Agrobacterium tumefaciens); and Miao et al. (1991) *Plant Cell* 3(l):11–22 (full-length cDNA clone encoding cytosolic glutamine synthetase (GS), which is expressed in roots and root nodules of soybean). See also Bogusz et al. (1990) *Plant Cell* 2(7):633–641, where two root-specific promoters isolated from hemoglobin genes from the nitrogen-fixing non-legume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69–76). They concluded that enhancer and tissue-preferred DNA determinants are dissociated in those promoters. Teeri et al. (1989) used gene fusion to lacZ to show that the Agrobacterium T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343–350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759–772); and rolB promoter (Capana et al. (1994) *Plant Mol. Biol.* 25(4):681–691. See also U.S. Pat. Nos. 5,837,876; 5,750,386; 5,633,363; 5,459,252; 5,401,836; 5,110,732; and 5,023,179.

In a specific embodiment, the nucleic acid sequence that modulates the activity of a polypeptide involved in the polyglucan biosynthesis pathway is targeted to the chloroplast and/or amyloplast for expression. In this manner, where the nucleic acid of interest is not directly inserted into the plastid, the expression cassette will additionally contain a nucleic acid encoding a transit peptide to direct the nucleic acid of interest to the plastid. Such transit peptides are known in the art. See, for example, Von Heijne et al. (1991) *Plant Mol. Biol. Rep.* 9:104–126; Clark et al. (1989) *J. Biol. Chem.* 264:17544–17550; Della-Cioppa et al. (1987) *Plant Physiol.* 84:965–968; Romer et al. (1993) *Biochem. Biophys. Res. Commun.* 196:1414–1421; and Shah et al. (1986) *Science* 233:478–481.

Plastid targeting sequences are known in the art and include the chloroplast small subunit of ribulose-1,5-bisphosphate carboxylase (Rubisco) (de Castro Silva Filho et al. (1996) *Plant Mol. Biol.* 30:769–780; Schnell et al. (1991) *J. Bio. Chem.* 266(5):3335–3342); 5-(enolpyruvyl) shikimate-3-phosphate synthase (EPSPS) (Archer et al. (1990) *J. Bioenerg. Biomemb.* 22(6):789–810); tryptophan synthase (Zhao et al. (1995) *J. Biol. Chem.* 270(11):6081–6087); plastocyanin (Lawrence et al. (1997) *J. Biol. Chem.* 272(33):20357–20363); chorismate synthase (Schmidt et al. (1993) *J. Biol. Chem.* 268(36):27447–27457); and the light harvesting chlorophyll a/b binding protein (LHBP) (Lamppa et al. (1988) *J Biol. Chem.* 263:14996–14999). See also Von Heijne et al. (1991) *Plant Mol. Biol. Rep.* 9:104–126; Clark et al. (1989) *J. Biol. Chem.* 264:17544–17550; Della-Cioppa et al. (1987) *Plant Physiol.* 84:965–968; Romer et al. (1993) *Biochem. Biophys. Res. Commun.* 196:1414–1421; and Shah et al. (1986) *Science* 233:478–481.

Methods for transformation of chloroplasts are known in the art. See, for example, Svab et al. (1990) *Proc. Natl. Acad. Sci. USA* 87:8526–8530; Svab and Maliga (1993) *Proc. Natl. Acad. Sci. USA* 90:913–917; Svab and Maliga (1993) *EMBO J.* 12:601–606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301–7305.

The nucleic acids of interest to be targeted to the chloroplast and/or amyloplast may be optimized for expression in the plastid to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al (1992) *Cell* 71:63–72; Reznikoff(1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natt. Acad. Aci. USA* 86:5400–5404; Fuerst et al. (1989) *Proc. Natl. Acad. Sci. USA* 86:2549–2553; Deuschle et al. (1990) *i Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956;.Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10: 143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334:721–724. Such disclosures are herein incorporated by reference. The above list of selectable marker genes is not meant to be limiting. Any selectable marker gene can be used in the present invention.

In specific embodiments of the present invention, the nucleotide sequences of pullulanase and the other proteins of the polyglucan biosynthesis pathway can be used to generate antisense constructions, which are complementary to at least a portion of the messenger RNA (mRNA) encoding these proteins. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

By "introducing" sequences that modulate polyglucan biosynthesis into a target plant is intended any means for incorporating the sequence of interest into the target plant. Such means includes conventional breeding methods, genetic transformation methods, or other such means as may be available. The methods of the invention do not depend on a particular method for introducing a nucleotide construct to a plant, only that the nucleotide construct gains access to the interior of at least one cell of the plant. By "stable transformation" is intended that the nucleotide construct introduced into a plant integrates into the genome of the plant and is capable of being inherited by progeny thereof. The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 15 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and thenseeds harvested to ensure constitutive expression of the desired phenotypic characteristic has been achieved.

The present invention may be used for transformation of any plant species, including, but not limited to, monocots and dicots. Examples of plants of interest include, but are not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C. melo*). Ornamentals include azalea (Rhododendron spp.), hydrangea (Macrophylla hydrangea), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, etc. Oil seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Embodiments of the present invention produce transgenic plants that combine modulating pullulanase debranching activity and at least one other protein of the polyglucan biosynthesis pathway. A decreased pullulanase activity will produce high levels of free sugars and increased levels of a highly branched polysaccharide (phytoglycogen) in the maize endosperm. By "increased levels" it is intended an increase in phytoglycogen content by about 15% to about 50%, particularly about 20% to about 30% over that found in an unmodified plant. Phytoglycogen is water-soluble, as are the free sugars, and is more readily available to digestion than granular starch of which the release is restricted by matrix factors in the kernel. In addition, reduction of pullulanase activity will reduce starch granule size, which will increase the effective surface area and further enhance the rate of enzymatic digestion. For example, using the automated in vitro gas measurement system described by Pell and Schofield (1993) *J. Dairy Sci* 76:1063–1073 and Schofield and Pell (1995) *J. Anim. Sci* 73:3455–3463, we have discovered the rate of digestion of phytoglycogen to be 34% higher than that of isolated corn starch (5.89 versus 4.38 ml/h). Thus, the available energy for monogastric and ruminant livestock is elevated in corn producing high levels of phytoglycogen.

Furthermore, reduction of pullulanase activity may produce starch granules which display a reduced temperature of gelatinization that would increase starch solubility during processing (grinding, pelleting, steam flaking) at temperatures below the gelatinization temperature of normal starch. The reduced gelatinization temperature would elevate the degree of starch gelatinization in processed feed and hence, starch digestibility, and reduce the energy required in feed processing (grinding, pelleting, steam-flanking).

Production of controlled levels of rapidly fermentable sugars and/or phytoglycogen in corn grain will also ensure adequate levels of fermentable carbohydrate in silage made from whole corn plants, and will provide corn to be used in silage additive to high protein silage. Such corn will provide the rapidly fermentable carbohydrates required for lactic acid formation to improve preservation, palatability, and nutritional value silage made from high protein forage. For corn silage, by "controlled levels" is intended about a 5% to about 30%, particularly about a 5% to about 10% increase in phytoglycogen and/or rapidly fermentable sugars over that found in an unmodified plant. For corn grain to be used as an additive to high protein silages, by "controlled levels" is intended about 5% to about 30%, particularly from about 20–30% increase in phytoglycogen and/or rapidly fermentable sugars over that found in an unmodified plant. "High protein silages" comprises silages prepared from legumes including but not limited to alfalfa and red clover.

Polyglucan structure may be modified further by modulating the activity of at least one additional enzyme of the polyglucan biosynthesis pathway. In an embodiment of the present invention, the rate of carbohydrate digestion is further increased by combining the decreased pullulanase activity with the waxy trait (all amylopectin starch). By "increase" is intended the rate of polyglucan digestion is about 5% to about 15%, from about 15% to about 25%, preferably from about 25% to about 35%, and more preferably from about 35% to 50% or greater than that of isolated polyglucan from an unmodified plant. Methods for measuring the rate of polyglucan digestion are known in the art and described in Pell and Schofield (1993) *J. Dairy Sci* 76:1063–1073 and in Schofield and Pell (1995) *J. Anim. Sci* 73:3455–3463, both of which are herein incorporated by reference. The approach could be entirely transgenic (suppressing expression of both pullulanase and a granule bound starch synthase) or by transferring the waxy mutation into a newly obtained transgenic plant with a decreased pullulanase activity. In a specific embodiment, the waxy trait is conferred by the granule-bound starch synthase, GBSSI, of maize and the pullulanase is ZPU1 of maize.

In another embodiment, the rate of polyglucan digestion is increased by combining the decreased pullulanase activity with a decreased isoamylase activity. The approach can be entirely transgenic (suppressing both pullulanase and isoamylase or by transferring the sugary mutation into a newly obtained transgenic plant with decreased pullulanase activity. In a specific embodiment, the sugary trait is conferred by disrupting the activity of the isoamylase, SU1 of maize, and the pullulanase activity disrupted is that of maize ZPU1.

Another embodiment of the present invention combines a decreased pullulanase activity with an increased amylose trait. By "increased" it is intended about 40% to about 95%, particularly about 40% to about 70% of the starch is amylose. The approach will create two distinct pools of carbohydrates (soluble phytoglycogen and amylose-enriched starch) to optimize energy utilization by ruminant livestock. Of these two carbohydrate pools, the soluble sugars and phytoglycogen will supply rumen microorganisms with easily fermnentable carbohydrate and the high amylose starch would be partly protected from degradation in the rumen but still available for digestion in the small intestine. The approach could be entirely transgenic (suppressing expression of both pullulanase and one of several starch branching enzymes) or by transferring a starch branching enzyme mutation into a newly obtained transgenic plant with a decreased pullulanase activity. In a specific embodiment, the mutation that alters starch branching enzyme activity is the maize SBEI, SBEIIa, or SBEIIb and the pullulanase is ZPU1 of maize. In another specific embodiment the decrease in starch branching enzyme activity is conferred by a transgenic mutation of maize starch branching enzyme-I (Lightner et al. (1999) 41 st Annual Maize Genetics Conference, March 11–14, Lake Geneva, Wis.).

The phosphorylation levels of glucans in starch granules may be increased upon reduction of pullulanase activity. Starch granule phosphate levels are elevated in sugary starch (Morrison and Karkalas (1990) *In: Methods in Plant Biochemistry Vol.*2), which could be dependent upon pullulanase activity, since pullulanase is involved in the branching pattern and there is a relationship between the degree of polyglucan phosphorylation and chain length distribution in amylopectin (Bennow et al. (1998) *Carb. Res.* 307:45–54). We have reconfirmed this, and have also discovered that the level of phosphorylation is even greater in phytoglycogen from sugary1: the phosphorous levels we measured were 1.6, 5.8, and 25.1 mg % P in lipid-free corn amylopectin, sugary starch, and phytoglycogen, respectively.

An expected outcome of a reduction in pullulanase activity would be the elicitation of the phosphorylation mechanism, which in turn would lead to about a 2-fold or higher increase in the level of covalent phosphorylation of $\alpha 1,4$–$\alpha 1,6$ glucan found within starch granules. This in turn may alter the branching pattern of amnylopectin. Industrial applications involving polyglucan phosphates are described in, for example, Rutenberg and Solarek (1984) *Starch: Chemistry and Technology*, R. L. Whistler et al., eds, Academic Press and Solarek (1986) *Modified Starches: Properties and Uses, O. B. Wurzburg, ed. CRC Press*, both of which are herein incorporated by reference.

In an embodiment of the present invention, the charge of the polyglucan is modified. In this embodiment, the increased phosphorylation levels of the 1,4–1,6 glucan in the presence of reduced pullulanase activity is used in combination with transgenic plants containing glucan synthases optimized for the incorporation of amine-containing sugars into the polyglucan chain. The approach can be entirely transgenic, suppressing expression of pullulanase while overexpressing a glycogen synthase. In a specific embodiment the pullulanase suppressed is maize ZPU1 and the glycogen synthase is maize glutamine:fructose-6-phosphate amidotransferase or human liver glycogen synthase. This approach can produce amphoteric polysaccharides which have uses in several non-feed applications, including but not limited to explosives, oil field chemicals, textile fibers, personal care products, agricultural chemicals cosmetics and, most notably, paper manufacturing. See, for example, U.S. patent application No. 5,378,830 and Wurzburg, ed. (1986) *Modified Starches: Properties and Uses*, CRC Press, both of which are herein incorporated by reference.

Alternatively, the increased incorporation of the amines into the polyglucan can produce a cationic polyglucan that disrupts ordinary formation of starch. The suppression of pullulanase activity could enhance the ability of the cell to divert assimilates into the synthesis of phytoglycogen, a polymer that would be desired in this application and one that does not require integration into granules.

A further embodiment of the present invention maximizes starch accumulation in corn endosperm (at the expense of soluble sugars and polysaccharides) by increasing the levels of starch debranching enzymes and thereby reducing starch solubility. Cutting the normal levels of soluble sugars plus phytoglycogen (3–5%) in half will increase starch content, and presumably extractable starch, by about 1–2 percentage points, about 2% to about 4% and from about 4% to about 10%. The grain from such plants would therefore offer an improved method of wet milling. By "wet milling" is intended a method of obtaining polyglucan from plants. Wet milling is a multi-step process involving steeping and grinding kernels and separating the kernels into starch, protein, oil, and fiber fractions. A review of the maize wet milling process is given by S. R. Eckhoff in the Proceedings of the 4th Corn Utilization Conference, Jun. 24–26, 1992, St. Louis, Mo., printed by the National Corn Growers Association, CIBA-GEIGY Seed Division, and the USDA. This approach can be achieved by overexpression of pullulanase, preferably maize Zpu1. Alternatively, this approach can be achieved by generating a transgenic plant that overexpresses a pullulanase and an isoamylase. In specific embodiments, the pullulanase and isoamylase is from a plant, preferably maize ZPU1 and SU1.

A further embodiment comprises the use of phytoglycogen in beverages, such as in sports drinks. Digestion and absorption patterns of phytoglycogen are expected to be intermediate between those of soluble sugars and starch, resulting in lower glycemic indices than those obtained with sugars. Therefore, phytoglycogen may be used as an ingredient for beverages that require a rapid but sustained-release carbohydrate. Plants having reduced pullulanase or pullulanase and isoamylase activity would be produced for the purpose of generating grain enriched in water soluble phytoglycogen. This approach will result in an increase in phytoglycogen content. By "increase" is intended an increase in phytoglycogen content of about 15% to about 50%, particularly about 20% to about 30% over that found in an unmodified plant. The approach could be entirely transgenic (suppressing expression of pullulanase and isoamylase) or by transferring a sugary mutation into a newly obtained transgenic plant with a decreased pullulanase activity. In a specific embodiment, the sugary trait is conferred by disrupting the activity of the isoamylase, SU1 of maize, and the pullulanase activity disrupted is that of maize ZPU1.

EXPERIMENTAL

EXAMPLE 1

Transformation and Regeneration of Transgenic Plants

Immature maize embryos from greenhouse donor plants are bombarded with a plasmid containing two DNA constructs. The first DNA construct comprises an antisense nucleotide sequence corresponding to the ZPU1 polypeptide (SEQ ID NO:1) operably linked to a gamma-zein promoter. The second DNA construct comprises a nucleotide sequence encoding an antisense sequence corresponding to a nucleotide sequence encoding a protein of the polyglucan biosynthesis pathway operably linked to a gamma-zein promoter. The plasmid also contains a selectable marker gene PAT (Wohlleben et al. (1988) *Gene* 70:25–37) that confers resistance to the herbicide Bialaphos. Transformation is performed as follows. All media recipes are shown below.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector is generated. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in TrisEDTA buffer (1 μg total)
100 μl 2.5M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34–1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity.

Analysis

Methods to analyze the biochemical and biophysical properties of polyglucans are well known in the art. Such techniques include, for example, light microscopy for the study of morphological alterations of the starch granules and a Particle Size Analyzer to determine the particle size distribution of the granules. Chain length may be determined using the methods described in U.S. Pat. No. 5,750,876, herein incorporated by reference. Furthermore, amylose content may be analyzed using the method of Williams et al. (1970) *Cereal Chemistry* 47:411–420. Physical properties such as viscosity and gel strength may be measured using strain sweep test, RVA curves, Brabender curves, and Brookfields viscosity tests as described in U.S. Pat. No. 5,675,064, herein incorporated by reference. Further, methods for measuring the rate of polyglucan digestion can be found in, for example, Pell el al. *J. Dairy Sci.* 76:1063–1073, herein incorporated by reference.

Alternatively, the decrease in pullulanase-type activity and the activity of another polypeptide involved in polyglucan biosynthesis can be monitored by assaying directly for enzymatic activity (as described herein above) or by monitoring the transcript levels of the specific polypeptides being targeted.

Bombardment and Culture Media

Bombardment medium (560Y) comprises 4.0g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2$ O after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS. vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I H20), sterilized and cooled to 60° C.

EXAMPLE 2

Agrobacterium-mediated Transformation

For Agrobacterium-mediated transformation of maize with a plasmid containing two DNA constructs, as described in Example 1, preferably the method of Zhao is employed (U.S. Pat. No. 5,981,840, and PCT patent publication W098/32326; the contents of which are hereby incorporated by reference). Briefly, immature embryos are isolated from maize and the embryos contacted with a suspension of Agrobacterium, where the bacteria are capable of transferring the DNA constructs to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

EXAMPLE 3

Soybean Embryo Transformation Prophetic Example

Soybean embryos are bombarded with a plasmid containing the two DNA constructs, as described in Example 1. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with fluorescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the DNA constructs can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 4

Sunflower Meristem Tissue Transformation Prophetic Example

Sunflower meristem tissues are transformed with an expression cassette, as described in Example 1, as follows (see also European Pat. Number EP 0 486233, herein incorporated by reference, and Malone-Schoneberg et al. (1994) *Plant Science* 103:199–207). Mature sunflower seed (*Helianthus annuus* L.) are dehulled using a single wheathead thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schramrnmeijer et al. (Schrammeijer et al. (1990) *Plant Cell Rep.* 9:55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15:473–497), Shepard's vitamin additions (Shepard (1980) in *Emergent Techniques for the Genetic Inprovement of Crops* (University of Minnesota Press, St. Paul, Minn.), 40 mg/l adenine sulfate, 30 g/l sucrose, 0.5 mg/l 6-benzylaminopurine (BAP), 0.25 mg/l indole-3-acetic acid (IAA), 0.1 mg/l gibberellic acid (GA$_3$), pH 5.6, and 8 g/l Phytagar.

The explants are subjected to microprojectile bombardment prior to Agrobacterium treatment (Bidney et al. (1992) *Plant Mol. Biol.* 18:301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 10001® particle acceleration device.

Disarmed *Agrobacterium tumefaciens* strain EHA105 is used in all transformation experiments. A binary plasmid vector comprising the expression cassette that contains DNA constructs described in Example 1 is introduced into Agrobacterium strain EHA105 via freeze-thawing as described by Holsters et al. (1978) *Mol. Gen. Genet.* 163:181–187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The Agrobacterium cells are pelleted and resuspended at a final $OD_{600}$ of 0.5 in an inoculation medium comprised of 12.5 mM MES pH 5.7, 1 gm/l NH4Cl, and 0.3 gm/l $MgSO_4$.

Freshly bombarded explants are placed in an Agrobacteritim suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for a modulation in polyglucan biosynthesis.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by assaying for a modulation in polyglucan biosynthesis in leaf extracts while transgenic seeds harvested from NPTII-positive $T_0$ plants are identified by assaying for a modulation in polyglucan biosynthesis in small portions of dry seed cotyledon.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

---

What is claimed is:

1. A method for modulating polyglucan biosynthesis in a maize plant comprising stably introducing into the genome of said maize plant at least a first DNA construct and a second DNA construct, wherein
   a) said first DNA construct comprises a first nucleic acid molecule operably linked to a first promoter active in said maize plant, wherein expression of said first nucleic acid molecule decreases pullulanase activity of a maize pullulanase polypeptide capable of hydrolyzing α(1→6) linkages of pullulan in the maize plant, and said first nucleic acid molecule comprises a nucleotide sequence comprising at least 20 contiguous nucleotides encoding the maize pullulanase polypeptide; and,
   b) said a second DNA construct comprises a second nucleotide sequence operably linked to a second promoter active in said maize plant wherein expression of said second nucleotide sequence modulates the activity of a polypeptide involved in polyglucan synthesis and said second nucleotide sequence is selected from the group consisting of:
      i) a nucleic acid molecule comprising a nucleotide sequence that encodes the polypeptide involved in polyglucan synthesis; and,
      ii) a nucleic acid molecule comprising a nucleotide sequence having an antisense sequence corresponding to the second nucleotide sequence in bi).

2. The method of claim 1, wherein said first nucleic acid molecule of said first DNA construct comprises at least 20 contiguous nucleotides of SEQ ID NO:1.

3. The method of claim 2, wherein at least one of said first or said second DNA construct is introduced into the maize plant by transformation.

4. The method of claim 2, wherein at least one of said first or said second DNA construct is introduced into the maize plant by breeding.

5. The method of claim 2, wherein said first or said second DNA constructs are contained in separate expression vectors.

6. The method of claim 2, wherein said first or said second DNA constructs are contained in the same expression vector.

7. A maize plant having stably introduced into its genome
   a) a first DNA construct comprising a first nucleic acid molecule operably linked to a first promoter active in said maize plant, wherein expression of said first nucleic acid molecule decreases pullulanase activity of a maize pullulanase polypeptide capable of hydrolyzing α(1→6) linkages of pullulan in the maize plant and said first nucleic acid molecule comprises a nucleotide sequence comprising at least 20 contiguous nucleotides encoding the maize pullulanase polypeptide; and,
   b) a second DNA construct comprising a second nucleotide sequence operably linked to a second promoter active in said maize plant wherein expression of said second nucleotide sequence modulates the activity of a polypeptide involved in polyglucan synthesis and said second nucleotide sequence is selected from the group consisting of:
      i) a nucleic acid molecule comprising a nucleotide sequence that encodes the polypeptide involved in polyglucan synthesis; and,
      ii) a nucleic acid molecule comprising a nucleotide sequence having an antisense sequence corresponding to the second nucleotide sequence in bi).

8. The maize plant of claim 7, wherein said first nucleic acid molecule of said first DNA construct comprises at least 20 contiguous nucleotides of SEQ ID NO:1.

9. A transformed seed of the plant of claim 8, which transformed seed comprises said first and second DNA constructs.

10. A maize plant cell having stably introduced into its genome
    a) a first DNA construct comprising a first nucleic acid molecule operably linked to a first promoter active in said maize plant cell, wherein expression of said first nucleic acid molecule decreases pullulanase activity of a maize pullulanase polypeptide capable of hydrolyzing α(1→6) linkages of pullulan in the maize plant cell and said first nucleic acid molecule comprises a nucleotide sequence comprising at least 20 contiguous nucleotides encoding the maize pullulanase polypeptide; and,
    b) a second DNA construct comprising a second nucleotide sequence operably linked to a second promoter active in said maize plant cell wherein expression of said second nucleotide sequence modulates the activity of a polypeptide involved in polyglucan synthesis and said second nucleotide sequence is selected from the group consisting of:
       i) a nucleic acid molecule comprising a nucleotide sequence that encodes the polypeptide involved in polyglucan synthesis; and,
       ii) a nucleic acid molecule comprising a nucleotide sequence having an antisense sequence corresponding to the second nucleotide sequence in bi).

11. An expression vector comprising
    a) a first DNA construct comprising a first nucleic acid molecule operably linked to a first promoter active in a plant, wherein expression of said first nucleic acid molecule modulates pullulanase activity of a maize pullulanase polypeptide capable of hydrolyzing α(1→6) linkages of pullulan in a maize plant and said first nucleic acid molecule comprises a nucleotide sequence comprising at least 20 contiguous nucleotides encoding a maize pullulanase polypeptide; and,
    b) a second DNA construct comprising a second nucleotide sequence operably linked to a second promoter active in said maize plant wherein expression of said second nucleotide sequence modulates the activity of a polypeptide involved in polyglucan synthesis and said second nucleotide sequence is selected from the group consisting of:
       i) a nucleic acid molecule comprising a nucleotide sequence that encodes the polypeptide involved in polyglucan synthesis; and,
       ii) a nucleic acid molecule comprising a nucleotide sequence having an antisense sequence corresponding to the second nucleotide sequence in bi).

12. The method of claim 1, wherein said first nucleic acid molecule of said first DNA construct encodes the maize pullulanase polypeptide.

13. The method of claim 2, wherein said first nucleic acid molecule of said first DNA construct comprises the sequence set forth in SEQ ID NO:1.

14. A method for modulating polyglucan biosynthesis in a maize plant comprising stably introducing into the genome of said maize plant at least a first and a second DNA construct, wherein
    a) said first DNA construct comprises a first nucleic acid molecule operably linked to a first promoter active in said maize plant, wherein expression of said first nucleic acid molecule decreases pullulanase activity of a maize pullulanase polypeptide capable of hydrolyzing α(1→6) linkages of pullulan in the maize plant and said first nucleic acid molecule comprises a nucleotide sequence having at least 90% sequence identity to the sequence of SEQ ID NO:1; and,
    b) said second DNA construct comprises a second nucleotide sequence operably linked to a second promoter active in said maize plant wherein expression of said second nucleotide sequence modulates the activity of a polypeptide involved in polyglucan synthesis and said second nucleotide sequence is selected from the group consisting of:
       i) a nucleic acid molecule comprising a nucleotide sequence that encodes the polypeptide involved in polyglucan synthesis; and,
       ii) a nucleic acid molecule comprising a nucleotide sequence having an antisense sequence corresponding to the second nucleotide sequence in bi).

15. The method of claim 14, wherein said first nucleic acid molecule of said first DNA construct comprises a sequence having at least 95% sequence identity to SEQ ID NO:1.

16. A method for modulating polyglucan biosynthesis in a maize plant comprising stably introducing into the genome of said maize plant at least a first and a second DNA construct, wherein
    a) said first DNA construct comprises a first nucleic acid molecule operably linked to a first promoter active in said maize plant, wherein expression of said first nucleic acid molecule decreases pullulanase activity of a maize pullulanase polypeptide capable of hydrolyzing α(1→6) linkages of pullulan in the maize plant and said first nucleic acid molecule comprises an antisense nucleotide sequence comprising at least 50 contiguous nucleotides complementary to the mRNA encoding a maize pullulanase polypeptide; and b) said second DNA construct comprises a second nucleotide sequence operably linked to a second promoter active in said maize plant wherein expression of said second nucleotide sequence modulates the activity of a polypeptide involved in polyglucan synthesis and said second nucleotide sequence is selected from the group consisting of:
   i) a nucleic acid molecule comprising a nucleotide sequence that encodes the polypeptide involved in polyglucan synthesis; and,
   ii) a nucleic acid molecule comprising a nucleotide sequence having an antisense sequence corresponding to the second nucleotide sequence in bi).

17. The method of claim 16, wherein said antisense nucleotide sequence of said first DNA construct hybridizes under stringent conditions to the nucleotide sequence encoding the maize pullulanase polypeptide, wherein said stringent conditions comprise hybridization in 50% formamide, 1 M NaCl, 1% SDS at 37° C., and a wash in 0.1×SSC at 60° C. to 65° C.

18. The method of claim 16, wherein said antisense nucleotide sequence of said first DNA construct comprises at least 50 contiguous nucleotides complementary to the sequence set forth in SEQ ID NO:1.

19. The method of claim 18, wherein said antisense nucleotide sequence of said first DNA construct hybridizes under stringent conditions to the nucleotide sequence set forth in SEQ ID NO:1, wherein said stringent conditions comprise hybridization in 50% formamide, 1 M NaCl, 1% SDS at 37° C., and a wash in 0.1×SSC at 60° C. to 65° C.

20. The maize plant of claim 7, wherein said first nucleic acid molecule of said first DNA construct encodes a maize pullulanase polypeptide.

21. The maize plant of claim 8, wherein said first nucleic acid molecule of said first DNA construct comprises the sequence set forth in SEQ ID NO:1.

22. A maize plant having stably introduced into its genome
a) a first DNA construct comprising a first nucleic acid molecule operably linked to a first promoter active in said maize plant, wherein expression of said first nucleic acid molecule decreases pullulanase activity of a maize pullulanase polypeptide capable of hydrolyzing α(1→6) linkages of pullulan in the maize plant and said first nucleic acid molecule comprises a nucleotide sequence having at least 90% identity to SEQ ID NO:1; and
b) a second DNA construct comprising a second nucleotide sequence operably linked to a second promoter active in said maize plant wherein expression of said second nucleotide sequence modulates the activity of a polypeptide involved in polyglucan synthesis and said second nucleotide sequence is selected from the group consisting of:
   i) a nucleic acid molecule comprising a nucleotide sequence that encodes the polypeptide involved in polyglucan synthesis; and,
   ii) a nucleic acid molecule comprising a nucleotide sequence having an antisense sequence corresponding to tie second nucleotide sequence in bi).

23. The maize plant of claim 22, wherein said first nucleic acid molecule of said first DNA construct comprises a sequence having at least 95% sequence identity to SEQ ID NO:1.

24. A maize plant having stably introduced into its genome
a) a first DNA construct comprising a first nucleic acid molecule operably linked to a first promoter active in said maize plant, wherein expression of said first nucleic acid molecule decreases pullulanase-type activity of a maize pullulanase polypeptide capable of hydrolyzing α(1→6) linkages of pullulan in the maize plant and said first nucleic acid molecule comprises an antisense nucleotide sequence comprising at least 50 contiguous nucleotides complementary to the mRNA encoding the maize pullulanase polypeptide; and,
b) a second DNA construct comprising a second nucleotide sequence operably linked to a second promoter active in said maize plant wherein expression of said second nucleotide sequence modulates the activity of a polypeptide involved in polyglucan synthesis and said second nucleotide sequence is selected from the group consisting of:
   i) a nucleic acid molecule comprising a nucleotide sequence that encodes the polypeptide involved in polyglucan synthesis; and,
   ii) a nucleic acid molecule comprising a nucleotide sequence having an antisense sequence corresponding to the second nucleotide sequence in bi).

25. The maize plant of claim 24, wherein said antisense nucleotide sequence of said first DNA construct hybridizes under stringent conditions to the nucleotide sequence encoding the maize pullulanase polypeptide, wherein said stringent conditions comprise hybridization in 50% formamide, 1 M NaCl, 1×SDS at 37° C., and a wash in 0.1×SSC at 60° C. to 65° C.

26. The maize plant of claim 24, wherein said antisense nucleotide sequence comprises at least 50 contiguous nucleotides complementary to SEQ ID NO:1.

27. The maize plant claim 26, wherein said antisense nucleotide sequence of said first DNA construct hybridizes under stringent conditions to SEQ ID NO:1, wherein said stringent conditions comprise hybridization in 50% formamide, 1 M NaCl, 1% SDS at 37° C., and a wash in 0.1×SSC at 60° C. to 65° C.

28. The maize plant cell of claim 10, wherein said first nucleic acid molecule of said first DNA construct encodes the maize pullulanase polypeptide.

29. The maize plant cell of claim 10, wherein said first nucleic acid molecule of said first DNA construct comprises at least 20 contiguous nucleotides of SEQ ID NO:1.

30. The maize plant cell of claim 29, wherein said first nucleic acid molecule of said first DNA construct comprises the sequence set forth in SEQ ID NO:1.

31. A maize plant cell having stably introduced into its genome
a) a first DNA construct comprising a first nucleic acid molecule operably linked to first promoter active in said maize plant cell, wherein expression of said first nucleic acid molecule decreases pullulanase activity of a maize pullulanase polypeptide capable of hydrolyzing α(1→6) linkages of pullulan in the maize plant cell and said first nucleic acid molecule comprises a nucleotide sequence having at least 90% sequence identity to SEQ ID NO:1; and,
b) a second DNA construct comprising a second nucleotide sequence operably linked to a second promoter active in said maize plant cell wherein expression of said second nucleotide sequence modulates the activity of a polypeptide involved in polyglucan synthesis and said second nucleotide sequence is selected from the group consisting of:
  i) a nucleic acid molecule comprising a nucleotide sequence that encodes the polypeptide involved in polyglucan synthesis; and,
  ii) a nucleic acid molecule comprising a nucleotide sequence having an antisense sequence corresponding to the second nucleotide sequence in bi).

32. The maize plant cell of claim 31, wherein said first nucleic acid molecule of said first DNA construct comprises a sequence having at least 95% sequence identity to the sequence set forth in SEQ ID NO:1.

33. A maize plant cell having stably introduced into its genome
  a) a first DNA construct comprising a first nucleic acid molecule operably linked to a first promoter active in said maize plant cell, wherein expression or said first nucleic acid molecule decreases pullulanase activity of a maize pullulanase polypeptide capable of hydrolyzing α(1→6) linkages of pullulan in the maize plant cell and said first nucleic acid molecule comprises an antisense nucleotide sequence comprising at least 50 contiguous nucleotides complementary to the mRNA encoding the maize pullulanase polypeptide; and,
  b) a second DNA construct comprising a second nucleotide sequence operably linked to a second promoter active in said maize plant cell wherein expression of said second nucleotide sequence modulates the activity of a polypeptide involved in polyglucan synthesis and said second nucleotide sequence is selected from the group consisting of:
    i) a nucleic acid molecule comprising a nucleotide sequence that encodes the polypeptide involved in polyglucan synthesis; and,
    ii) a nucleic acid molecule comprising a nucleotide sequence having an antisense sequence corresponding to the second nucleotide sequence in bi).

34. The maize plant cell of claim 33, wherein said antisense nucleotide sequence of said first DNA construct hybridizes under stringent conditions to the nucleotide sequence encoding the maize pullulanase polypeptide, wherein said stringent conditions comprise hybridization in 50% formamide, 1 NaCl, 1% SDS at 37° C., and a wash in 0.1×SSC at 60° C. to 65° C.

35. The maize plant cell of claim 33, wherein said antisense nucleotide sequence of said first DNA construct comprises at least 50 contiguous nucleotides complementary to SEQ ID NO:1.

36. The maize plant cell claim 35, wherein said antisense nucleotide sequence of said first DNA construct hybridizes under stringent conditions to SEQ ID NO:1, wherein said stringent conditions comprise hybridization in 50% formamide, 1 M NaCl, 1% SDS at 37° C., and a wash in 0.1×SSC at 60° C. to 65° C.

37. The expression vector of claim 11, wherein said first nucleic acid molecule of said first DNA construct encodes the maize pullulanase polypeptide.

38. The expression vector of claim 11, wherein said first nucleic acid molecule of said first DNA construct comprises at least 20 contiguous nucleotides of SEQ ID NO:1.

39. The expression vector of claim 38, wherein said first nucleic acid molecule of said first DNA construct comprises the sequence set forth in SEQ ID NO:1.

40. An expression vector comprising
  a) a first DNA construct comprising a first nucleic acid molecule operably linked to a first promoter active in a plant, wherein expression of said first nucleic acid molecule decreases pullulanase activity of a maize pullulanase polypeptide capable of hydrolyzing α(1→6) linkages of pullulan in a maize plant and said first nucleic acid molecule comprises a nucleotide sequence having at least 90% sequence identity to SEQ ID NO:1; and,
  b) i second DNA construct comprising a second nucleotide sequence operably linked to a second promoter active in said plant wherein expression of said second nucleotide sequence modulates the activity of a polypeptide involved in polyglucan synthesis and said second nucleotide sequence is selected from the group consisting of:
    i) a nucleic acid molecule comprising a nucleotide sequence that encodes the polypeptide involved in polyglucan synthesis; and,
    ii) a nucleic acid molecule comprising a nucleotide sequence having an antisense sequence corresponding to the second nucleotide sequence in bi).

41. The expression vector of claim 40, wherein said first nucleic acid molecule of said first DNA construct comprises a sequence having at least 95% sequence identity to SEQ ID NO:1.

42. An expression vector comprising
  a) a first DNA construct comprising a first nucleic acid molecule operably linked to a first promoter active in a plant, wherein expression of said first nucleic acid molecule decreases pullulanase activity of a maize pullulanase polypeptide capable of hydrolyzing α(1→6) linkages of pullulan in a maize plant and said first nucleic acid molecule comprises an antisense nucleotide sequence comprising at least 50 contiguous nucleotides complementary to the mRNA encoding the maize pullulanase polypeptide; and,
  b) a second DNA construct comprising a second nucleotide sequence operably linked to a second promoter active in said plant wherein expression of said second nucleotide sequence modulates the activity of a polypeptide involved in polyglucan synthesis and said second nucleotide sequence is selected from the group consisting of:
    i) a nucleic acid molecule comprising a nucleotide sequence that encodes the polypeptide involved in polyglucan synthesis; and,
    ii) a nucleic acid molecule comprising a nucleotide sequence having an antisense sequence corresponding to the second nucleotide sequence in bi).

43. The expression vector of claim 42, wherein said antisense nucleotide sequence of said first DNA construct hybridizes under stringent conditions to the nucleotide sequence encoding the maize pullulanase polypeptide, wherein said stringent conditions comprise hybridization in 50% formamide, 1 M NaCl, 1% SDS at 37° C., and a wash in 0.1×SSC at 60° C. 65° C.

44. The expression vector of claim 42, wherein said antisense nucleotide sequence of said first DNA construct comprises at least 50 contiguous nucleotides complementary to SEQ ID NO:1.

45. The expression vector of claim 44, wherein said antisense nucleotide sequence of said first DNA construct hybridizes under stringent conditions to SEQ ID NO:1, wherein said stringent conditions comprise hybridization in 50% formamide, 1 M NaCl, 1% SDS at 37° C., and a wash in 0.1×SSC at 60° C. to 65° C.

\* \* \* \* \*

UNITED STATES PATENT AND TRADEMARK OFFICE
CERTIFICATE OF CORRECTION

PATENT NO.   : 6,639,126 B1
DATED        : October 28, 2003
INVENTOR(S)  : Sewalt et al.

It is certified that error appears in the above-identified patent and that said Letters Patent is hereby corrected as shown below:

<u>Column 104,</u>
Line 55, after "said" cancel "a".

<u>Column 107,</u>
Line 63, "tie" should read -- the --.

<u>Column 108,</u>
Line 33, "1XSDS" should read -- 1% SDS --;
Line 55, after "to" insert -- a --.

<u>Column 109,</u>
Line 17, "or" should read -- of --;
Line 43, "1 NaCl" should read -- 1M NaCl --.

<u>Column 110,</u>
Line 7, "i" should read -- a --;
Line 55, "60°C. 65°C." should read -- 60°C. to 65°C. --.

Signed and Sealed this

Thirteenth Day of January, 2004

JON W. DUDAS
*Acting Director of the United States Patent and Trademark Office*

SEQUENCE LISTING

```
<160> NUMBER OF SEQ ID NOS: 16

<210> SEQ ID NO 1
<211> LENGTH: 3261
<212> TYPE: DNA
<213> ORGANISM: Zea mays
<220> FEATURE:
<221> NAME/KEY: misc_feature
<222> LOCATION: (0)...(0)
<223> OTHER INFORMATION: Zpu1--Genbank Accession No. AF080567
<221> NAME/KEY: CDS
<222> LOCATION: (41)...(2929)

<400> SEQUENCE: 1
cccgccttct ctctccctcc gaatccaaac gcggacgcaa atg ttg ctc cac gcc         55
                                            Met Leu Leu His Ala
                                             1               5 ggt ccc tcg ttc ctg ctc gca cca cct ccg cgc ttt gcc gcc gct ccg        103
Gly Pro Ser Phe Leu Leu Ala Pro Pro Pro Arg Phe Ala Ala Ala Pro
             10                  15                  20 tcg tca gct tcg ccg agg cga tcc agg aca ccg caa tcc tcg ccg ccg        151
Ser Ser Ala Ser Pro Arg Arg Ser Arg Thr Pro Gln Ser Ser Pro Pro
         25                  30                  35 acg tcg cat ttc gcg cgc ccc gct gat ccc gtg gcc caa agg gtg cgt        199
Thr Ser His Phe Ala Arg Pro Ala Asp Pro Val Ala Gln Arg Val Arg
     40                  45                  50 ccc gtc gcg ccg agg ccc ccc atg gcg acg gcg gag gag ggc gcc agc        247
Pro Val Ala Pro Arg Pro Pro Met Ala Thr Ala Glu Glu Gly Ala Ser
```

-continued

|  |  |  |  |  |  |  |  |  |  |  |  |  |  |  |  |
|---|---|---|---|---|---|---|---|---|---|---|---|---|---|---|---|
|  |  | 55 |  |  |  | 60 |  |  |  | 65 |  |  |  |  |  |
| tct | gac | gtc | ggc | gtc | gcc | gtc | gcc | gag | tcc | gca | cag | ggg | ttc | ttg | ttg | 295 |
| Ser | Asp | Val | Gly | Val | Ala | Val | Ala | Glu | Ser | Ala | Gln | Gly | Phe | Leu | Leu |
| 70 |  |  |  | 75 |  |  |  | 80 |  |  |  | 85 |  |  |  |
| gat | gcg | agg | gct | tac | tgg | gtg | aca | aaa | tcc | ttg | att | gca | tgg | aat | atc | 343 |
| Asp | Ala | Arg | Ala | Tyr | Trp | Val | Thr | Lys | Ser | Leu | Ile | Ala | Trp | Asn | Ile |
|  |  |  | 90 |  |  |  | 95 |  |  |  | 100 |  |  |  |  |
| agt | gat | cag | aaa | act | tct | ctc | ttc | tta | tat | gca | agc | aga | aat | gct | aca | 391 |
| Ser | Asp | Gln | Lys | Thr | Ser | Leu | Phe | Leu | Tyr | Ala | Ser | Arg | Asn | Ala | Thr |
|  |  |  | 105 |  |  |  | 110 |  |  |  | 115 |  |  |  |  |
| atg | tgc | atg | tcg | agt | cag | gat | atg | aaa | ggt | tat | gat | tcc | aaa | gtt | gag | 439 |
| Met | Cys | Met | Ser | Ser | Gln | Asp | Met | Lys | Gly | Tyr | Asp | Ser | Lys | Val | Glu |
|  |  | 120 |  |  |  | 125 |  |  |  | 130 |  |  |  |  |  |
| ctg | caa | cca | gaa | aat | gat | gga | ctt | cca | tcc | agt | gtg | acc | cag | aaa | ttc | 487 |
| Leu | Gln | Pro | Glu | Asn | Asp | Gly | Leu | Pro | Ser | Ser | Val | Thr | Gln | Lys | Phe |
|  | 135 |  |  |  | 140 |  |  |  | 145 |  |  |  |  |  |  |
| cct | ttt | atc | agc | tct | tat | aga | gcc | ttc | aga | att | ccg | agc | tcc | gtt | gat | 535 |
| Pro | Phe | Ile | Ser | Ser | Tyr | Arg | Ala | Phe | Arg | Ile | Pro | Ser | Ser | Val | Asp |
| 150 |  |  |  | 155 |  |  |  | 160 |  |  |  | 165 |  |  |  |
| gtt | gcc | acc | ttg | gtg | aaa | tgt | caa | ctt | gct | gtt | gct | tca | ttt | gat | gct | 583 |
| Val | Ala | Thr | Leu | Val | Lys | Cys | Gln | Leu | Ala | Val | Ala | Ser | Phe | Asp | Ala |
|  |  |  | 170 |  |  |  | 175 |  |  |  | 180 |  |  |  |  |
| cat | ggg | aac | agg | caa | gat | gtt | act | ggg | ttg | caa | cta | cct | gga | gta | ttg | 631 |
| His | Gly | Asn | Arg | Gln | Asp | Val | Thr | Gly | Leu | Gln | Leu | Pro | Gly | Val | Leu |
|  |  | 185 |  |  |  | 190 |  |  |  | 195 |  |  |  |  |  |
| gat | gac | atg | ttc | gcc | tac | act | gga | ccg | ctt | ggt | act | att | ttt | agt | gaa | 679 |
| Asp | Asp | Met | Phe | Ala | Tyr | Thr | Gly | Pro | Leu | Gly | Thr | Ile | Phe | Ser | Glu |
|  | 200 |  |  |  | 205 |  |  |  | 210 |  |  |  |  |  |  |
| gaa | gct | gtg | agt | atg | tac | cta | tgg | gct | cct | aca | gca | cag | gat | gta | agt | 727 |
| Glu | Ala | Val | Ser | Met | Tyr | Leu | Trp | Ala | Pro | Thr | Ala | Gln | Asp | Val | Ser |
| 215 |  |  |  | 220 |  |  |  | 225 |  |  |  |  |  |  |  |
| gtg | agc | ttc | tat | gat | ggt | cca | gct | ggc | cct | tta | ctg | gaa | aca | gtt | caa | 775 |
| Val | Ser | Phe | Tyr | Asp | Gly | Pro | Ala | Gly | Pro | Leu | Leu | Glu | Thr | Val | Gln |
| 230 |  |  |  | 235 |  |  |  | 240 |  |  |  | 245 |  |  |  |
| ctc | aac | gag | tta | aat | ggt | gtt | tgg | agt | gtt | act | ggt | cca | agg | aac | tgg | 823 |
| Leu | Asn | Glu | Leu | Asn | Gly | Val | Trp | Ser | Val | Thr | Gly | Pro | Arg | Asn | Trp |
|  |  | 250 |  |  |  | 255 |  |  |  | 260 |  |  |  |  |  |
| gag | aac | cgg | tat | tat | cta | tat | gaa | gtc | aca | gta | tat | cat | caa | act | aca | 871 |
| Glu | Asn | Arg | Tyr | Tyr | Leu | Tyr | Glu | Val | Thr | Val | Tyr | His | Gln | Thr | Thr |
|  | 265 |  |  |  | 270 |  |  |  | 275 |  |  |  |  |  |  |
| gga | aac | att | gag | aaa | tgt | tta | gcc | gct | gat | cct | tat | gct | aga | ggg | ctt | 919 |
| Gly | Asn | Ile | Glu | Lys | Cys | Leu | Ala | Ala | Asp | Pro | Tyr | Ala | Arg | Gly | Leu |
|  | 280 |  |  |  | 285 |  |  |  | 290 |  |  |  |  |  |  |
| tct | gca | aat | agc | aca | cga | act | tgg | ttg | gtt | gat | att | aat | aat | gaa | aca | 967 |
| Ser | Ala | Asn | Ser | Thr | Arg | Thr | Trp | Leu | Val | Asp | Ile | Asn | Asn | Glu | Thr |
| 295 |  |  |  | 300 |  |  |  | 305 |  |  |  |  |  |  |  |
| tta | aag | cca | ctt | gcc | tgg | gat | gga | ttg | gcg | gct | gaa | aag | cca | agg | ctt | 1015 |
| Leu | Lys | Pro | Leu | Ala | Trp | Asp | Gly | Leu | Ala | Ala | Glu | Lys | Pro | Arg | Leu |
| 310 |  |  |  | 315 |  |  |  | 320 |  |  |  | 325 |  |  |  |
| gat | tcc | ttc | tct | gac | ata | agc | ata | tat | gaa | ttg | cac | att | cgt | gat | ttc | 1063 |
| Asp | Ser | Phe | Ser | Asp | Ile | Ser | Ile | Tyr | Glu | Leu | His | Ile | Arg | Asp | Phe |
|  |  | 330 |  |  |  | 335 |  |  |  | 340 |  |  |  |  |  |
| agt | gcc | cat | gat | agc | aca | gtg | gac | tgt | cct | ttc | cga | gga | ggt | ttc | tgt | 1111 |
| Ser | Ala | His | Asp | Ser | Thr | Val | Asp | Cys | Pro | Phe | Arg | Gly | Gly | Phe | Cys |
|  | 345 |  |  |  | 350 |  |  |  | 355 |  |  |  |  |  |  |
| gca | ttt | aca | ttt | cag | gat | tct | gta | ggc | ata | gaa | cac | cta | aag | aaa | cta | 1159 |
| Ala | Phe | Thr | Phe | Gln | Asp | Ser | Val | Gly | Ile | Glu | His | Leu | Lys | Lys | Leu |
|  | 360 |  |  |  | 365 |  |  |  | 370 |  |  |  |  |  |  |
| tct | gat | gcc | ggt | ttg | act | cat | gtc | cat | ttg | ttg | cca | agc | ttt | caa | ttt | 1207 |

```
Ser Asp Ala Gly Leu Thr His Val His Leu Leu Pro Ser Phe Gln Phe
    375                 380                 385 ggt ggt gtt gat gac ata aag agc aat tgg aaa tgt gtt gat gag att    1255
Gly Gly Val Asp Asp Ile Lys Ser Asn Trp Lys Cys Val Asp Glu Ile
390                 395                 400                 405 gaa ctg tca aaa ctc cct cca ggg tca gat ttg caa caa gct gca att    1303
Glu Leu Ser Lys Leu Pro Pro Gly Ser Asp Leu Gln Gln Ala Ala Ile
                410                 415                 420 gtg gct att cag gaa gag gac cct tat aat tgg ggg tat aac cct gtg    1351
Val Ala Ile Gln Glu Glu Asp Pro Tyr Asn Trp Gly Tyr Asn Pro Val
            425                 430                 435 gtt tgg ggc gtt cca aaa gga agc tat gca agt aac cca gat ggt cca    1399
Val Trp Gly Val Pro Lys Gly Ser Tyr Ala Ser Asn Pro Asp Gly Pro
        440                 445                 450 agt cgt atc att gag tac cgg ctg atg gtg cag gcc ttg aat cgc tta    1447
Ser Arg Ile Ile Glu Tyr Arg Leu Met Val Gln Ala Leu Asn Arg Leu
455                 460                 465 ggt ctt cga gtt gtc atg gat gtt gta tac aat cat cta tac tca agt    1495
Gly Leu Arg Val Val Met Asp Val Val Tyr Asn His Leu Tyr Ser Ser
470                 475                 480                 485 ggc cct ttt gcc atc act tcc gtg ctt gac aag att gta cct gga tac    1543
Gly Pro Phe Ala Ile Thr Ser Val Leu Asp Lys Ile Val Pro Gly Tyr
                490                 495                 500 tac ctc aga agg gac tct aat ggt cag act gag aac agc gcg gct gtg    1591
Tyr Leu Arg Arg Asp Ser Asn Gly Gln Thr Glu Asn Ser Ala Ala Val
            505                 510                 515 aac aat aca gca agt gag cat ttc atg gtt gat aga tta atc gtg gac    1639
Asn Asn Thr Ala Ser Glu His Phe Met Val Asp Arg Leu Ile Val Asp
        520                 525                 530 gac ctt ctg aat tgg gca gta aat tac aaa gtt gac ggg ttc aga ttt    1687
Asp Leu Leu Asn Trp Ala Val Asn Tyr Lys Val Asp Gly Phe Arg Phe
535                 540                 545 gat cta atg gga cat atc atg aaa aag aca atg att aga gca aaa tcg    1735
Asp Leu Met Gly His Ile Met Lys Lys Thr Met Ile Arg Ala Lys Ser
550                 555                 560                 565 gct ctt caa agc ctt aca att gat gaa cat gga gta gat ggt tca aag    1783
Ala Leu Gln Ser Leu Thr Ile Asp Glu His Gly Val Asp Gly Ser Lys
                570                 575                 580 ata tac ttg tat ggt gaa gga tgg aac ttc ggt gaa gtt gcg gaa aat    1831
Ile Tyr Leu Tyr Gly Glu Gly Trp Asn Phe Gly Glu Val Ala Glu Asn
            585                 590                 595 caa cgt ggg ata aat gga tcc cag cta aat atg agt ggc act ggg att    1879
Gln Arg Gly Ile Asn Gly Ser Gln Leu Asn Met Ser Gly Thr Gly Ile
        600                 605                 610 ggt agt ttc aac gat aga atc cgt gat gct ata aat ggt ggc agt ccg    1927
Gly Ser Phe Asn Asp Arg Ile Arg Asp Ala Ile Asn Gly Gly Ser Pro
615                 620                 625 ttt ggg aat cca ctg caa caa ggt ttc tct act gga ttg ttc tta gag    1975
Phe Gly Asn Pro Leu Gln Gln Gly Phe Ser Thr Gly Leu Phe Leu Glu
630                 635                 640                 645 cca aat gga ttt tat cag ggc aat gaa aca gag aca agg ctc acg ctt    2023
Pro Asn Gly Phe Tyr Gln Gly Asn Glu Thr Glu Thr Arg Leu Thr Leu
                650                 655                 660 gct aca tac gct gac cat ata cag att gga tta gct ggc aat ttg aag    2071
Ala Thr Tyr Ala Asp His Ile Gln Ile Gly Leu Ala Gly Asn Leu Lys
            665                 670                 675 gac tat gta gtt ata tct cat act gga gaa gct aga aaa gga tct gaa    2119
Asp Tyr Val Val Ile Ser His Thr Gly Glu Ala Arg Lys Gly Ser Glu
        680                 685                 690
```

```
att cgc acc ttc gat ggc tca cca gtt ggc tat gct tca tcc cct ata        2167
Ile Arg Thr Phe Asp Gly Ser Pro Val Gly Tyr Ala Ser Ser Pro Ile
    695                 700                 705 gaa aca ata aac tac gcc tct gct cat gac aat gaa aca cta ttt gat        2215
Glu Thr Ile Asn Tyr Ala Ser Ala His Asp Asn Glu Thr Leu Phe Asp
710                 715                 720                 725 att att agt cta aag act ccg atg gac ctc tca att gac gag cga tgc        2263
Ile Ile Ser Leu Lys Thr Pro Met Asp Leu Ser Ile Asp Glu Arg Cys
                730                 735                 740 agg ata aat cat ttg tcc aca agc atg att gca tta tcc cag gga ata        2311
Arg Ile Asn His Leu Ser Thr Ser Met Ile Ala Leu Ser Gln Gly Ile
            745                 750                 755 cca ttt ttt cat gct ggt gat gag ata cta cga tct aag tcg ctt gat        2359
Pro Phe Phe His Ala Gly Asp Glu Ile Leu Arg Ser Lys Ser Leu Asp
        760                 765                 770 cga gat tca tat gac tct ggt gat tgg ttt aac aag att gat ttt acc        2407
Arg Asp Ser Tyr Asp Ser Gly Asp Trp Phe Asn Lys Ile Asp Phe Thr
    775                 780                 785 tat gaa aca aac aat tgg ggt gtt ggg ctt cca cca aga gaa aag aac        2455
Tyr Glu Thr Asn Asn Trp Gly Val Gly Leu Pro Pro Arg Glu Lys Asn
790                 795                 800                 805 gaa ggg agc tgg cct ttg atg aag cca aga ttg gag aac ccg tcg ttc        2503
Glu Gly Ser Trp Pro Leu Met Lys Pro Arg Leu Glu Asn Pro Ser Phe
                810                 815                 820 aaa cct gca aaa cat gac att att gct gcc tta gac aaa ttt att gat        2551
Lys Pro Ala Lys His Asp Ile Ile Ala Ala Leu Asp Lys Phe Ile Asp
            825                 830                 835 atc ctc aag atc aga tac tca tca cct ctc ttt cgc cta act aca gca        2599
Ile Leu Lys Ile Arg Tyr Ser Ser Pro Leu Phe Arg Leu Thr Thr Ala
        840                 845                 850 agt gat att gtg caa agg gtt cac ttt cac aac aca ggg ccc tcc ttg        2647
Ser Asp Ile Val Gln Arg Val His Phe His Asn Thr Gly Pro Ser Leu
    855                 860                 865 gtt cca gga gtt att gtc atg agc atc gaa gat gca cga aat gat agg        2695
Val Pro Gly Val Ile Val Met Ser Ile Glu Asp Ala Arg Asn Asp Arg
870                 875                 880                 885 cat gat atg gcc cag ata gat gaa aca ttc tct tgt gtc gtt aca gtc        2743
His Asp Met Ala Gln Ile Asp Glu Thr Phe Ser Cys Val Val Thr Val
                890                 895                 900 ttc aat gta tgt ccg tac gaa gtg tct ata gaa atc cct gat ctt gca        2791
Phe Asn Val Cys Pro Tyr Glu Val Ser Ile Glu Ile Pro Asp Leu Ala
            905                 910                 915 tca ctg cgg ctt cag ttg cat cca gtg cag gtg aat tca tcg gat gcg        2839
Ser Leu Arg Leu Gln Leu His Pro Val Gln Val Asn Ser Ser Asp Ala
        920                 925                 930 tta gcc agg cag tct gcg tac gac acc gcc aca ggt cga ttc acc gtg        2887
Leu Ala Arg Gln Ser Ala Tyr Asp Thr Ala Thr Gly Arg Phe Thr Val
    935                 940                 945 ccg aaa agg aca gca gca gtg ttc gtg gaa ccc agg tgc tga               2929
Pro Lys Arg Thr Ala Ala Val Phe Val Glu Pro Arg Cys  *
950                 955                 960 tggatgcctt tcgctagcga gcaagtgcat tcggcatcca agtcgaagca aacgaatgaa     2989
ataagagaag gccatcgaat aaaacgaagt atataaatag attgaataag acgttgccca     3049
agttgccaag gcacgctttg ccatatgtat gcgttgaaaa ataaataaat aaataaataa     3109
ataaataaat aaataaatga tgttatagag gtacaaaagc attggaacat ttctttatag     3169
aggtgaacca ccctattttc cagtttccat gtgtgaattg tgattagcat atgtatggaa     3229
taataatata aattaatttt atgcaaaaaa aa                                   3261
```

<210> SEQ ID NO 2
<211> LENGTH: 962
<212> TYPE: PRT
<213> ORGANISM: Zea mays

<400> SEQUENCE: 2

```
Met Leu Leu His Ala Gly Pro Ser Phe Leu Ala Pro Pro Arg
 1               5                  10                  15

Phe Ala Ala Pro Ser Ser Ala Ser Pro Arg Arg Ser Arg Thr Pro
            20                  25                  30

Gln Ser Ser Pro Pro Thr Ser His Phe Ala Arg Pro Ala Asp Pro Val
        35                  40                  45

Ala Gln Arg Val Arg Pro Val Ala Pro Arg Pro Met Ala Thr Ala
    50                  55                  60

Glu Glu Gly Ala Ser Ser Asp Val Gly Val Ala Val Ala Glu Ser Ala
65                  70                  75                  80

Gln Gly Phe Leu Leu Asp Ala Arg Ala Tyr Trp Val Thr Lys Ser Leu
                85                  90                  95

Ile Ala Trp Asn Ile Ser Asp Gln Lys Thr Ser Leu Phe Leu Tyr Ala
                100                 105                 110

Ser Arg Asn Ala Thr Met Cys Met Ser Ser Gln Asp Met Lys Gly Tyr
            115                 120                 125

Asp Ser Lys Val Glu Leu Gln Pro Glu Asn Asp Gly Leu Pro Ser Ser
130                 135                 140

Val Thr Gln Lys Phe Pro Phe Ile Ser Ser Tyr Arg Ala Phe Arg Ile
145                 150                 155                 160

Pro Ser Ser Val Asp Val Ala Thr Leu Val Lys Cys Gln Leu Ala Val
                165                 170                 175

Ala Ser Phe Asp Ala His Gly Asn Arg Gln Asp Val Thr Gly Leu Gln
            180                 185                 190

Leu Pro Gly Val Leu Asp Asp Met Phe Ala Tyr Thr Gly Pro Leu Gly
        195                 200                 205

Thr Ile Phe Ser Glu Glu Ala Val Ser Met Tyr Leu Trp Ala Pro Thr
210                 215                 220

Ala Gln Asp Val Ser Val Ser Phe Tyr Asp Gly Pro Ala Gly Pro Leu
225                 230                 235                 240

Leu Glu Thr Val Gln Leu Asn Glu Leu Asn Gly Val Trp Ser Val Thr
                245                 250                 255

Gly Pro Arg Asn Trp Glu Asn Arg Tyr Leu Tyr Glu Val Thr Val
            260                 265                 270

Tyr His Gln Thr Thr Gly Asn Ile Glu Lys Cys Leu Ala Ala Asp Pro
        275                 280                 285

Tyr Ala Arg Gly Leu Ser Ala Asn Ser Thr Arg Thr Trp Leu Val Asp
    290                 295                 300

Ile Asn Asn Glu Thr Leu Lys Pro Leu Ala Trp Asp Gly Leu Ala Ala
305                 310                 315                 320

Glu Lys Pro Arg Leu Asp Ser Phe Ser Asp Ile Ser Ile Tyr Glu Leu
                325                 330                 335

His Ile Arg Asp Phe Ser Ala His Ser Thr Val Asp Cys Pro Phe
            340                 345                 350

Arg Gly Gly Phe Cys Ala Phe Thr Phe Gln Asp Ser Val Gly Ile Glu
        355                 360                 365

His Leu Lys Lys Leu Ser Asp Ala Gly Leu Thr His Val His Leu Leu
```

```
            370             375             380
Pro Ser Phe Gln Phe Gly Gly Val Asp Asp Ile Lys Ser Asn Trp Lys
385                 390                 395                 400

Cys Val Asp Glu Ile Glu Leu Ser Lys Leu Pro Pro Gly Ser Asp Leu
                405                 410                 415

Gln Gln Ala Ala Ile Val Ala Ile Gln Glu Glu Asp Pro Tyr Asn Trp
            420                 425                 430

Gly Tyr Asn Pro Val Val Trp Gly Val Pro Lys Gly Ser Tyr Ala Ser
            435                 440                 445

Asn Pro Asp Gly Pro Ser Arg Ile Ile Glu Tyr Arg Leu Met Val Gln
            450                 455                 460

Ala Leu Asn Arg Leu Gly Leu Arg Val Val Met Asp Val Val Tyr Asn
465                 470                 475                 480

His Leu Tyr Ser Ser Gly Pro Phe Ala Ile Thr Ser Val Leu Asp Lys
                485                 490                 495

Ile Val Pro Gly Tyr Tyr Leu Arg Arg Asp Ser Asn Gly Gln Thr Glu
                500                 505                 510

Asn Ser Ala Ala Val Asn Asn Thr Ala Ser Glu His Phe Met Val Asp
            515                 520                 525

Arg Leu Ile Val Asp Asp Leu Leu Asn Trp Ala Val Asn Tyr Lys Val
            530                 535                 540

Asp Gly Phe Arg Phe Asp Leu Met Gly His Ile Met Lys Lys Thr Met
545                 550                 555                 560

Ile Arg Ala Lys Ser Ala Leu Gln Ser Leu Thr Ile Asp Glu His Gly
                565                 570                 575

Val Asp Gly Ser Lys Ile Tyr Leu Tyr Gly Glu Gly Trp Asn Phe Gly
                580                 585                 590

Glu Val Ala Glu Asn Gln Arg Gly Ile Asn Gly Ser Gln Leu Asn Met
            595                 600                 605

Ser Gly Thr Gly Ile Gly Ser Phe Asn Asp Arg Ile Arg Asp Ala Ile
            610                 615                 620

Asn Gly Gly Ser Pro Phe Gly Asn Pro Leu Gln Gln Gly Phe Ser Thr
625                 630                 635                 640

Gly Leu Phe Leu Glu Pro Asn Gly Phe Tyr Gln Gly Asn Glu Thr Glu
                645                 650                 655

Thr Arg Leu Thr Leu Ala Thr Tyr Ala Asp His Ile Gln Ile Gly Leu
            660                 665                 670

Ala Gly Asn Leu Lys Asp Tyr Val Val Ile Ser His Thr Gly Glu Ala
            675                 680                 685

Arg Lys Gly Ser Glu Ile Arg Thr Phe Asp Gly Ser Pro Val Gly Tyr
            690                 695                 700

Ala Ser Ser Pro Ile Glu Thr Ile Asn Tyr Ala Ser Ala His Asp Asn
705                 710                 715                 720

Glu Thr Leu Phe Asp Ile Ile Ser Leu Lys Thr Pro Met Asp Leu Ser
                725                 730                 735

Ile Asp Glu Arg Cys Arg Ile Asn His Leu Ser Thr Ser Met Ile Ala
                740                 745                 750

Leu Ser Gln Gly Ile Pro Phe Phe His Ala Gly Asp Glu Ile Leu Arg
            755                 760                 765

Ser Lys Ser Leu Asp Arg Asp Ser Tyr Asp Ser Gly Asp Trp Phe Asn
            770                 775                 780

Lys Ile Asp Phe Thr Tyr Glu Thr Asn Asn Trp Gly Val Gly Leu Pro
785                 790                 795                 800
```

-continued

```
Pro Arg Glu Lys Asn Glu Gly Ser Trp Pro Leu Met Lys Pro Arg Leu
            805                 810                 815
Glu Asn Pro Ser Phe Lys Pro Ala Lys His Asp Ile Ile Ala Ala Leu
        820                 825                 830
Asp Lys Phe Ile Asp Ile Leu Lys Ile Arg Tyr Ser Ser Pro Leu Phe
        835                 840                 845
Arg Leu Thr Thr Ala Ser Asp Ile Val Gln Arg Val His Phe His Asn
    850                 855                 860
Thr Gly Pro Ser Leu Val Pro Gly Val Ile Val Met Ser Ile Glu Asp
865                 870                 875                 880
Ala Arg Asn Asp Arg His Asp Met Ala Gln Ile Asp Glu Thr Phe Ser
                885                 890                 895
Cys Val Val Thr Val Phe Asn Val Cys Pro Tyr Glu Val Ser Ile Glu
            900                 905                 910
Ile Pro Asp Leu Ala Ser Leu Arg Leu Gln Leu His Pro Val Gln Val
        915                 920                 925
Asn Ser Ser Asp Ala Leu Ala Arg Gln Ser Ala Tyr Asp Thr Ala Thr
    930                 935                 940
Gly Arg Phe Thr Val Pro Lys Arg Thr Ala Ala Val Phe Val Glu Pro
945                 950                 955                 960
Arg Cys
```

```
<210> SEQ ID NO 3
<211> LENGTH: 1818
<212> TYPE: DNA
<213> ORGANISM: Zea mays
<220> FEATURE:
<221> NAME/KEY: misc_feature
<222> LOCATION: (0)...(0)
<223> OTHER INFORMATION: UDP-glucose starch glycosyl transferase --
      Genbank Accession No. 22509
<221> NAME/KEY: CDS
<222> LOCATION: (1)...(1818)

<400> SEQUENCE: 3 atg gcg gct ctg gcc acg tcg cag ctc gtc gca acg cgc gcc ggc ctg        48
Met Ala Ala Leu Ala Thr Ser Gln Leu Val Ala Thr Arg Ala Gly Leu
1               5                   10                  15 ggc gtc ccg gac gcg tcc acg ttc cgc cgc ggc gcc gcg cag ggc ctg        96
Gly Val Pro Asp Ala Ser Thr Phe Arg Arg Gly Ala Ala Gln Gly Leu
                20                  25                  30 agg ggg gcc cgg gcg tcg gcg gcg gcg gac acg ctc agc atg cgg acc       144
Arg Gly Ala Arg Ala Ser Ala Ala Ala Asp Thr Leu Ser Met Arg Thr
        35                  40                  45 agc gcg cgc gcg gcg ccc agg cac cag cag cag gcg cgc cgc ggg ggc       192
Ser Ala Arg Ala Ala Pro Arg His Gln Gln Gln Ala Arg Arg Gly Gly
    50                  55                  60 agg ttc ccg tcg ctc gtc gtg tgc gcc agc gcc ggc atg aac gtc gtc       240
Arg Phe Pro Ser Leu Val Val Cys Ala Ser Ala Gly Met Asn Val Val
65                  70                  75                  80 ttc gtc ggc gcc gag atg gcg ccg tgg agc aag acc ggc ggc ctc ggc       288
Phe Val Gly Ala Glu Met Ala Pro Trp Ser Lys Thr Gly Gly Leu Gly
                85                  90                  95 gac gtc ctc ggc ggc ctg ccg ccg gcc atg gcc gcg aac ggg cac cgt       336
Asp Val Leu Gly Gly Leu Pro Pro Ala Met Ala Ala Asn Gly His Arg
                100                 105                 110 gtc atg gtc gtc tct ccc cgc tac gac cag tac aag gac gcc tgg gac       384
Val Met Val Val Ser Pro Arg Tyr Asp Gln Tyr Lys Asp Ala Trp Asp
        115                 120                 125
```

-continued

| | |
|---|---|
| acc agc gtc gtg tcc gag atc aag atg gga gac ggg tac gag acg gtc<br>Thr Ser Val Val Ser Glu Ile Lys Met Gly Asp Gly Tyr Glu Thr Val<br>130                   135                   140 | 432 |
| agg ttc ttc cac tgc tac aag cgc gga gtg gac cgc gtg ttc gtt gac<br>Arg Phe Phe His Cys Tyr Lys Arg Gly Val Asp Arg Val Phe Val Asp<br>145                   150                   155                   160 | 480 |
| cac cca ctg ttc ctg gag agg gtt tgg gga aag acc gag gag aag atc<br>His Pro Leu Phe Leu Glu Arg Val Trp Gly Lys Thr Glu Glu Lys Ile<br>                   165                   170                   175 | 528 |
| tac ggg cct gtc gct gga acg gac tac agg gac aac cag ctg cgg ttc<br>Tyr Gly Pro Val Ala Gly Thr Asp Tyr Arg Asp Asn Gln Leu Arg Phe<br>                   180                   185                   190 | 576 |
| agc ctg cta tgc cag gca gca ctt gaa gct cca agg atc ctg agc ctc<br>Ser Leu Leu Cys Gln Ala Ala Leu Glu Ala Pro Arg Ile Leu Ser Leu<br>              195                   200                   205 | 624 |
| aac aac aac cca tac ttc tcc gga cca tac ggg gag gac gtc gtg ttc<br>Asn Asn Asn Pro Tyr Phe Ser Gly Pro Tyr Gly Glu Asp Val Val Phe<br>210                   215                   220 | 672 |
| gtc tgc aac gac tgg cac acc ggc cct ctc tcg tgc tac ctc aag agc<br>Val Cys Asn Asp Trp His Thr Gly Pro Leu Ser Cys Tyr Leu Lys Ser<br>225                   230                   235                   240 | 720 |
| aac tac cag tcc cac ggc atc tac agg gac gca aag acc gct ttc tgc<br>Asn Tyr Gln Ser His Gly Ile Tyr Arg Asp Ala Lys Thr Ala Phe Cys<br>                   245                   250                   255 | 768 |
| atc cac aac atc tcc tac cag ggc cgg ttc gcc ttc tcc gac tac ccg<br>Ile His Asn Ile Ser Tyr Gln Gly Arg Phe Ala Phe Ser Asp Tyr Pro<br>              260                   265                   270 | 816 |
| gag ctg aac ctc ccg gag aga ttc aag tcg tcc ttc gat ttc atc gac<br>Glu Leu Asn Leu Pro Glu Arg Phe Lys Ser Ser Phe Asp Phe Ile Asp<br>275                   280                   285 | 864 |
| ggc tac gag aag ccc gtg gaa ggc cgg aag atc aac tgg atg aag gcc<br>Gly Tyr Glu Lys Pro Val Glu Gly Arg Lys Ile Asn Trp Met Lys Ala<br>290                   295                   300 | 912 |
| ggg atc ctc gag gcc gac agg gtc ctc acc gtc agc ccc tac tac gcc<br>Gly Ile Leu Glu Ala Asp Arg Val Leu Thr Val Ser Pro Tyr Tyr Ala<br>305                   310                   315                   320 | 960 |
| gag gag ctc atc tcc ggc atc gcc agg ggc tgc gag ctc gac aac atc<br>Glu Glu Leu Ile Ser Gly Ile Ala Arg Gly Cys Glu Leu Asp Asn Ile<br>                   325                   330                   335 | 1008 |
| atg cgc ctc acc ggc atc acc ggc atc gtc aac ggc atg gac gtc agc<br>Met Arg Leu Thr Gly Ile Thr Gly Ile Val Asn Gly Met Asp Val Ser<br>              340                   345                   350 | 1056 |
| gag tgg gac ccc agc agg gac aag tac atc gcc gtg aag tac gac gtg<br>Glu Trp Asp Pro Ser Arg Asp Lys Tyr Ile Ala Val Lys Tyr Asp Val<br>355                   360                   365 | 1104 |
| tcg acg gcc gtg gag gcc aag gcg ctg aac aag gag gcg ctg cag gcg<br>Ser Thr Ala Val Glu Ala Lys Ala Leu Asn Lys Glu Ala Leu Gln Ala<br>370                   375                   380 | 1152 |
| gag gtc ggg ctc ccg gtg gac cgg aac atc ccg ctg gtg gcg ttc atc<br>Glu Val Gly Leu Pro Val Asp Arg Asn Ile Pro Leu Val Ala Phe Ile<br>385                   390                   395                   400 | 1200 |
| ggc agg ctg gaa gag cag aag ggc ccc gac gtc atg gcg gcc gcc atc<br>Gly Arg Leu Glu Glu Gln Lys Gly Pro Asp Val Met Ala Ala Ala Ile<br>                   405                   410                   415 | 1248 |
| ccg cag ctc atg gag atg gtg gag gac gtg cag atc gtt ctg ctg ggc<br>Pro Gln Leu Met Glu Met Val Glu Asp Val Gln Ile Val Leu Leu Gly<br>              420                   425                   430 | 1296 |
| acg ggc aag aag aag ttc gag cgc atg ctc atg agc gcc gag gag aag<br>Thr Gly Lys Lys Lys Phe Glu Arg Met Leu Met Ser Ala Glu Glu Lys | 1344 |

-continued

```
              435                 440                 445
ttc cca ggc aag gtg cgc gcc gtg gtc aag ttc aac gcg gcg ctg gcg      1392
Phe Pro Gly Lys Val Arg Ala Val Val Lys Phe Asn Ala Ala Leu Ala
    450                 455                 460 cac cac atc atg gcc ggc gcc gac gtg ctc gcc gtc acc agc cgc ttc      1440
His His Ile Met Ala Gly Ala Asp Val Leu Ala Val Thr Ser Arg Phe
465                 470                 475                 480 gag ccc tgc ggc ctc atc cag ctg cag ggg atg cga tac gga acg ccc      1488
Glu Pro Cys Gly Leu Ile Gln Leu Gln Gly Met Arg Tyr Gly Thr Pro
                485                 490                 495 tgc gcc tgc gcg tcc acc ggt gga ctc gtc gac acc atc atc gaa ggc      1536
Cys Ala Cys Ala Ser Thr Gly Gly Leu Val Asp Thr Ile Ile Glu Gly
            500                 505                 510 aag acc ggg ttc cac atg ggc cgc ctc agc gtc gac tgt aac gtc gtg      1584
Lys Thr Gly Phe His Met Gly Arg Leu Ser Val Asp Cys Asn Val Val
        515                 520                 525 gag ccg gcg gac gtc aag aag gtg gcc acc aca ttg cag cgc gcc atc      1632
Glu Pro Ala Asp Val Lys Lys Val Ala Thr Thr Leu Gln Arg Ala Ile
    530                 535                 540 aag gtg gtc ggc acg ccg gcg tac gag gag atg gtg agg aac tgc atg      1680
Lys Val Val Gly Thr Pro Ala Tyr Glu Glu Met Val Arg Asn Cys Met
545                 550                 555                 560 atc cag gat ctc tcc tgg aag ggc cct gcc aag aac tgg gag aac gtg      1728
Ile Gln Asp Leu Ser Trp Lys Gly Pro Ala Lys Asn Trp Glu Asn Val
                565                 570                 575 ctg ctc agc ctc ggg gtc gcc ggc ggc gag cca ggg gtc gaa ggc gag      1776
Leu Leu Ser Leu Gly Val Ala Gly Gly Glu Pro Gly Val Glu Gly Glu
            580                 585                 590 gag atc gcg ccg ctc gcc aag gag aac gtg gcc gcg ccc tga              1818
Glu Ile Ala Pro Leu Ala Lys Glu Asn Val Ala Ala Pro *
        595                 600                 605

<210> SEQ ID NO 4
<211> LENGTH: 604
<212> TYPE: PRT
<213> ORGANISM: Zea mays

<400> SEQUENCE: 4

Ala Ala Leu Ala Thr Ser Gln Leu Val Ala Thr Arg Ala Gly Leu Gly
 1               5                  10                  15

Val Pro Asp Ala Ser Thr Phe Arg Arg Gly Ala Ala Gln Gly Leu Arg
             20                  25                  30

Gly Ala Arg Ala Ser Ala Ala Ala Asp Thr Leu Ser Met Arg Thr Ser
         35                  40                  45

Ala Arg Ala Ala Pro Arg His Gln Gln Gln Ala Arg Arg Gly Gly Arg
     50                  55                  60

Phe Pro Ser Leu Val Val Cys Ala Ser Ala Gly Met Asn Val Val Phe
 65                  70                  75                  80

Val Gly Ala Glu Met Ala Pro Trp Ser Lys Thr Gly Gly Leu Gly Asp
                 85                  90                  95

Val Leu Gly Gly Leu Pro Pro Ala Met Ala Ala Asn Gly His Arg Val
            100                 105                 110

Met Val Val Ser Pro Arg Tyr Asp Gln Tyr Lys Asp Ala Trp Asp Thr
        115                 120                 125

Ser Val Val Ser Glu Ile Lys Met Gly Asp Gly Tyr Glu Thr Val Arg
    130                 135                 140

Phe Phe His Cys Tyr Lys Arg Gly Val Asp Arg Val Phe Val Asp His
145                 150                 155                 160
```

-continued

```
Pro Leu Phe Leu Glu Arg Val Trp Gly Lys Thr Glu Lys Ile Tyr
                165                 170                 175
Gly Pro Val Ala Gly Thr Asp Tyr Arg Asp Asn Gln Leu Arg Phe Ser
            180                 185                 190
Leu Leu Cys Gln Ala Ala Leu Glu Ala Pro Arg Ile Leu Ser Leu Asn
        195                 200                 205
Asn Asn Pro Tyr Phe Ser Gly Pro Tyr Gly Glu Asp Val Val Phe Val
    210                 215                 220
Cys Asn Asp Trp His Thr Gly Pro Leu Ser Cys Tyr Leu Lys Ser Asn
225                 230                 235                 240
Tyr Gln Ser His Gly Ile Tyr Arg Asp Ala Lys Thr Ala Phe Cys Ile
                245                 250                 255
His Asn Ile Ser Tyr Gln Gly Arg Phe Ala Phe Ser Asp Tyr Pro Glu
            260                 265                 270
Leu Asn Leu Pro Glu Arg Phe Lys Ser Ser Phe Asp Phe Ile Asp Gly
        275                 280                 285
Tyr Glu Lys Pro Val Glu Gly Arg Lys Ile Asn Trp Met Lys Ala Gly
    290                 295                 300
Ile Leu Glu Ala Asp Arg Val Leu Thr Val Ser Pro Tyr Tyr Ala Glu
305                 310                 315                 320
Glu Leu Ile Ser Gly Ile Ala Arg Gly Cys Glu Leu Asp Asn Ile Met
                325                 330                 335
Arg Leu Thr Gly Ile Thr Gly Ile Val Asn Gly Met Asp Val Ser Glu
            340                 345                 350
Trp Asp Pro Ser Arg Asp Lys Tyr Ile Ala Val Lys Tyr Asp Val Ser
        355                 360                 365
Thr Ala Val Glu Ala Lys Ala Leu Asn Lys Glu Ala Leu Gln Ala Glu
    370                 375                 380
Val Gly Leu Pro Val Asp Arg Asn Ile Pro Leu Val Ala Phe Ile Gly
385                 390                 395                 400
Arg Leu Glu Glu Gln Lys Gly Pro Asp Val Met Ala Ala Ala Ile Pro
                405                 410                 415
Gln Leu Met Glu Met Val Glu Asp Val Gln Ile Val Leu Leu Gly Thr
            420                 425                 430
Gly Lys Lys Lys Phe Glu Arg Met Leu Met Ser Ala Glu Glu Lys Phe
        435                 440                 445
Pro Gly Lys Val Arg Ala Val Lys Phe Asn Ala Ala Leu Ala His
    450                 455                 460
His Ile Met Ala Gly Ala Asp Val Leu Ala Val Thr Ser Arg Phe Glu
465                 470                 475                 480
Pro Cys Gly Leu Ile Gln Leu Gln Gly Met Arg Tyr Gly Thr Pro Cys
                485                 490                 495
Ala Cys Ala Ser Thr Gly Gly Leu Val Asp Thr Ile Ile Glu Gly Lys
            500                 505                 510
Thr Gly Phe His Met Gly Arg Leu Ser Val Asp Cys Asn Val Val Glu
        515                 520                 525
Pro Ala Asp Val Lys Lys Val Ala Thr Thr Leu Gln Arg Ala Ile Lys
    530                 535                 540
Val Val Gly Thr Pro Ala Tyr Glu Glu Met Val Arg Asn Cys Met Ile
545                 550                 555                 560
Gln Asp Leu Ser Trp Lys Gly Pro Ala Lys Asn Trp Glu Asn Val Leu
                565                 570                 575
```

```
Leu Ser Leu Gly Val Ala Gly Gly Glu Pro Gly Val Glu Gly Glu Glu
            580                 585                 590

Ile Ala Pro Leu Ala Lys Glu Asn Val Ala Ala Pro
            595                 600

<210> SEQ ID NO 5
<211> LENGTH: 2428
<212> TYPE: DNA
<213> ORGANISM: Zea mays
<220> FEATURE:
<221> NAME/KEY: misc_feature
<222> LOCATION: (0)...(0)
<223> OTHER INFORMATION: glutamine:fructose-6-phosphate amidotransferase

<400> SEQUENCE: 5
gtcttcgccg ctcccttccc ggcctccggg gctggacgaa acgaaccctc gctcgccctc      60
cttataaccg aacggccgaa cccagccaac ccagccgttt ctcttcgtac ggcctctgcc     120
agccagtgtc ctgctactag ggaagcatac caactcccca ttcttctctt cgccgcagcc     180
aggaaggaag gatgtgcggg atcttcgcct acctcaacta caacgtctcg cgggagcgcc     240
gctacatcct cgaggtcctc ttcaacggcc tccgccgcct cgagtaccgc ggctacgact     300
ccgccgggat cgcgctcgat gccgaccgcc aggtccctc ccccgctccc gcttcctctt     360
ccgacgcgcg gccgtacgcc ggggcgccgc cgctcgtgtt ccgccaggag ggcaagatcg     420
agaacctcgt gcgatccgtc tactccgagg ttgatgagaa ggatgtgaac ctggatgctg     480
cgttcagtgt gcatgctggg atcgcacata ccaggtgggc cacgcacggt gtgcctgctc     540
caaggaacag ccaccccccaa tcgtctggtg ccggtgatga gttcttggtt gtccacaatg     600
gcattatcac caactatgag gtcttgaaag agacactaac taggcacggc ttcacctttg     660
agtctgatac agacacagaa gtcatcccta agctagcaaa gttcgttttt gataaatctc     720
atgatgaaca aggtgatgtg acgtttagcc aagttgttat ggaagtcatg aggcagcttg     780
aaggagccta cgcacttatc tttaaaagcc cgcactatcc caatgaattg attgcatgca     840
aacgaggcag ccaactgata cttggtgtca acgaattgag tggtcaacag aatgggaaat     900
catttcatga tgtcaaaacc ttgacaacaa atggaaagcc caagaatta ttcttctcca     960 gtgatctatg tgctattgta gagcatacga gaaactactt agctcttgaa gataatgaaa    1020
ttgttcatat taaggatggt agtgtttcga tcctcaagtt tgaccctcac aaagagaagc    1080
cagcatctgt gcaacgagca ttgtctgttc ttgagatgga agttgagcaa ataaagaaag    1140
gaagttatga tcacttcatg caaaaagaaa tccatgaaca gccacattcg ttgaaaacaa    1200
caatgagggg tagattgaag gatggtgggg ttgttctagg tggactgaag gaatatctca    1260
agacaattag gcgctgtaga agggtggtat ttattggttg tggaacaagt tacaatgctg    1320
ccttagctgc aagaccttt gtggaagaac tgactggtat tcctgtgact atggaggttg    1380
caagtgactt gctggacaga caaggtccca tctacagaga agacactgca gttttgtta    1440 gtcaatctgg ggagacagca gataccctcc ttgctctaga ttatgcacta gaaaatggag    1500
ctctctgtgt tggcataaca aatactgttg gaagcacgct gtctagaaaa acacactgtg    1560
gggttcatat caatgctggt tgtgagattg tgttgccag tacaaaggct tatacaagtc    1620
aaatagtagc catggcgatg atggcgttgg ctattgggtc cgatcagata tctactcaag    1680
ctaggaggga cagtatcatc agtggactga acaacctttc aagcaatgtc agcgaagttc    1740
tcaagctaga tgctggaatg aaggagcttg cctcttcgct gatcgactca gagtcgctcc    1800
tcgtgttcgg aaggggttac aactacgcca ccgcgctgga gggcgccctg aaggtcaagg    1860
```

-continued

```
aggtggcgct gatgcacagc gagggcatgc tcgctggcga gatgaagcac gggccgctgg   1920
ccctcgtgga cgagaacctc cccatcattg tcattgcgac ccgcgacgcg tgcttcagca   1980
agcagcagtc ggtgatccaa cagctcctct cgcgcagggg gcgcctgata gtgatgtgct   2040
ctagggagga tgccgcggct gtgtgcccta gcggtgggtc gtgcagagtc attgaagttc   2100
cacaggttgc agactgtctc cagccagtga tcaacataat tccattacag ttgctcgcgt   2160
accatctgac tgttctccgg ggattcgacg tggaccaacc aaggaatctg gcgaagagcg   2220
tgaccacgca gtagggagag gtagatgaga tgtttgtatt gtagttaatt gtccttgctc   2280
ttgaggtggc tagtacgtag cataaatatt atggtgcgtt aaacttgttg ttttgtgaac   2340
gaaatgtacc tctctttttt taattatggt atattggtgt caatagcaaa aaaaaaaaa   2400 aaaaaaaaaa aaaaaaaaaa aaaaaaaa                                       2428
```

<210> SEQ ID NO 6
<211> LENGTH: 680
<212> TYPE: PRT
<213> ORGANISM: Zea mays

<400> SEQUENCE: 6

Met Cys Gly Ile Phe Ala Tyr Leu Asn Tyr Asn Val Ser Arg Glu Arg
1               5                   10                  15

Arg Tyr Ile Leu Glu Val Leu Phe Asn Gly Leu Arg Arg Leu Glu Tyr
            20                  25                  30

Arg Gly Tyr Asp Ser Ala Gly Ile Ala Leu Asp Ala Asp Arg Gln Val
        35                  40                  45

Pro Ser Pro Ala Pro Ala Ser Ser Asp Ala Arg Pro Tyr Ala Gly
    50                  55                  60

Ala Pro Pro Leu Val Phe Arg Gln Glu Gly Lys Ile Glu Asn Leu Val
65                  70                  75                  80

Arg Ser Val Tyr Ser Glu Val Asp Glu Lys Asp Val Asn Leu Asp Ala
                85                  90                  95

Ala Phe Ser Val His Ala Gly Ile Ala His Thr Arg Trp Ala Thr His
            100                 105                 110

Gly Val Pro Ala Pro Arg Asn Ser His Pro Gln Ser Ser Gly Ala Gly
        115                 120                 125

Asp Glu Phe Leu Val Val His Asn Gly Ile Ile Thr Asn Tyr Glu Val
    130                 135                 140

Leu Lys Glu Thr Leu Thr Arg His Gly Phe Thr Phe Glu Ser Asp Thr
145                 150                 155                 160

Asp Thr Glu Val Ile Pro Lys Leu Ala Lys Phe Val Phe Asp Lys Ser
                165                 170                 175

His Asp Glu Gln Gly Asp Val Thr Phe Ser Gln Val Val Met Glu Val
            180                 185                 190

Met Arg Gln Leu Glu Gly Ala Tyr Ala Leu Ile Phe Lys Ser Pro His
        195                 200                 205

Tyr Pro Asn Glu Leu Ile Ala Cys Lys Arg Gly Ser Gln Leu Ile Leu
    210                 215                 220

Gly Val Asn Glu Leu Ser Gly Gln Gln Asn Gly Lys Ser Phe His Asp
225                 230                 235                 240

Val Lys Thr Leu Thr Thr Asn Gly Lys Pro Lys Glu Leu Phe Phe Ser
                245                 250                 255

Ser Asp Leu Cys Ala Ile Val Glu His Thr Lys Asn Tyr Leu Ala Leu
            260                 265                 270
```

-continued

```
Glu Asp Asn Glu Ile Val His Ile Lys Asp Gly Ser Val Ser Ile Leu
            275                 280                 285

Lys Phe Asp Pro His Lys Glu Lys Pro Ala Ser Val Gln Arg Ala Leu
    290                 295                 300

Ser Val Leu Glu Met Glu Val Glu Gln Ile Lys Lys Gly Ser Tyr Asp
305                 310                 315                 320

His Phe Met Gln Lys Glu Ile His Glu Gln Pro His Ser Leu Lys Thr
                325                 330                 335

Thr Met Arg Gly Arg Leu Lys Asp Gly Val Val Leu Gly Gly Leu
                340                 345                 350

Lys Glu Tyr Leu Lys Thr Ile Arg Arg Cys Arg Arg Val Val Phe Ile
            355                 360                 365

Gly Cys Gly Thr Ser Tyr Asn Ala Ala Leu Ala Ala Arg Pro Phe Val
370                 375                 380

Glu Glu Leu Thr Gly Ile Pro Val Thr Met Glu Val Ala Ser Asp Leu
385                 390                 395                 400

Leu Asp Arg Gln Gly Pro Ile Tyr Arg Glu Asp Thr Ala Val Phe Val
                405                 410                 415

Ser Gln Ser Gly Glu Thr Ala Asp Thr Leu Leu Ala Leu Asp Tyr Ala
                420                 425                 430

Leu Glu Asn Gly Ala Leu Cys Val Gly Ile Thr Asn Thr Val Gly Ser
            435                 440                 445

Thr Leu Ser Arg Lys Thr His Cys Gly Val His Ile Asn Ala Gly Cys
    450                 455                 460

Glu Ile Gly Val Ala Ser Thr Lys Ala Tyr Thr Ser Gln Ile Val Ala
465                 470                 475                 480

Met Ala Met Met Ala Leu Ala Ile Gly Ser Asp Gln Ile Ser Thr Gln
                485                 490                 495

Ala Arg Arg Asp Ser Ile Ile Ser Gly Leu Asn Asn Leu Ser Ser Asn
                500                 505                 510

Val Ser Glu Val Leu Lys Leu Asp Ala Gly Met Lys Glu Leu Ala Ser
            515                 520                 525

Ser Leu Ile Asp Ser Glu Ser Leu Leu Val Phe Gly Arg Gly Tyr Asn
    530                 535                 540

Tyr Ala Thr Ala Leu Glu Gly Ala Leu Lys Val Lys Glu Val Ala Leu
545                 550                 555                 560

Met His Ser Glu Gly Met Leu Ala Gly Glu Met Lys His Gly Pro Leu
                565                 570                 575

Ala Leu Val Asp Glu Asn Leu Pro Ile Ile Val Ile Ala Thr Arg Asp
                580                 585                 590

Ala Cys Phe Ser Lys Gln Gln Ser Val Ile Gln Leu Leu Ser Arg
            595                 600                 605

Arg Gly Arg Leu Ile Val Met Cys Ser Arg Gly Asp Ala Ala Ala Val
    610                 615                 620

Cys Pro Ser Gly Gly Ser Cys Arg Val Ile Glu Val Pro Gln Val Ala
625                 630                 635                 640

Asp Cys Leu Gln Pro Val Ile Asn Ile Ile Pro Leu Gln Leu Leu Ala
                645                 650                 655

Tyr His Leu Thr Val Leu Arg Gly Phe Asp Val Asp Gln Pro Arg Asn
                660                 665                 670

Leu Ala Lys Ser Val Thr Thr Gln
            675                 680
```

-continued

```
<210> SEQ ID NO 7
<211> LENGTH: 2373
<212> TYPE: DNA
<213> ORGANISM: Homo sapiens
<220> FEATURE:
<221> NAME/KEY: misc_feature
<222> LOCATION: (0)...(0)
<223> OTHER INFORMATION: liver glycogen synthase
<223> OTHER INFORMATION: Genbank Accession No. D29685
<221> NAME/KEY: CDS
<222> LOCATION: (255)...(2369)

<400> SEQUENCE: 7
agatactgac agggcagata ccgtcctcac aatacctgcc cagaaagacg agaaagagga       60
ggaagaattc ctccttccac caggaattct gtgggaagca cataagattt catgctacta     120
gtttattccc aagagaagct accaaagcct ggtaactcta ccaactctaa cttttgtgcc     180
tgtaagttct cttctcctgg gattacaact aattgaaaca ggaatcaaag gagtctcggt     240
ggactgtaag aaga atg ctt cga ggc cga tcc ctc tct gta aca tcc ctg        290
              Met Leu Arg Gly Arg Ser Leu Ser Val Thr Ser Leu
                1               5                  10 ggt ggg ctt ccc cag tgg gaa gtc gaa gaa ctt cct gtg gag gag tta        338
Gly Gly Leu Pro Gln Trp Glu Val Glu Glu Leu Pro Val Glu Glu Leu
            15                  20                  25 ctg ctc ttt gaa gtt gct tgg gaa gtg acc aat aaa gtt gga ggc atc        386
Leu Leu Phe Glu Val Ala Trp Glu Val Thr Asn Lys Val Gly Gly Ile
        30                  35                  40 tat act gtg att cag aca aag gcc aaa aca aca gca gat gaa tgg gga        434
Tyr Thr Val Ile Gln Thr Lys Ala Lys Thr Thr Ala Asp Glu Trp Gly
 45                  50                  55                  60 gag aac tat ttt ctg ata ggt cca tat ttt gag cat aat atg aag act        482
Glu Asn Tyr Phe Leu Ile Gly Pro Tyr Phe Glu His Asn Met Lys Thr
                 65                  70                  75 cag gtg gaa cag tgt gaa cct gta aat gat gct gtc aga aga gca gtg        530
Gln Val Glu Gln Cys Glu Pro Val Asn Asp Ala Val Arg Arg Ala Val
             80                  85                  90 gac gca atg aat atg cat ggc tgc cag gtg cat ttt gga aga tgg ctg        578
Asp Ala Met Asn Met His Gly Cys Gln Val His Phe Gly Arg Trp Leu
         95                 100                 105 ata gaa gga agt cct tat gtg gta ctt ttt gac ata ggc tat tca gct        626
Ile Glu Gly Ser Pro Tyr Val Val Leu Phe Asp Ile Gly Tyr Ser Ala
    110                 115                 120 tgg aat ctg gac agg tgg aag ggt gac ctc tgg gaa gca tgc agt gtc        674
Trp Asn Leu Asp Arg Trp Lys Gly Asp Leu Trp Glu Ala Cys Ser Val
125                 130                 135                 140 ggc att cct tat cat gac cga gaa gcc aat gat atg ctg ata ttt gga        722
Gly Ile Pro Tyr His Asp Arg Glu Ala Asn Asp Met Leu Ile Phe Gly
                145                 150                 155 tct tta act gcc tgg ttc tta aaa gaa gtg aca gat cat gca gat ggt        770
Ser Leu Thr Ala Trp Phe Leu Lys Glu Val Thr Asp His Ala Asp Gly
            160                 165                 170 aaa tat gtc gtt gcc cgg ttc cat gaa tgg cag gct gga gtt gga ctg        818
Lys Tyr Val Val Ala Arg Phe His Glu Trp Gln Ala Gly Val Gly Leu
        175                 180                 185 atc ctt tct cga gcc agg aaa ctt cct att gcc aca ata ttt aca acc        866
Ile Leu Ser Arg Ala Arg Lys Leu Pro Ile Ala Thr Ile Phe Thr Thr
    190                 195                 200 cac gct aca cta ctt ggg agg tat ctc tgt gca gca aat att gat ttc        914
His Ala Thr Leu Leu Gly Arg Tyr Leu Cys Ala Ala Asn Ile Asp Phe
205                 210                 215                 220
```

```
tac aac cat ctt gat aag ttt aac att gac aaa gag gct ggg gaa agg      962
Tyr Asn His Leu Asp Lys Phe Asn Ile Asp Lys Glu Ala Gly Glu Arg
                225                 230                 235 cag att tac cac cgg tac tgc atg gag cga gct tcc gtt cat tgc gct     1010
Gln Ile Tyr His Arg Tyr Cys Met Glu Arg Ala Ser Val His Cys Ala
                240                 245                 250 cac gtg ttc acc acg gtt tct gaa ata aca gca ata gaa gct gaa cat     1058
His Val Phe Thr Thr Val Ser Glu Ile Thr Ala Ile Glu Ala Glu His
            255                 260                 265 atg ctg aag aga aag cct gat gta gtt act cca aac ggc ttg aat gtt     1106
Met Leu Lys Arg Lys Pro Asp Val Val Thr Pro Asn Gly Leu Asn Val
            270                 275                 280 aag aaa ttt tca gca gtg cat gag ttt caa aat cta cat gcc atg tac     1154
Lys Lys Phe Ser Ala Val His Glu Phe Gln Asn Leu His Ala Met Tyr
285                 290                 295                 300 aag gcc aga atc caa gat ttt gtt cga ggt cat ttc tat ggt cat ctc     1202
Lys Ala Arg Ile Gln Asp Phe Val Arg Gly His Phe Tyr Gly His Leu
                305                 310                 315 gac ttt gat ctt gaa aag act ttg ttc ctt ttc att gct ggg agg tat     1250
Asp Phe Asp Leu Glu Lys Thr Leu Phe Leu Phe Ile Ala Gly Arg Tyr
                320                 325                 330 gag ttt ttc aaa aca aaa gga gct gac atc ttc cta gat tcc tta tcc     1298
Glu Phe Phe Lys Thr Lys Gly Ala Asp Ile Phe Leu Asp Ser Leu Ser
                335                 340                 345 agg cta aat ttc ctg ctg agg atg cat aaa agt gac atc aca gtg gtg     1346
Arg Leu Asn Phe Leu Leu Arg Met His Lys Ser Asp Ile Thr Val Val
            350                 355                 360 gtg ttt ttc att atg cct gcc aag aca aat aat ttc aac gtg gaa acc     1394
Val Phe Phe Ile Met Pro Ala Lys Thr Asn Asn Phe Asn Val Glu Thr
365                 370                 375                 380 ctg aaa gga caa gca gtg cga aaa cag ctg tgg gat gtt gca cat tct     1442
Leu Lys Gly Gln Ala Val Arg Lys Gln Leu Trp Asp Val Ala His Ser
                385                 390                 395 gtg aag gaa aag ttt gga aaa aaa ctc tat gat gca tta tta aga gga     1490
Val Lys Glu Lys Phe Gly Lys Lys Leu Tyr Asp Ala Leu Leu Arg Gly
                400                 405                 410 gaa att cct gac ctg aac gat att tta gat cga gat gat cta aca att     1538
Glu Ile Pro Asp Leu Asn Asp Ile Leu Asp Arg Asp Asp Leu Thr Ile
                415                 420                 425 atg aaa aga gcc atc ttt tca act cag cga cag tca tta gcc cca gtg     1586
Met Lys Arg Ala Ile Phe Ser Thr Gln Arg Gln Ser Leu Ala Pro Val
430                 435                 440 acc acg cac aac atg att gat gac tcc acc gac ccc atc ctc agc acc     1634
Thr Thr His Asn Met Ile Asp Asp Ser Thr Asp Pro Ile Leu Ser Thr
445                 450                 455                 460 att aga cgg att gga ctt ttc aac aac cgc aca gat aga gtc aag gtg     1682
Ile Arg Arg Ile Gly Leu Phe Asn Asn Arg Thr Asp Arg Val Lys Val
                465                 470                 475 att ttg cac cca gag ttt cta tcc tcc acc agt ccc tta cta ccc atg     1730
Ile Leu His Pro Glu Phe Leu Ser Ser Thr Ser Pro Leu Leu Pro Met
            480                 485                 490 gac tat gaa gag ttt gtt aga ggt tgt cat ctt gga gta ttt cca tca     1778
Asp Tyr Glu Glu Phe Val Arg Gly Cys His Leu Gly Val Phe Pro Ser
            495                 500                 505 tac tat gaa ccc tgg ggt tat act cca gct gaa tgc act gtg atg ggt     1826
Tyr Tyr Glu Pro Trp Gly Tyr Thr Pro Ala Glu Cys Thr Val Met Gly
            510                 515                 520 atc ccc agt gtg acc acg aat ctc tcc ggg ttt ggc tgt ttc atg cag     1874
Ile Pro Ser Val Thr Thr Asn Leu Ser Gly Phe Gly Cys Phe Met Gln
```

```
                525                 530                 535                 540
gag cac gtg gct gat cct act gct tac ggt att tac atc gtt gac agg         1922
Glu His Val Ala Asp Pro Thr Ala Tyr Gly Ile Tyr Ile Val Asp Arg
                    545                 550                 555 cgg ttc cgt tct cca gat gat tct tgc aat cag ctg act aag ttt ctc         1970
Arg Phe Arg Ser Pro Asp Asp Ser Cys Asn Gln Leu Thr Lys Phe Leu
                560                 565                 570 tat gga ttt tgc aac atg tca cgc cgc caa agg ttt atc cag agg aac         2018
Tyr Gly Phe Cys Asn Met Ser Arg Arg Gln Arg Phe Ile Gln Arg Asn
                575                 580                 585 aga act gag agg ctc tca gat ctt ctg gat tgg aga tac tta ggc aga         2066
Arg Thr Glu Arg Leu Ser Asp Leu Leu Asp Trp Arg Tyr Leu Gly Arg
                590                 595                 600 tat tac cag cat gcc aga cac ctg aca tta agc aga gct ttt cca gat         2114
Tyr Tyr Gln His Ala Arg His Leu Thr Leu Ser Arg Ala Phe Pro Asp
605                 610                 615                 620 aaa ttc cat gtg gaa cta aca tca cca cca acg aca gaa gga ttt aaa         2162
Lys Phe His Val Glu Leu Thr Ser Pro Pro Thr Thr Glu Gly Phe Lys
                    625                 630                 635 tat ccc agg cct tcc tca gta cca cct tct cct tca ggg tct cag gcc         2210
Tyr Pro Arg Pro Ser Ser Val Pro Pro Ser Pro Ser Gly Ser Gln Ala
                640                 645                 650 tcc agt cct cag agc agt gat gtg gaa gat gaa gtg gag gat gag aga         2258
Ser Ser Pro Gln Ser Ser Asp Val Glu Asp Glu Val Glu Asp Glu Arg
                655                 660                 665 tac gat gag gaa gag gag gct gaa agg gat cgg tta aat atc aag tca         2306
Tyr Asp Glu Glu Glu Glu Ala Glu Arg Asp Arg Leu Asn Ile Lys Ser
                670                 675                 680 cca ttt tca ctg agc cac gtt cct cat ggg aag aaa aag ctg cat ggt         2354
Pro Phe Ser Leu Ser His Val Pro His Gly Lys Lys Lys Leu His Gly
685                 690                 695                 700 gaa tat aag aac tga attc                                                 2373
Glu Tyr Lys Asn *
```

<210> SEQ ID NO 8
<211> LENGTH: 704
<212> TYPE: PRT
<213> ORGANISM: Homo sapiens

<400> SEQUENCE: 8

```
Met Leu Arg Gly Arg Ser Leu Ser Val Thr Ser Leu Gly Gly Leu Pro
1               5                   10                  15

Gln Trp Glu Val Glu Glu Leu Pro Val Glu Glu Leu Leu Leu Phe Glu
                20                  25                  30

Val Ala Trp Glu Val Thr Asn Lys Val Gly Gly Ile Tyr Thr Val Ile
                35                  40                  45

Gln Thr Lys Ala Lys Thr Thr Ala Asp Glu Trp Gly Glu Asn Tyr Phe
        50                  55                  60

Leu Ile Gly Pro Tyr Phe Glu His Asn Met Lys Thr Gln Val Glu Gln
65                  70                  75                  80

Cys Glu Pro Val Asn Asp Ala Val Arg Arg Ala Val Asp Ala Met Asn
                85                  90                  95

Met His Gly Cys Gln Val His Phe Gly Arg Trp Leu Ile Glu Gly Ser
                100                 105                 110

Pro Tyr Val Val Leu Phe Asp Ile Gly Tyr Ser Ala Trp Asn Leu Asp
            115                 120                 125

Arg Trp Lys Gly Asp Leu Trp Glu Ala Cys Ser Val Gly Ile Pro Tyr
        130                 135                 140
```

-continued

```
His Asp Arg Glu Ala Asn Asp Met Leu Ile Phe Gly Ser Leu Thr Ala
145                 150                 155                 160

Trp Phe Leu Lys Glu Val Thr Asp His Ala Asp Gly Lys Tyr Val Val
            165                 170                 175

Ala Arg Phe His Glu Trp Gln Ala Gly Val Gly Leu Ile Leu Ser Arg
        180                 185                 190

Ala Arg Lys Leu Pro Ile Ala Thr Ile Phe Thr Thr His Ala Thr Leu
    195                 200                 205

Leu Gly Arg Tyr Leu Cys Ala Ala Asn Ile Asp Phe Tyr Asn His Leu
210                 215                 220

Asp Lys Phe Asn Ile Asp Lys Glu Ala Gly Glu Arg Gln Ile Tyr His
225                 230                 235                 240

Arg Tyr Cys Met Glu Arg Ala Ser Val His Cys Ala His Val Phe Thr
                245                 250                 255

Thr Val Ser Glu Ile Thr Ala Ile Glu Ala Glu His Met Leu Lys Arg
            260                 265                 270

Lys Pro Asp Val Val Thr Pro Asn Gly Leu Asn Val Lys Lys Phe Ser
        275                 280                 285

Ala Val His Glu Phe Gln Asn Leu His Ala Met Tyr Lys Ala Arg Ile
    290                 295                 300

Gln Asp Phe Val Arg Gly His Phe Tyr Gly His Leu Asp Phe Asp Leu
305                 310                 315                 320

Glu Lys Thr Leu Phe Leu Phe Ile Ala Gly Arg Tyr Glu Phe Phe Lys
                325                 330                 335

Thr Lys Gly Ala Asp Ile Phe Leu Asp Ser Leu Ser Arg Leu Asn Phe
            340                 345                 350

Leu Leu Arg Met His Lys Ser Asp Ile Thr Val Val Phe Phe Ile
        355                 360                 365

Met Pro Ala Lys Thr Asn Asn Phe Asn Val Glu Thr Leu Lys Gly Gln
    370                 375                 380

Ala Val Arg Lys Gln Leu Trp Asp Val Ala His Ser Val Lys Glu Lys
385                 390                 395                 400

Phe Gly Lys Lys Leu Tyr Asp Ala Leu Leu Arg Gly Glu Ile Pro Asp
                405                 410                 415

Leu Asn Asp Ile Leu Asp Arg Asp Leu Thr Ile Met Lys Arg Ala
            420                 425                 430

Ile Phe Ser Thr Gln Arg Gln Ser Leu Ala Pro Val Thr Thr His Asn
        435                 440                 445

Met Ile Asp Asp Ser Thr Asp Pro Ile Leu Ser Thr Ile Arg Arg Ile
    450                 455                 460

Gly Leu Phe Asn Asn Arg Thr Asp Arg Val Lys Val Ile Leu His Pro
465                 470                 475                 480

Glu Phe Leu Ser Ser Thr Ser Pro Leu Leu Pro Met Asp Tyr Glu Glu
                485                 490                 495

Phe Val Arg Gly Cys His Leu Gly Val Phe Pro Ser Tyr Tyr Glu Pro
            500                 505                 510

Trp Gly Tyr Thr Pro Ala Glu Cys Thr Val Met Gly Ile Pro Ser Val
        515                 520                 525

Thr Thr Asn Leu Ser Gly Phe Gly Cys Phe Met Gln Glu His Val Ala
    530                 535                 540

Asp Pro Thr Ala Tyr Gly Ile Tyr Ile Val Asp Arg Arg Phe Arg Ser
545                 550                 555                 560
```

-continued

```
Pro Asp Asp Ser Cys Asn Gln Leu Thr Lys Phe Leu Tyr Gly Phe Cys
            565                 570                 575

Asn Met Ser Arg Arg Gln Arg Phe Ile Gln Arg Asn Arg Thr Glu Arg
        580                 585                 590

Leu Ser Asp Leu Leu Asp Trp Arg Tyr Leu Gly Arg Tyr Tyr Gln His
            595                 600                 605

Ala Arg His Leu Thr Leu Ser Arg Ala Phe Pro Asp Lys Phe His Val
        610                 615                 620

Glu Leu Thr Ser Pro Pro Thr Thr Glu Gly Phe Lys Tyr Pro Arg Pro
625                 630                 635                 640

Ser Ser Val Pro Pro Ser Pro Ser Gly Ser Gln Ala Ser Ser Pro Gln
                645                 650                 655

Ser Ser Asp Val Glu Asp Glu Val Glu Asp Glu Arg Tyr Asp Glu Glu
            660                 665                 670

Glu Glu Ala Glu Arg Asp Arg Leu Asn Ile Lys Ser Pro Phe Ser Leu
        675                 680                 685

Ser His Val Pro His Gly Lys Lys Leu His Gly Glu Tyr Lys Asn
            690                 695                 700
```

<210> SEQ ID NO 9
<211> LENGTH: 2446
<212> TYPE: DNA
<213> ORGANISM: Zea mays
<220> FEATURE:
<221> NAME/KEY: misc_feature
<222> LOCATION: (0)...(0)
<223> OTHER INFORMATION: SBEIIa
<223> OTHER INFORMATION: Genbank Accession No. U65948
<221> NAME/KEY: CDS
<222> LOCATION: (2)...(2446)

<400> SEQUENCE: 9

```
g gac ttg ccg tcg gtg ctc ttc agg agg aag gac gct ttc tct cgc acc        49
  Asp Leu Pro Ser Val Leu Phe Arg Arg Lys Asp Ala Phe Ser Arg Thr
   1               5                  10                  15 gtt ctg agc tgc gct ggt gct cct gga aag gta ctg gtg cct gga ggt        97
Val Leu Ser Cys Ala Gly Ala Pro Gly Lys Val Leu Val Pro Gly Gly
            20                  25                  30 ggc agt gat gac ttg ctt tcc tcc gca gag ccg gtc gtg gac act caa       145
Gly Ser Asp Asp Leu Leu Ser Ser Ala Glu Pro Val Val Asp Thr Gln
        35                  40                  45 cct gaa gaa cta cag ata cct gaa gca gaa ctg act gtg gag aag aca       193
Pro Glu Glu Leu Gln Ile Pro Glu Ala Glu Leu Thr Val Glu Lys Thr
    50                  55                  60 tcc tcc tca cca act caa aca aca tca gca gtg gct gaa gca agc tca       241
Ser Ser Ser Pro Thr Gln Thr Thr Ser Ala Val Ala Glu Ala Ser Ser
 65                  70                  75                  80 gga gtt gag gct gag gag agg cct gag ctc tca gaa gtg att gga gtt       289
Gly Val Glu Ala Glu Glu Arg Pro Glu Leu Ser Glu Val Ile Gly Val
                85                  90                  95 gga ggt act ggt gga acc aaa att gat ggt gca ggc atc aaa gcc aaa       337
Gly Gly Thr Gly Gly Thr Lys Ile Asp Gly Ala Gly Ile Lys Ala Lys
            100                 105                 110 gca cca ctc gtg gag gag aaa cca cga gtt atc cca cca cca gga gat       385
Ala Pro Leu Val Glu Glu Lys Pro Arg Val Ile Pro Pro Pro Gly Asp
        115                 120                 125 ggc caa cga ata tat gag att gac cca atg ttg gaa ggg ttt cgg ggt       433
Gly Gln Arg Ile Tyr Glu Ile Asp Pro Met Leu Glu Gly Phe Arg Gly
    130                 135                 140 cac ctt gac tac cga tac agt gaa tat aag aga tta cgt gcg gct att       481
```

-continued

```
                His Leu Asp Tyr Arg Tyr Ser Glu Tyr Lys Arg Leu Arg Ala Ala Ile
                145                 150                 155                 160 gat caa cat gaa ggt ggt ttg gat gca ttt tca cgc ggt tac gaa aag            529
Asp Gln His Glu Gly Gly Leu Asp Ala Phe Ser Arg Gly Tyr Glu Lys
                165                 170                 175 ctt gga ttt act cgc agc gct gaa ggt atc act tac aga gaa tgg gct            577
Leu Gly Phe Thr Arg Ser Ala Glu Gly Ile Thr Tyr Arg Glu Trp Ala
            180                 185                 190 cct gga gca tac tct gca gca tta gta ggt gac ttc aac aac tgg aac            625
Pro Gly Ala Tyr Ser Ala Ala Leu Val Gly Asp Phe Asn Asn Trp Asn
            195                 200                 205 cca aat gct gat gct atg gcc aga aat gag tac ggc gtt tgg gag att            673
Pro Asn Ala Asp Ala Met Ala Arg Asn Glu Tyr Gly Val Trp Glu Ile
            210                 215                 220 ttc ctg cct aac aat gct gat ggt tcc cct gct att cct cat ggc tca            721
Phe Leu Pro Asn Asn Ala Asp Gly Ser Pro Ala Ile Pro His Gly Ser
225                 230                 235                 240 cgt gta aag ata cgg atg gac aca cca tct ggt gtt aag gat tcc att            769
Arg Val Lys Ile Arg Met Asp Thr Pro Ser Gly Val Lys Asp Ser Ile
                245                 250                 255 cct gcc tgg atc aag ttt tct gtg cag gct cca ggt gaa ata cca tac            817
Pro Ala Trp Ile Lys Phe Ser Val Gln Ala Pro Gly Glu Ile Pro Tyr
            260                 265                 270 aac ggt ata tat tat gac cca cct gaa gag gag aaa tat gta ttc aaa            865
Asn Gly Ile Tyr Tyr Asp Pro Pro Glu Glu Glu Lys Tyr Val Phe Lys
            275                 280                 285 cac cct caa cct aag cgg ccc aag tca ctg cgg ata tat gaa tca cat            913
His Pro Gln Pro Lys Arg Pro Lys Ser Leu Arg Ile Tyr Glu Ser His
            290                 295                 300 gtt gga atg agt agc ccg gaa cca aag ata aat aca tat gct aac ttc            961
Val Gly Met Ser Ser Pro Glu Pro Lys Ile Asn Thr Tyr Ala Asn Phe
305                 310                 315                 320 aga gat gag gtg ctt cca aga att aaa aag ctt gga tac aat gca gta           1009
Arg Asp Glu Val Leu Pro Arg Ile Lys Lys Leu Gly Tyr Asn Ala Val
                325                 330                 335 cag ata atg gca atc cag gaa cac tct tat tat gca agc ttt ggg tac           1057
Gln Ile Met Ala Ile Gln Glu His Ser Tyr Tyr Ala Ser Phe Gly Tyr
            340                 345                 350 cat gtt acg aat ttt ttt gcc cca agt agc cgt ttt ggg act cca gag           1105
His Val Thr Asn Phe Phe Ala Pro Ser Ser Arg Phe Gly Thr Pro Glu
            355                 360                 365 gac cta aaa tct ctt att gat aaa gcg cat gag ctt ggc ttg cta gtg           1153
Asp Leu Lys Ser Leu Ile Asp Lys Ala His Glu Leu Gly Leu Leu Val
            370                 375                 380 ctt atg gat att gtt cat agt cat tca tca aat aat acc ttg gat ggt           1201
Leu Met Asp Ile Val His Ser His Ser Ser Asn Asn Thr Leu Asp Gly
385                 390                 395                 400 ttg aat ggt ttc gat ggc acc gat aca cat tac ttc cat ggt ggt cca           1249
Leu Asn Gly Phe Asp Gly Thr Asp Thr His Tyr Phe His Gly Gly Pro
            405                 410                 415 cga ggc cat cat tgg atg tgg gat tct cgc cta ttc aat tat ggg agt           1297
Arg Gly His His Trp Met Trp Asp Ser Arg Leu Phe Asn Tyr Gly Ser
            420                 425                 430 tgg gaa gtt ttg aga ttt cta ttg tca aat gcg aga tgg tgg ctt gaa           1345
Trp Glu Val Leu Arg Phe Leu Leu Ser Asn Ala Arg Trp Trp Leu Glu
            435                 440                 445 gaa tat aaa ttt gat ggg ttt cga ttt gat ggg gtg acc tcc atg atg           1393
Glu Tyr Lys Phe Asp Gly Phe Arg Phe Asp Gly Val Thr Ser Met Met
            450                 455                 460
```

```
tat act cac cat gga tta caa gtg aca ttc act ggg aac tat ggc gag      1441
Tyr Thr His His Gly Leu Gln Val Thr Phe Thr Gly Asn Tyr Gly Glu
465             470                 475                 480 tat ttt gga ttt gcc act gat gtt gat gca gta gtt tac cta atg ctg      1489
Tyr Phe Gly Phe Ala Thr Asp Val Asp Ala Val Val Tyr Leu Met Leu
                485                 490                 495 gta aac gat ctt att cgt ggg ctt tat cca gaa gct gta tcc att ggc      1537
Val Asn Asp Leu Ile Arg Gly Leu Tyr Pro Glu Ala Val Ser Ile Gly
500                 505                 510 gaa gat gtc agc gga atg cct aca ttt tgt atc cct gtc caa gat ggt      1585
Glu Asp Val Ser Gly Met Pro Thr Phe Cys Ile Pro Val Gln Asp Gly
            515                 520                 525 ggt gtt ggt ttt gat tat cgt ctt cat atg gct gtc cca gac aaa tgg      1633
Gly Val Gly Phe Asp Tyr Arg Leu His Met Ala Val Pro Asp Lys Trp
530                 535                 540 att gaa ctt ctg aag caa agt gac gaa tat tgg gaa atg ggt gac atc      1681
Ile Glu Leu Leu Lys Gln Ser Asp Glu Tyr Trp Glu Met Gly Asp Ile
545                 550                 555                 560 gtg cac acc tta aca aat aga agg tgg ctt gaa aag tgt gtc act tat      1729
Val His Thr Leu Thr Asn Arg Arg Trp Leu Glu Lys Cys Val Thr Tyr
                565                 570                 575 tgt gaa agt cat gat caa gct ctt gtt ggt gac aag aca att gca ttc      1777
Cys Glu Ser His Asp Gln Ala Leu Val Gly Asp Lys Thr Ile Ala Phe
                580                 585                 590 tgg ttg atg gat aag gat atg tat gat ttc atg gct ctg gac agg cct      1825
Trp Leu Met Asp Lys Asp Met Tyr Asp Phe Met Ala Leu Asp Arg Pro
            595                 600                 605 tca acg cct cgc atc gat cgt ggg ata gca tta cat aaa atg att agg      1873
Ser Thr Pro Arg Ile Asp Arg Gly Ile Ala Leu His Lys Met Ile Arg
610                 615                 620 ctt gtc aca atg ggt tta gga ggt gaa ggc tat cta aat ttc atg gga      1921
Leu Val Thr Met Gly Leu Gly Gly Glu Gly Tyr Leu Asn Phe Met Gly
625                 630                 635                 640 aat gag ttt ggg cat cct gaa tgg ata gat ttt cca aga ggt cct caa      1969
Asn Glu Phe Gly His Pro Glu Trp Ile Asp Phe Pro Arg Gly Pro Gln
                645                 650                 655 agt ctt cca aat ggc tcc gtc att cct ggg aat aac aat agc ttt gat      2017
Ser Leu Pro Asn Gly Ser Val Ile Pro Gly Asn Asn Asn Ser Phe Asp
            660                 665                 670 aaa tgc cgc cgt aga ttt gac ctt gga gat gca gat tat ctt aga tat      2065
Lys Cys Arg Arg Arg Phe Asp Leu Gly Asp Ala Asp Tyr Leu Arg Tyr
            675                 680                 685 cgt ggt atg caa gag ttt gac cag gca atg cag cac ctt gag gga aaa      2113
Arg Gly Met Gln Glu Phe Asp Gln Ala Met Gln His Leu Glu Gly Lys
690                 695                 700 tat gaa ttc atg aca tct gat cac tca tat gta tca cgg aag cat gag      2161
Tyr Glu Phe Met Thr Ser Asp His Ser Tyr Val Ser Arg Lys His Glu
705                 710                 715                 720 gag gat aag gtg atc atc ttt gag aga gga gat ttg gtc ttc gtg ttc      2209
Glu Asp Lys Val Ile Ile Phe Glu Arg Gly Asp Leu Val Phe Val Phe
                725                 730                 735 aac ttc cac tgg agc aat agc tat ttt gac tat cgc gtt ggt tgt ttc      2257
Asn Phe His Trp Ser Asn Ser Tyr Phe Asp Tyr Arg Val Gly Cys Phe
                740                 745                 750 aag cct ggg aag tac aag atc gtt tta gat tct gac gat ggc ctt ttc      2305
Lys Pro Gly Lys Tyr Lys Ile Val Leu Asp Ser Asp Asp Gly Leu Phe
            755                 760                 765 ggt gga ttt agt cgg ctt gat cat gat gcc gag tac ttc act gct gac      2353
Gly Gly Phe Ser Arg Leu Asp His Asp Ala Glu Tyr Phe Thr Ala Asp
770                 775                 780
```

```
tgg ccg cat gac aac agg ccg tgt tct ttc tcg gtc tat gca ccc agc     2401
Trp Pro His Asp Asn Arg Pro Cys Ser Phe Ser Val Tyr Ala Pro Ser
785             790                 795                 800 aga aca gcc gtc gta tat gca cct gca ggt gca gag gac gaa tag         2446
Arg Thr Ala Val Val Tyr Ala Pro Ala Gly Ala Glu Asp Glu *
                805                 810

<210> SEQ ID NO 10
<211> LENGTH: 814
<212> TYPE: PRT
<213> ORGANISM: Zea mays

<400> SEQUENCE: 10

Asp Leu Pro Ser Val Leu Phe Arg Arg Lys Asp Ala Phe Ser Arg Thr
1               5                   10                  15

Val Leu Ser Cys Ala Gly Ala Pro Gly Lys Val Leu Val Pro Gly Gly
            20                  25                  30

Gly Ser Asp Asp Leu Leu Ser Ser Ala Glu Pro Val Val Asp Thr Gln
        35                  40                  45

Pro Glu Glu Leu Gln Ile Pro Glu Ala Glu Leu Thr Val Glu Lys Thr
    50                  55                  60

Ser Ser Ser Pro Thr Gln Thr Thr Ser Ala Val Ala Glu Ala Ser Ser
65                  70                  75                  80

Gly Val Glu Ala Glu Glu Arg Pro Glu Leu Ser Glu Val Ile Gly Val
                85                  90                  95

Gly Gly Thr Gly Gly Thr Lys Ile Asp Gly Ala Gly Ile Lys Ala Lys
            100                 105                 110

Ala Pro Leu Val Glu Glu Lys Pro Arg Val Ile Pro Pro Gly Asp
        115                 120                 125

Gly Gln Arg Ile Tyr Glu Ile Asp Pro Met Leu Glu Gly Phe Arg Gly
    130                 135                 140

His Leu Asp Tyr Arg Tyr Ser Glu Tyr Lys Arg Leu Arg Ala Ala Ile
145                 150                 155                 160

Asp Gln His Glu Gly Gly Leu Asp Ala Phe Ser Arg Gly Tyr Glu Lys
                165                 170                 175

Leu Gly Phe Thr Arg Ser Ala Glu Gly Ile Thr Tyr Arg Glu Trp Ala
            180                 185                 190

Pro Gly Ala Tyr Ser Ala Ala Leu Val Gly Asp Phe Asn Asn Trp Asn
        195                 200                 205

Pro Asn Ala Asp Ala Met Ala Arg Asn Glu Tyr Gly Val Trp Glu Ile
    210                 215                 220

Phe Leu Pro Asn Asn Ala Asp Gly Ser Pro Ala Ile Pro His Gly Ser
225                 230                 235                 240

Arg Val Lys Ile Arg Met Asp Thr Pro Ser Gly Val Lys Asp Ser Ile
                245                 250                 255

Pro Ala Trp Ile Lys Phe Ser Val Gln Ala Pro Gly Glu Ile Pro Tyr
            260                 265                 270

Asn Gly Ile Tyr Tyr Asp Pro Pro Glu Glu Glu Lys Tyr Val Phe Lys
        275                 280                 285

His Pro Gln Pro Lys Arg Pro Lys Ser Leu Arg Ile Tyr Glu Ser His
    290                 295                 300

Val Gly Met Ser Ser Pro Glu Pro Lys Ile Asn Thr Tyr Ala Asn Phe
305                 310                 315                 320

Arg Asp Glu Val Leu Pro Arg Ile Lys Lys Leu Gly Tyr Asn Ala Val
                325                 330                 335
```

-continued

```
Gln Ile Met Ala Ile Gln Glu His Ser Tyr Tyr Ala Ser Phe Gly Tyr
                340                 345                 350
His Val Thr Asn Phe Phe Ala Pro Ser Ser Arg Phe Gly Thr Pro Glu
            355                 360                 365
Asp Leu Lys Ser Leu Ile Asp Lys Ala His Glu Leu Gly Leu Leu Val
        370                 375                 380
Leu Met Asp Ile Val His Ser His Ser Ser Asn Asn Thr Leu Asp Gly
385                 390                 395                 400
Leu Asn Gly Phe Asp Gly Thr Asp Thr His Tyr Phe His Gly Gly Pro
                405                 410                 415
Arg Gly His His Trp Met Trp Asp Ser Arg Leu Phe Asn Tyr Gly Ser
            420                 425                 430
Trp Glu Val Leu Arg Phe Leu Leu Ser Asn Ala Arg Trp Trp Leu Glu
        435                 440                 445
Glu Tyr Lys Phe Asp Gly Phe Arg Phe Asp Gly Val Thr Ser Met Met
            450                 455                 460
Tyr Thr His His Gly Leu Gln Val Thr Phe Thr Gly Asn Tyr Gly Glu
465                 470                 475                 480
Tyr Phe Gly Phe Ala Thr Asp Val Asp Ala Val Val Tyr Leu Met Leu
                485                 490                 495
Val Asn Asp Leu Ile Arg Gly Leu Tyr Pro Glu Ala Val Ser Ile Gly
            500                 505                 510
Glu Asp Val Ser Gly Met Pro Thr Phe Cys Ile Pro Val Gln Asp Gly
        515                 520                 525
Gly Val Gly Phe Asp Tyr Arg Leu His Met Ala Val Pro Asp Lys Trp
            530                 535                 540
Ile Glu Leu Leu Lys Gln Ser Asp Glu Tyr Trp Glu Met Gly Asp Ile
545                 550                 555                 560
Val His Thr Leu Thr Asn Arg Arg Trp Leu Glu Lys Cys Val Thr Tyr
                565                 570                 575
Cys Glu Ser His Asp Gln Ala Leu Val Gly Asp Lys Thr Ile Ala Phe
            580                 585                 590
Trp Leu Met Asp Lys Asp Met Tyr Asp Phe Met Ala Leu Asp Arg Pro
        595                 600                 605
Ser Thr Pro Arg Ile Asp Arg Gly Ile Ala Leu His Lys Met Ile Arg
            610                 615                 620
Leu Val Thr Met Gly Leu Gly Gly Glu Gly Tyr Leu Asn Phe Met Gly
625                 630                 635                 640
Asn Glu Phe Gly His Pro Glu Trp Ile Asp Phe Pro Arg Gly Pro Gln
                645                 650                 655
Ser Leu Pro Asn Gly Ser Val Ile Pro Gly Asn Asn Asn Ser Phe Asp
            660                 665                 670
Lys Cys Arg Arg Phe Asp Leu Gly Asp Ala Asp Tyr Leu Arg Tyr
        675                 680                 685
Arg Gly Met Gln Glu Phe Asp Gln Ala Met Gln His Leu Glu Gly Lys
            690                 695                 700
Tyr Glu Phe Met Thr Ser Asp His Ser Tyr Val Ser Arg Lys His Glu
705                 710                 715                 720
Glu Asp Lys Val Ile Ile Phe Glu Arg Gly Asp Leu Val Phe Val Phe
                725                 730                 735
Asn Phe His Trp Ser Asn Ser Tyr Phe Asp Tyr Arg Val Gly Cys Phe
            740                 745                 750
```

```
Lys Pro Gly Lys Tyr Lys Ile Val Leu Asp Ser Asp Gly Leu Phe
            755                 760                 765

Gly Gly Phe Ser Arg Leu Asp His Asp Ala Glu Tyr Phe Thr Ala Asp
        770                 775                 780

Trp Pro His Asp Asn Arg Pro Cys Ser Phe Ser Val Tyr Ala Pro Ser
785                 790                 795                 800

Arg Thr Ala Val Val Tyr Ala Pro Ala Gly Ala Glu Asp Glu
                805                 810

<210> SEQ ID NO 11
<211> LENGTH: 2720
<212> TYPE: DNA
<213> ORGANISM: Zea mays
<220> FEATURE:
<221> NAME/KEY: misc_feature
<222> LOCATION: (0)...(0)
<223> OTHER INFORMATION: SBEIIb
      Genbank Accession No. AF072725
<221> NAME/KEY: CDS
<222> LOCATION: (101)...(2500)

<400> SEQUENCE: 11
gccctgcagt cacccagagc agacccggat ttcgctcttg cggtcgctgg ggttttagca      60
ttggctgatc agttcgatcc gatccggctg cgaaggcgag atg gcg ttc cgg gtt     115
                                             Met Ala Phe Arg Val
                                               1               5 tct ggg gcg gtg ctc ggt ggg gcc gta agg gct ccc cga ctc acc ggc     163
Ser Gly Ala Val Leu Gly Gly Ala Val Arg Ala Pro Arg Leu Thr Gly
             10                  15                  20 ggc ggg gag ggt agt cta gtc ttc cgg cac acc ggc ctc ttc tta act     211
Gly Gly Glu Gly Ser Leu Val Phe Arg His Thr Gly Leu Phe Leu Thr
         25                  30                  35 cgg ggt gct cga gtt gga tgt tcg ggg acg cac ggg gcc atg cgc gcg     259
Arg Gly Ala Arg Val Gly Cys Ser Gly Thr His Gly Ala Met Arg Ala
     40                  45                  50 gcg gcc gcg gcc agg aaa gcg gtc atg gtt cct gag ggc gag aat gat     307
Ala Ala Ala Ala Arg Lys Ala Val Met Val Pro Glu Gly Glu Asn Asp
 55                  60                  65 ggc ctc gca tca agg gct gac tcg gct caa ttc cag tcg gat gaa ctg     355
Gly Leu Ala Ser Arg Ala Asp Ser Ala Gln Phe Gln Ser Asp Glu Leu
 70                  75                  80                  85 gag gta cca gac att tct gaa gag aca acg tgc ggt gct ggt gtg gct     403
Glu Val Pro Asp Ile Ser Glu Glu Thr Thr Cys Gly Ala Gly Val Ala
                 90                  95                 100 gat gct caa gcc ttg aac aga gtt cga gtg gtc ccc cca cca agc gat     451
Asp Ala Gln Ala Leu Asn Arg Val Arg Val Val Pro Pro Pro Ser Asp
            105                 110                 115 gga caa aaa ata ttc cag att gac ccc atg ttg caa ggc tat aag tac     499
Gly Gln Lys Ile Phe Gln Ile Asp Pro Met Leu Gln Gly Tyr Lys Tyr
        120                 125                 130 cat ctt gag tat cgg tac agc ctc tat aga aga atc cgt tca gac att     547
His Leu Glu Tyr Arg Tyr Ser Leu Tyr Arg Arg Ile Arg Ser Asp Ile
    135                 140                 145 gat gaa cat gaa gga ggc ttg gaa gcc ttc tcc cgt agt tat gag aag     595
Asp Glu His Glu Gly Gly Leu Glu Ala Phe Ser Arg Ser Tyr Glu Lys
150                 155                 160                 165 ttt gga ttt aat cgc agc gcg gaa ggt atc aca tat cga gaa tgg gct     643
Phe Gly Phe Asn Arg Ser Ala Glu Gly Ile Thr Tyr Arg Glu Trp Ala
                170                 175                 180 cct gga gca ttt tct gca gca ttg gtg ggt gac ttc aac aac tgg gat     691
Pro Gly Ala Phe Ser Ala Ala Leu Val Gly Asp Phe Asn Asn Trp Asp
```

|  |  |  |  |  |  |  |  |  |  |  |  |  |  |  |  |
|---|---|---|---|---|---|---|---|---|---|---|---|---|---|---|---|
|  |  | 185 |  |  |  | 190 |  |  |  | 195 |  |  |  |  |  |
| cca | aat | gca | gat | cgt | atg | agc | aaa | aat | gag | ttt | ggt | gtt | tgg | gaa | att | 739 |
| Pro | Asn | Ala | Asp | Arg | Met | Ser | Lys | Asn | Glu | Phe | Gly | Val | Trp | Glu | Ile |  |
|  |  | 200 |  |  |  | 205 |  |  |  | 210 |  |  |  |  |  |
| ttt | ctg | cct | aac | aat | gca | gat | ggt | aca | tca | cct | att | cct | cat | gga | tct | 787 |
| Phe | Leu | Pro | Asn | Asn | Ala | Asp | Gly | Thr | Ser | Pro | Ile | Pro | His | Gly | Ser |  |
|  | 215 |  |  |  |  | 220 |  |  |  |  | 225 |  |  |  |  |  |
| cgt | gta | aag | gtg | aga | atg | gat | act | cca | tca | ggg | ata | aag | gat | tca | att | 835 |
| Arg | Val | Lys | Val | Arg | Met | Asp | Thr | Pro | Ser | Gly | Ile | Lys | Asp | Ser | Ile |  |
| 230 |  |  |  |  | 235 |  |  |  |  | 240 |  |  |  |  | 245 |  |
| cca | gcc | tgg | atc | aag | tac | tca | gtg | cag | gcc | cca | gga | gaa | ata | cca | tat | 883 |
| Pro | Ala | Trp | Ile | Lys | Tyr | Ser | Val | Gln | Ala | Pro | Gly | Glu | Ile | Pro | Tyr |  |
|  |  |  |  | 250 |  |  |  |  | 255 |  |  |  |  | 260 |  |  |
| gat | ggg | att | tat | tat | gat | cct | cct | gaa | gag | gta | aag | tat | gtg | ttc | agg | 931 |
| Asp | Gly | Ile | Tyr | Tyr | Asp | Pro | Pro | Glu | Glu | Val | Lys | Tyr | Val | Phe | Arg |  |
|  |  |  |  | 265 |  |  |  |  | 270 |  |  |  |  | 275 |  |  |
| cat | gcg | caa | cct | aaa | cga | cca | aaa | tca | ttg | cgg | ata | tat | gaa | aca | cat | 979 |
| His | Ala | Gln | Pro | Lys | Arg | Pro | Lys | Ser | Leu | Arg | Ile | Tyr | Glu | Thr | His |  |
|  |  |  | 280 |  |  |  |  | 285 |  |  |  |  | 290 |  |  |  |
| gtc | gga | atg | agt | agc | ccg | gaa | ccg | aag | ata | aac | aca | tat | gta | aac | ttt | 1027 |
| Val | Gly | Met | Ser | Ser | Pro | Glu | Pro | Lys | Ile | Asn | Thr | Tyr | Val | Asn | Phe |  |
| 295 |  |  |  |  | 300 |  |  |  |  | 305 |  |  |  |  |  |  |
| agg | gat | gaa | gtc | ctc | cca | aga | ata | aaa | aaa | ctt | gga | tac | aat | gca | gtg | 1075 |
| Arg | Asp | Glu | Val | Leu | Pro | Arg | Ile | Lys | Lys | Leu | Gly | Tyr | Asn | Ala | Val |  |
| 310 |  |  |  |  | 315 |  |  |  |  | 320 |  |  |  |  | 325 |  |
| caa | ata | atg | gca | atc | caa | gag | cac | tca | tat | tat | gga | agc | ttt | gga | tac | 1123 |
| Gln | Ile | Met | Ala | Ile | Gln | Glu | His | Ser | Tyr | Tyr | Gly | Ser | Phe | Gly | Tyr |  |
|  |  |  |  | 330 |  |  |  |  | 335 |  |  |  |  | 340 |  |  |
| cat | gta | act | aat | ttt | ttt | gcg | cca | agt | agt | cgt | ttt | ggt | acc | cca | gaa | 1171 |
| His | Val | Thr | Asn | Phe | Phe | Ala | Pro | Ser | Ser | Arg | Phe | Gly | Thr | Pro | Glu |  |
|  |  |  | 345 |  |  |  |  | 350 |  |  |  |  | 355 |  |  |  |
| gaa | ttg | aag | tct | ttg | att | gat | aga | gca | cat | gag | ctt | ggt | ttg | cta | gtt | 1219 |
| Glu | Leu | Lys | Ser | Leu | Ile | Asp | Arg | Ala | His | Glu | Leu | Gly | Leu | Leu | Val |  |
|  |  | 360 |  |  |  |  | 365 |  |  |  |  | 370 |  |  |  |  |
| ctc | atg | gat | gtg | gtt | cat | agt | cat | gcg | tca | agt | aat | act | ctg | gat | ggg | 1267 |
| Leu | Met | Asp | Val | Val | His | Ser | His | Ala | Ser | Ser | Asn | Thr | Leu | Asp | Gly |  |
|  | 375 |  |  |  |  | 380 |  |  |  |  | 385 |  |  |  |  |  |
| ttg | aat | ggt | ttt | gat | ggt | aca | gat | aca | cat | tac | ttt | cac | agt | ggt | cca | 1315 |
| Leu | Asn | Gly | Phe | Asp | Gly | Thr | Asp | Thr | His | Tyr | Phe | His | Ser | Gly | Pro |  |
| 390 |  |  |  |  | 395 |  |  |  |  | 400 |  |  |  |  | 405 |  |
| cgt | ggc | cat | cac | tgg | atg | tgg | gat | tct | cgc | cta | ttt | aac | tat | ggg | aac | 1363 |
| Arg | Gly | His | His | Trp | Met | Trp | Asp | Ser | Arg | Leu | Phe | Asn | Tyr | Gly | Asn |  |
|  |  |  |  | 410 |  |  |  |  | 415 |  |  |  |  | 420 |  |  |
| tgg | gaa | gtt | tta | aga | ttt | ctt | ctc | tcc | aat | gct | aga | tgg | tgg | ctc | gag | 1411 |
| Trp | Glu | Val | Leu | Arg | Phe | Leu | Leu | Ser | Asn | Ala | Arg | Trp | Trp | Leu | Glu |  |
|  |  |  | 425 |  |  |  |  | 430 |  |  |  |  | 435 |  |  |  |
| gaa | tat | aag | ttt | gat | ggt | ttc | cgt | ttt | gat | ggt | gtg | acc | tcc | atg | atg | 1459 |
| Glu | Tyr | Lys | Phe | Asp | Gly | Phe | Arg | Phe | Asp | Gly | Val | Thr | Ser | Met | Met |  |
|  |  | 440 |  |  |  |  | 445 |  |  |  |  | 450 |  |  |  |  |
| tac | act | cat | cac | gga | tta | caa | gta | aca | ttt | acg | ggg | aac | ttc | aat | gag | 1507 |
| Tyr | Thr | His | His | Gly | Leu | Gln | Val | Thr | Phe | Thr | Gly | Asn | Phe | Asn | Glu |  |
|  | 455 |  |  |  |  | 460 |  |  |  |  | 465 |  |  |  |  |  |
| tat | ttt | ggc | ttt | gcc | acc | gat | gta | gat | gca | gtg | gtt | tac | ttg | atg | ctg | 1555 |
| Tyr | Phe | Gly | Phe | Ala | Thr | Asp | Val | Asp | Ala | Val | Val | Tyr | Leu | Met | Leu |  |
| 470 |  |  |  |  | 475 |  |  |  |  | 480 |  |  |  |  | 485 |  |
| gta | aat | gat | cta | att | cat | gga | ctt | tat | cct | gag | gct | gta | acc | att | ggt | 1603 |
| Val | Asn | Asp | Leu | Ile | His | Gly | Leu | Tyr | Pro | Glu | Ala | Val | Thr | Ile | Gly |  |
|  |  |  |  | 490 |  |  |  |  | 495 |  |  |  |  | 500 |  |  |
| gaa | gat | gtt | agt | gga | atg | cct | aca | ttt | gcc | ctt | cct | gtt | cac | gat | ggt | 1651 |

-continued

```
Glu Asp Val Ser Gly Met Pro Thr Phe Ala Leu Pro Val His Asp Gly
    505                 510                 515 ggg gta ggt ttt gac tat cgg atg cat atg gct gtg gct gac aaa tgg      1699
Gly Val Gly Phe Asp Tyr Arg Met His Met Ala Val Ala Asp Lys Trp
520                 525                 530 att gac ctt ctc aag caa agt gat gaa act tgg aag atg ggt gat att      1747
Ile Asp Leu Leu Lys Gln Ser Asp Glu Thr Trp Lys Met Gly Asp Ile
535                 540                 545 gtg cac aca ctg aca aat agg agg tgg tta gag aag tgt gta act tat      1795
Val His Thr Leu Thr Asn Arg Arg Trp Leu Glu Lys Cys Val Thr Tyr
550                 555                 560                 565 gct gaa agt cat gat caa gca tta gtc ggc gac aag act att gcg ttt      1843
Ala Glu Ser His Asp Gln Ala Leu Val Gly Asp Lys Thr Ile Ala Phe
                570                 575                 580 tgg ttg atg gac aag gat atg tat gat ttc atg gcc ctc gat aga cct      1891
Trp Leu Met Asp Lys Asp Met Tyr Asp Phe Met Ala Leu Asp Arg Pro
            585                 590                 595 tca act cct acc att gat cgt ggg ata gca tta cat aag atg att aga      1939
Ser Thr Pro Thr Ile Asp Arg Gly Ile Ala Leu His Lys Met Ile Arg
        600                 605                 610 ctt atc aca atg ggt tta gga gga gag ggc tat ctt aat ttc atg gga      1987
Leu Ile Thr Met Gly Leu Gly Gly Glu Gly Tyr Leu Asn Phe Met Gly
615                 620                 625 aat gag ttt gga cat cct gaa tgg ata gat ttt cca aga ggt ccg caa      2035
Asn Glu Phe Gly His Pro Glu Trp Ile Asp Phe Pro Arg Gly Pro Gln
630                 635                 640                 645 aga ctt cca agt ggt aag ttt att cca ggg aat aac aac agt tat gac      2083
Arg Leu Pro Ser Gly Lys Phe Ile Pro Gly Asn Asn Asn Ser Tyr Asp
                650                 655                 660 aaa tgt cgt cga aga ttt gac ctg ggt gat gca gac tat ctt agg tat      2131
Lys Cys Arg Arg Arg Phe Asp Leu Gly Asp Ala Asp Tyr Leu Arg Tyr
            665                 670                 675 cat ggt atg caa gag ttt gat cag gca atg caa cat ctt gag caa aaa      2179
His Gly Met Gln Glu Phe Asp Gln Ala Met Gln His Leu Glu Gln Lys
        680                 685                 690 tat gaa ttc atg aca tct gat cac cag tat att tcc cgg aaa cat gag      2227
Tyr Glu Phe Met Thr Ser Asp His Gln Tyr Ile Ser Arg Lys His Glu
695                 700                 705 gag gat aag gtg att gtg ttc gaa aag gga gat ttg gta ttt gtg ttc      2275
Glu Asp Lys Val Ile Val Phe Glu Lys Gly Asp Leu Val Phe Val Phe
710                 715                 720                 725 aac ttc cac tgc aac aac agc tat ttt gac tac cgt att ggt tgt cga      2323
Asn Phe His Cys Asn Asn Ser Tyr Phe Asp Tyr Arg Ile Gly Cys Arg
                730                 735                 740 aag cct ggg gtg tat aag gtg gtc ttg gac tcc gac gct gga cta ttt      2371
Lys Pro Gly Val Tyr Lys Val Val Leu Asp Ser Asp Ala Gly Leu Phe
            745                 750                 755 ggt gga ttt agc agg atc cat cac gca gcc gag cac ttc acc gcc gac      2419
Gly Gly Phe Ser Arg Ile His His Ala Ala Glu His Phe Thr Ala Asp
        760                 765                 770 tgt tcg cat gat aat agg cca tat tca ttc tcg gtt tat aca cca agc      2467
Cys Ser His Asp Asn Arg Pro Tyr Ser Phe Ser Val Tyr Thr Pro Ser
775                 780                 785 aga aca tgt gtc gtc tat gct cca gtg gag tga tagcggggta ctcgttgctg   2520
Arg Thr Cys Val Val Tyr Ala Pro Val Glu *
790                 795 cgcggcatgt gtggggctgt cgatgtgagg aaaaaccttc ttccaaaacc ggcagatgca   2580
tgcatgcatg ctacaataag gttctgatac tttaatcgat gctggaaagc ccatgcatct   2640
```

```
cgctgcgttg tcctctctat atatttaaga ccttcaaggt gtcaattaaa catagagttt    2700
tcgtttttcg ctttcctaat                                                2720
```

<210> SEQ ID NO 12
<211> LENGTH: 799
<212> TYPE: PRT
<213> ORGANISM: Zea mays

<400> SEQUENCE: 12

| | | | | | | | | | | | | | | |
|---|---|---|---|---|---|---|---|---|---|---|---|---|---|---|
| Met | Ala | Phe | Arg | Val | Ser | Gly | Ala | Val | Leu | Gly | Gly | Ala | Val | Arg | Ala |
| 1 | | | | 5 | | | | | 10 | | | | | 15 | |
| Pro | Arg | Leu | Thr | Gly | Gly | Glu | Gly | Ser | Leu | Val | Phe | Arg | His | Thr | |
| | | | 20 | | | | 25 | | | | | 30 | | | |
| Gly | Leu | Phe | Leu | Thr | Arg | Gly | Ala | Arg | Val | Gly | Cys | Ser | Gly | Thr | His |
| | | 35 | | | | | 40 | | | | | 45 | | | |
| Gly | Ala | Met | Arg | Ala | Ala | Ala | Ala | Arg | Lys | Ala | Val | Met | Val | Pro | |
| | 50 | | | | | 55 | | | | | 60 | | | | |
| Glu | Gly | Glu | Asn | Asp | Gly | Leu | Ala | Ser | Arg | Ala | Asp | Ser | Ala | Gln | Phe |
| 65 | | | | | 70 | | | | | 75 | | | | | 80 |
| Gln | Ser | Asp | Glu | Leu | Glu | Val | Pro | Asp | Ile | Ser | Glu | Thr | Thr | Cys | |
| | | | | 85 | | | | | 90 | | | | | 95 | |
| Gly | Ala | Gly | Val | Ala | Asp | Ala | Gln | Ala | Leu | Asn | Arg | Val | Arg | Val | Val |
| | | | 100 | | | | | 105 | | | | | 110 | | |
| Pro | Pro | Pro | Ser | Asp | Gly | Gln | Lys | Ile | Phe | Gln | Ile | Asp | Pro | Met | Leu |
| | | | 115 | | | | 120 | | | | | 125 | | | |
| Gln | Gly | Tyr | Lys | Tyr | His | Leu | Glu | Tyr | Arg | Tyr | Ser | Leu | Tyr | Arg | Arg |
| | 130 | | | | | 135 | | | | | 140 | | | | |
| Ile | Arg | Ser | Asp | Ile | Asp | Glu | His | Glu | Gly | Gly | Leu | Glu | Ala | Phe | Ser |
| 145 | | | | | 150 | | | | | 155 | | | | | 160 |
| Arg | Ser | Tyr | Glu | Lys | Phe | Gly | Phe | Asn | Arg | Ser | Ala | Glu | Gly | Ile | Thr |
| | | | | 165 | | | | | 170 | | | | | 175 | |
| Tyr | Arg | Glu | Trp | Ala | Pro | Gly | Ala | Phe | Ser | Ala | Ala | Leu | Val | Gly | Asp |
| | | | 180 | | | | | 185 | | | | | 190 | | |
| Phe | Asn | Asn | Trp | Asp | Pro | Asn | Ala | Asp | Arg | Met | Ser | Lys | Asn | Glu | Phe |
| | | 195 | | | | | 200 | | | | | 205 | | | |
| Gly | Val | Trp | Glu | Ile | Phe | Leu | Pro | Asn | Asn | Ala | Asp | Gly | Thr | Ser | Pro |
| | 210 | | | | | 215 | | | | | 220 | | | | |
| Ile | Pro | His | Gly | Ser | Arg | Val | Lys | Val | Arg | Met | Asp | Thr | Pro | Ser | Gly |
| 225 | | | | | 230 | | | | | 235 | | | | | 240 |
| Ile | Lys | Asp | Ser | Ile | Pro | Ala | Trp | Ile | Lys | Tyr | Ser | Val | Gln | Ala | Pro |
| | | | | 245 | | | | | 250 | | | | | 255 | |
| Gly | Glu | Ile | Pro | Tyr | Asp | Gly | Ile | Tyr | Tyr | Asp | Pro | Pro | Glu | Glu | Val |
| | | | 260 | | | | | 265 | | | | | 270 | | |
| Lys | Tyr | Val | Phe | Arg | His | Ala | Gln | Pro | Lys | Arg | Pro | Lys | Ser | Leu | Arg |
| | | 275 | | | | | 280 | | | | | 285 | | | |
| Ile | Tyr | Glu | Thr | His | Val | Gly | Met | Ser | Ser | Pro | Glu | Pro | Lys | Ile | Asn |
| | 290 | | | | | 295 | | | | | 300 | | | | |
| Thr | Tyr | Val | Asn | Phe | Arg | Asp | Glu | Val | Leu | Pro | Arg | Ile | Lys | Lys | Leu |
| 305 | | | | | 310 | | | | | 315 | | | | | 320 |
| Gly | Tyr | Asn | Ala | Val | Gln | Ile | Met | Ala | Ile | Gln | Glu | His | Ser | Tyr | Tyr |
| | | | | 325 | | | | | 330 | | | | | 335 | |
| Gly | Ser | Phe | Gly | Tyr | His | Val | Thr | Asn | Phe | Phe | Ala | Pro | Ser | Ser | Arg |
| | | | 340 | | | | | 345 | | | | | 350 | | |
| Phe | Gly | Thr | Pro | Glu | Glu | Leu | Lys | Ser | Leu | Ile | Asp | Arg | Ala | His | Glu |

-continued

```
            355                 360                 365
Leu Gly Leu Leu Val Leu Met Asp Val Val His Ser His Ala Ser Ser
    370                 375                 380
Asn Thr Leu Asp Gly Leu Asn Gly Phe Asp Thr Asp Thr His Tyr
385                 390                 395                 400
Phe His Ser Gly Pro Arg Gly His His Trp Met Trp Asp Ser Arg Leu
                405                 410                 415
Phe Asn Tyr Gly Asn Trp Glu Val Leu Arg Phe Leu Leu Ser Asn Ala
            420                 425                 430
Arg Trp Trp Leu Glu Glu Tyr Lys Phe Asp Gly Phe Arg Phe Asp Gly
                435                 440                 445
Val Thr Ser Met Met Tyr Thr His His Gly Leu Gln Val Thr Phe Thr
    450                 455                 460
Gly Asn Phe Asn Glu Tyr Phe Gly Phe Ala Thr Asp Val Asp Ala Val
465                 470                 475                 480
Val Tyr Leu Met Leu Val Asn Asp Leu Ile His Gly Leu Tyr Pro Glu
                485                 490                 495
Ala Val Thr Ile Gly Glu Asp Val Ser Gly Met Pro Thr Phe Ala Leu
            500                 505                 510
Pro Val His Asp Gly Gly Val Gly Phe Asp Tyr Arg Met His Met Ala
                515                 520                 525
Val Ala Asp Lys Trp Ile Asp Leu Leu Lys Gln Ser Asp Glu Thr Trp
    530                 535                 540
Lys Met Gly Asp Ile Val His Thr Leu Thr Asn Arg Arg Trp Leu Glu
545                 550                 555                 560
Lys Cys Val Thr Tyr Ala Glu Ser His Asp Gln Ala Leu Val Gly Asp
                565                 570                 575
Lys Thr Ile Ala Phe Trp Leu Met Asp Lys Asp Met Tyr Asp Phe Met
            580                 585                 590
Ala Leu Asp Arg Pro Ser Thr Pro Thr Ile Asp Arg Gly Ile Ala Leu
                595                 600                 605
His Lys Met Ile Arg Leu Ile Thr Met Gly Leu Gly Gly Glu Gly Tyr
    610                 615                 620
Leu Asn Phe Met Gly Asn Glu Phe Gly His Pro Glu Trp Ile Asp Phe
625                 630                 635                 640
Pro Arg Gly Pro Gln Arg Leu Pro Ser Gly Lys Phe Ile Pro Gly Asn
                645                 650                 655
Asn Asn Ser Tyr Asp Lys Cys Arg Arg Phe Asp Leu Gly Asp Ala
            660                 665                 670
Asp Tyr Leu Arg Tyr His Gly Met Gln Glu Phe Asp Gln Ala Met Gln
                675                 680                 685
His Leu Glu Gln Lys Tyr Glu Phe Met Thr Ser Asp His Gln Tyr Ile
    690                 695                 700
Ser Arg Lys His Glu Glu Asp Lys Val Ile Val Phe Glu Lys Gly Asp
705                 710                 715                 720
Leu Val Phe Val Phe Asn Phe His Cys Asn Asn Ser Tyr Phe Asp Tyr
                725                 730                 735
Arg Ile Gly Cys Arg Lys Pro Gly Val Tyr Lys Val Val Leu Asp Ser
            740                 745                 750
Asp Ala Gly Leu Phe Gly Gly Phe Ser Arg Ile His His Ala Ala Glu
                755                 760                 765
His Phe Thr Ala Asp Cys Ser His Asp Asn Arg Pro Tyr Ser Phe Ser
    770                 775                 780
```

```
Val Tyr Thr Pro Ser Arg Thr Cys Val Val Tyr Ala Pro Val Glu
785                 790                 795

<210> SEQ ID NO 13
<211> LENGTH: 2470
<212> TYPE: DNA
<213> ORGANISM: Zea mays
<220> FEATURE:
<221> NAME/KEY: misc_feature
<222> LOCATION: (0)...(0)
<223> OTHER INFORMATION: SBEI -- Genbank Accession No. 217959
<221> NAME/KEY: CDS
<222> LOCATION: (2)...(2470)

<400> SEQUENCE: 13 g ctg tgc ctc gtg tcg ccc tct tcc tcg ccg act ccg ctt ccg ccg ccg         49
  Leu Cys Leu Val Ser Pro Ser Ser Ser Pro Thr Pro Leu Pro Pro Pro
  1               5                   10                  15 cgg cgc tct cgc tcg cat gct gat cgg gcg gca ccg ccg ggg atc gcg          97
Arg Arg Ser Arg Ser His Ala Asp Arg Ala Ala Pro Pro Gly Ile Ala
                20                  25                  30 ggt ggc ggc aat gtg cgc ctg agt gtg ttg tct gtc cag tgc aag gct         145
Gly Gly Gly Asn Val Arg Leu Ser Val Leu Ser Val Gln Cys Lys Ala
            35                  40                  45 cgc cgg tca ggg gtg cgg aag gtc aag agc aaa ttc gcc act gca gct         193
Arg Arg Ser Gly Val Arg Lys Val Lys Ser Lys Phe Ala Thr Ala Ala
        50                  55                  60 act gtg caa gaa gat aaa act atg gca act gcc aaa ggc gat gtc gac         241
Thr Val Gln Glu Asp Lys Thr Met Ala Thr Ala Lys Gly Asp Val Asp
65                  70                  75                  80 cat ctc ccc ata tac gac ctg gac ccc aag ctg gag ata ttc aag gac         289
His Leu Pro Ile Tyr Asp Leu Asp Pro Lys Leu Glu Ile Phe Lys Asp
                85                  90                  95 cat ttc agg tac cgg atg aaa aga ttc cta gag cag aaa gga tca att         337
His Phe Arg Tyr Arg Met Lys Arg Phe Leu Glu Gln Lys Gly Ser Ile
            100                 105                 110 gaa gaa aat gag gga agt ctt gaa tct ttt tct aaa ggc tat ttg aaa         385
Glu Glu Asn Glu Gly Ser Leu Glu Ser Phe Ser Lys Gly Tyr Leu Lys
        115                 120                 125 ttt ggg att aat aca aat gag gat gga act gta tat cgt gaa tgg gca         433
Phe Gly Ile Asn Thr Asn Glu Asp Gly Thr Val Tyr Arg Glu Trp Ala
    130                 135                 140 cct gct gcg cag gag gca gag ctt att ggt gac ttc aat gac tgg aat         481
Pro Ala Ala Gln Glu Ala Glu Leu Ile Gly Asp Phe Asn Asp Trp Asn
145                 150                 155                 160 ggt gca aac cat aag atg gag aag gat aaa ttt ggt gtt tgg tcg atc         529
Gly Ala Asn His Lys Met Glu Lys Asp Lys Phe Gly Val Trp Ser Ile
                165                 170                 175 aaa att gac cat gtc aaa ggg aaa cct gcc atc cct cac aat tcc aag         577
Lys Ile Asp His Val Lys Gly Lys Pro Ala Ile Pro His Asn Ser Lys
            180                 185                 190 gtt aaa ttt cgc ttt cta cat ggt gga gta tgg gtt gat cgt att cca         625
Val Lys Phe Arg Phe Leu His Gly Gly Val Trp Val Asp Arg Ile Pro
        195                 200                 205 gca ttg att cgt tat gcg act gtt gat gcc tct aaa ttt gga gct ccc         673
Ala Leu Ile Arg Tyr Ala Thr Val Asp Ala Ser Lys Phe Gly Ala Pro
    210                 215                 220 tat gat ggt gtt cat tgg gat cct cct gct tct gaa agg tac aca ttt         721
Tyr Asp Gly Val His Trp Asp Pro Pro Ala Ser Glu Arg Tyr Thr Phe
225                 230                 235                 240 aag cat cct cgg cct tca aag cct gct gct cca cgt atc tat gaa gcc         769
```

-continued

| | | | | | | | | | | | | |
|---|---|---|---|---|---|---|---|---|---|---|---|---|
| Lys | His | Pro | Arg | Pro | Ser | Lys | Pro | Ala | Ala | Pro | Arg | Ile | Tyr | Glu | Ala |
| | | | 245 | | | | 250 | | | | 255 | |

```
cat gta ggt atg agt ggt gaa aag cca gca gta agc aca tat agg gaa      817
His Val Gly Met Ser Gly Glu Lys Pro Ala Val Ser Thr Tyr Arg Glu
            260                 265                 270 ttt gca gac aat gtg ttg cca cgc ata cga gca aat aac tac aac aca      865
Phe Ala Asp Asn Val Leu Pro Arg Ile Arg Ala Asn Asn Tyr Asn Thr
            275                 280                 285 gtt cag ttg atg gca gtt atg gag cat tcg tac tat gct tct ttc ggg      913
Val Gln Leu Met Ala Val Met Glu His Ser Tyr Tyr Ala Ser Phe Gly
        290                 295                 300 tac cat gtg aca aat ttc ttt gcg gtt agc agc aga tca ggc aca cca      961
Tyr His Val Thr Asn Phe Phe Ala Val Ser Ser Arg Ser Gly Thr Pro
305                 310                 315                 320 gag gac ctc aaa tat ctt gtt gat aag gca cac agt ttg ggt ttg cga     1009
Glu Asp Leu Lys Tyr Leu Val Asp Lys Ala His Ser Leu Gly Leu Arg
                325                 330                 335 gtt ctg atg gat gtt gtc cat agc cat gca agt aat aat gtc aca gat     1057
Val Leu Met Asp Val Val His Ser His Ala Ser Asn Asn Val Thr Asp
            340                 345                 350 ggt tta aat ggc tat gat gtt gga caa agc acc caa gag tcc tat ttt     1105
Gly Leu Asn Gly Tyr Asp Val Gly Gln Ser Thr Gln Glu Ser Tyr Phe
        355                 360                 365 cat gcg gga gat aga ggt tat cat aaa ctt tgg gat agt cgg ctg ttc     1153
His Ala Gly Asp Arg Gly Tyr His Lys Leu Trp Asp Ser Arg Leu Phe
370                 375                 380 aac tat gct aac tgg gag gta tta agg ttt ctt ctt tct aac ctg aga     1201
Asn Tyr Ala Asn Trp Glu Val Leu Arg Phe Leu Leu Ser Asn Leu Arg
385                 390                 395                 400 tat tgg ttg gat gaa ttc atg ttt gat ggc ttc cga ttt gat gga gtt     1249
Tyr Trp Leu Asp Glu Phe Met Phe Asp Gly Phe Arg Phe Asp Gly Val
                405                 410                 415 aca tca atg ctg tat cat cac cat ggt atc aat gtg ggg ttt act gga     1297
Thr Ser Met Leu Tyr His His His Gly Ile Asn Val Gly Phe Thr Gly
            420                 425                 430 aac tac cag gaa tat ttc agt ttg gac aca gct gtg gat gca gtt gtt     1345
Asn Tyr Gln Glu Tyr Phe Ser Leu Asp Thr Ala Val Asp Ala Val Val
        435                 440                 445 tac atg atg ctt gca aac cat tta atg cac aaa ctc ttg cca gaa gca     1393
Tyr Met Met Leu Ala Asn His Leu Met His Lys Leu Leu Pro Glu Ala
450                 455                 460 act gtt gtt gct gaa gat gtt tca ggc atg ccg gtc ctt tgc cgg cca     1441
Thr Val Val Ala Glu Asp Val Ser Gly Met Pro Val Leu Cys Arg Pro
465                 470                 475                 480 gtt gat gaa ggt ggg gtt ggg ttt gac tat cgc ctg gca atg gct atc     1489
Val Asp Glu Gly Gly Val Gly Phe Asp Tyr Arg Leu Ala Met Ala Ile
                485                 490                 495 cct gat aga tgg att gac tac ctg aag aat aaa gat gac tct gag tgg     1537
Pro Asp Arg Trp Ile Asp Tyr Leu Lys Asn Lys Asp Asp Ser Glu Trp
            500                 505                 510 tcg atg ggt gaa ata gcg cat act ttg act aac agg aga tat act gaa     1585
Ser Met Gly Glu Ile Ala His Thr Leu Thr Asn Arg Arg Tyr Thr Glu
        515                 520                 525 aaa tgc atc gca tat gct gag agc cat gat cag tct att gtt ggc gac     1633
Lys Cys Ile Ala Tyr Ala Glu Ser His Asp Gln Ser Ile Val Gly Asp
530                 535                 540 aaa act att gca ttt ctc ctg atg gac aag gaa atg tac act ggc atg     1681
Lys Thr Ile Ala Phe Leu Leu Met Asp Lys Glu Met Tyr Thr Gly Met
545                 550                 555                 560
```

-continued

| | |
|---|---|
| tca gac ttg cag cct gct tca cct aca att gat cga ggg att gca ctc<br>Ser Asp Leu Gln Pro Ala Ser Pro Thr Ile Asp Arg Gly Ile Ala Leu<br>                565                    570                 575 | 1729 |
| caa aag atg att cac ttc atc aca atg gcc ctt gga ggt gat ggc tac<br>Gln Lys Met Ile His Phe Ile Thr Met Ala Leu Gly Gly Asp Gly Tyr<br>580                   585                    590 | 1777 |
| ttg aat ttt atg gga aat gag ttt ggt cac cca gaa tgg att gac ttt<br>Leu Asn Phe Met Gly Asn Glu Phe Gly His Pro Glu Trp Ile Asp Phe<br>     595                    600                   605 | 1825 |
| cca aga gaa ggg aac aac tgg agc tat gat aaa tgc aga cga cag tgg<br>Pro Arg Glu Gly Asn Asn Trp Ser Tyr Asp Lys Cys Arg Arg Gln Trp<br>610                 615                  620 | 1873 |
| agc ctt gtg gac act gat cac ttg cgg tac aag tac atg aat gcg ttt<br>Ser Leu Val Asp Thr Asp His Leu Arg Tyr Lys Tyr Met Asn Ala Phe<br>625                 630                 635                640 | 1921 |
| gac caa gcg atg aat gcg ctc gat gag aga ttt tcc ttc ctt tcg tcg<br>Asp Gln Ala Met Asn Ala Leu Asp Glu Arg Phe Ser Phe Leu Ser Ser<br>                645                  650                  655 | 1969 |
| tca aag cag atc gtc agc gac atg aac gat gag gaa aag gtt att gtc<br>Ser Lys Gln Ile Val Ser Asp Met Asn Asp Glu Glu Lys Val Ile Val<br>660                 665                  670 | 2017 |
| ttt gaa cgt gga gat tta gtt ttt gtt ttc aat ttc cat ccc aag aaa<br>Phe Glu Arg Gly Asp Leu Val Phe Val Phe Asn Phe His Pro Lys Lys<br>     675                    680                   685 | 2065 |
| act tac gag ggc tac aaa gtg gga tgc gat ttg cct ggg aaa tac aga<br>Thr Tyr Glu Gly Tyr Lys Val Gly Cys Asp Leu Pro Gly Lys Tyr Arg<br>690                 695                  700 | 2113 |
| gta gcc ctg gac tct gat gct ctg gtc ttc ggt gga cat gga aga gtt<br>Val Ala Leu Asp Ser Asp Ala Leu Val Phe Gly Gly His Gly Arg Val<br>705                 710                  715               720 | 2161 |
| ggc cac gac gtg gat cac ttc acg tcg cct gaa ggg gtg cca ggg gtg<br>Gly His Asp Val Asp His Phe Thr Ser Pro Glu Gly Val Pro Gly Val<br>                725                  730                  735 | 2209 |
| ccc gaa acg aac ttc aac aac cgg ccg aac tcg ttc aaa gtc ctt tct<br>Pro Glu Thr Asn Phe Asn Asn Arg Pro Asn Ser Phe Lys Val Leu Ser<br>740                 745                  750 | 2257 |
| ccg ccc cgc acc tgt gtg gct tat tac cgt gta gac gaa gca ggg gct<br>Pro Pro Arg Thr Cys Val Ala Tyr Tyr Arg Val Asp Glu Ala Gly Ala<br>     755                    760                   765 | 2305 |
| gga cga cgt ctt cac gcg aaa gca gag aca gga aag acg tct cca gca<br>Gly Arg Arg Leu His Ala Lys Ala Glu Thr Gly Lys Thr Ser Pro Ala<br>770                 775                  780 | 2353 |
| gag agc atc gac gtc aaa gct tcc aga gct agt agc aaa gaa gac aag<br>Glu Ser Ile Asp Val Lys Ala Ser Arg Ala Ser Ser Lys Glu Asp Lys<br>785                 790                  795               800 | 2401 |
| gag gca acg gct ggt ggc aag aag gga tgg aag ttt gcg cgg cag cca<br>Glu Ala Thr Ala Gly Gly Lys Lys Gly Trp Lys Phe Ala Arg Gln Pro<br>                805                  810                  815 | 2449 |
| tcc gat caa gat acc aaa tga<br>Ser Asp Gln Asp Thr Lys *<br>                820 | 2470 |

<210> SEQ ID NO 14
<211> LENGTH: 822
<212> TYPE: PRT
<213> ORGANISM: Zea mays

<400> SEQUENCE: 14

Leu Cys Leu Val Ser Pro Ser Ser Pro Thr Pro Leu Pro Pro Pro
1               5                   10                  15

-continued

```
Arg Arg Ser Arg Ser His Ala Asp Arg Ala Ala Pro Pro Gly Ile Ala
            20                  25                  30

Gly Gly Gly Asn Val Arg Leu Ser Val Leu Ser Val Gln Cys Lys Ala
            35                  40                  45

Arg Arg Ser Gly Val Arg Lys Val Lys Ser Lys Phe Ala Thr Ala Ala
 50                  55                  60

Thr Val Gln Glu Asp Lys Thr Met Ala Thr Ala Lys Gly Asp Val Asp
 65                  70                  75                  80

His Leu Pro Ile Tyr Asp Leu Asp Pro Lys Leu Glu Ile Phe Lys Asp
                85                  90                  95

His Phe Arg Tyr Arg Met Lys Arg Phe Leu Glu Gln Lys Gly Ser Ile
                100                 105                 110

Glu Glu Asn Glu Gly Ser Leu Glu Ser Phe Ser Lys Gly Tyr Leu Lys
            115                 120                 125

Phe Gly Ile Asn Thr Asn Glu Asp Gly Thr Val Tyr Arg Glu Trp Ala
            130                 135                 140

Pro Ala Ala Gln Glu Ala Glu Leu Ile Gly Asp Phe Asn Asp Trp Asn
145                 150                 155                 160

Gly Ala Asn His Lys Met Glu Lys Asp Lys Phe Gly Val Trp Ser Ile
                165                 170                 175

Lys Ile Asp His Val Lys Gly Lys Pro Ala Ile Pro His Asn Ser Lys
                180                 185                 190

Val Lys Phe Arg Phe Leu His Gly Gly Val Trp Val Asp Arg Ile Pro
            195                 200                 205

Ala Leu Ile Arg Tyr Ala Thr Val Asp Ala Ser Lys Phe Gly Ala Pro
            210                 215                 220

Tyr Asp Gly Val His Trp Asp Pro Pro Ala Ser Glu Arg Tyr Thr Phe
225                 230                 235                 240

Lys His Pro Arg Pro Ser Lys Pro Ala Ala Pro Arg Ile Tyr Glu Ala
                245                 250                 255

His Val Gly Met Ser Gly Glu Lys Pro Ala Val Ser Thr Tyr Arg Glu
                260                 265                 270

Phe Ala Asp Asn Val Leu Pro Arg Ile Arg Ala Asn Asn Tyr Asn Thr
            275                 280                 285

Val Gln Leu Met Ala Val Met Glu His Ser Tyr Tyr Ala Ser Phe Gly
            290                 295                 300

Tyr His Val Thr Asn Phe Phe Ala Val Ser Ser Arg Ser Gly Thr Pro
305                 310                 315                 320

Glu Asp Leu Lys Tyr Leu Val Asp Lys Ala His Ser Leu Gly Leu Arg
                325                 330                 335

Val Leu Met Asp Val Val His Ser His Ala Ser Asn Asn Val Thr Asp
                340                 345                 350

Gly Leu Asn Gly Tyr Asp Val Gly Gln Ser Thr Gln Glu Ser Tyr Phe
            355                 360                 365

His Ala Gly Asp Arg Gly Tyr His Lys Leu Trp Asp Ser Arg Leu Phe
            370                 375                 380

Asn Tyr Ala Asn Trp Glu Val Leu Arg Phe Leu Leu Ser Asn Leu Arg
385                 390                 395                 400

Tyr Trp Leu Asp Glu Phe Met Phe Asp Gly Phe Arg Phe Asp Gly Val
                405                 410                 415

Thr Ser Met Leu Tyr His His Gly Ile Asn Val Gly Phe Thr Gly
                420                 425                 430

Asn Tyr Gln Glu Tyr Phe Ser Leu Asp Thr Ala Val Asp Ala Val Val
```

```
                   435                 440                 445
Tyr Met Met Leu Ala Asn His Leu Met His Lys Leu Leu Pro Glu Ala
            450                 455                 460

Thr Val Val Ala Glu Asp Val Ser Gly Met Pro Val Leu Cys Arg Pro
465                 470                 475                 480

Val Asp Glu Gly Gly Val Gly Phe Asp Tyr Arg Leu Ala Met Ala Ile
                    485                 490                 495

Pro Asp Arg Trp Ile Asp Tyr Leu Lys Asn Lys Asp Asp Ser Glu Trp
                500                 505                 510

Ser Met Gly Glu Ile Ala His Thr Leu Thr Asn Arg Arg Tyr Thr Glu
            515                 520                 525

Lys Cys Ile Ala Tyr Ala Glu Ser His Asp Gln Ser Ile Val Gly Asp
530                 535                 540

Lys Thr Ile Ala Phe Leu Leu Met Asp Lys Glu Met Tyr Thr Gly Met
545                 550                 555                 560

Ser Asp Leu Gln Pro Ala Ser Pro Thr Ile Asp Arg Gly Ile Ala Leu
                565                 570                 575

Gln Lys Met Ile His Phe Ile Thr Met Ala Leu Gly Gly Asp Gly Tyr
                580                 585                 590

Leu Asn Phe Met Gly Asn Glu Phe Gly His Pro Glu Trp Ile Asp Phe
            595                 600                 605

Pro Arg Glu Gly Asn Asn Trp Ser Tyr Asp Lys Cys Arg Arg Gln Trp
610                 615                 620

Ser Leu Val Asp Thr Asp His Leu Arg Tyr Lys Tyr Met Asn Ala Phe
625                 630                 635                 640

Asp Gln Ala Met Asn Ala Leu Asp Glu Arg Phe Ser Phe Leu Ser Ser
                645                 650                 655

Ser Lys Gln Ile Val Ser Asp Met Asn Asp Glu Glu Lys Val Ile Val
                660                 665                 670

Phe Glu Arg Gly Asp Leu Val Phe Val Phe Asn Phe His Pro Lys Lys
            675                 680                 685

Thr Tyr Glu Gly Tyr Lys Val Gly Cys Asp Leu Pro Gly Lys Tyr Arg
690                 695                 700

Val Ala Leu Asp Ser Asp Ala Leu Val Phe Gly Gly His Gly Arg Val
705                 710                 715                 720

Gly His Asp Val Asp His Phe Thr Ser Pro Glu Gly Val Pro Gly Val
                725                 730                 735

Pro Glu Thr Asn Phe Asn Asn Arg Pro Asn Ser Phe Lys Val Leu Ser
                740                 745                 750

Pro Pro Arg Thr Cys Val Ala Tyr Tyr Arg Val Asp Glu Ala Gly Ala
            755                 760                 765

Gly Arg Arg Leu His Ala Lys Ala Glu Thr Gly Lys Thr Ser Pro Ala
770                 775                 780

Glu Ser Ile Asp Val Lys Ala Ser Arg Ala Ser Ser Lys Glu Asp Lys
785                 790                 795                 800

Glu Ala Thr Ala Gly Gly Lys Lys Gly Trp Lys Phe Ala Arg Gln Pro
                805                 810                 815

Ser Asp Gln Asp Thr Lys
            820

<210> SEQ ID NO 15
<211> LENGTH: 2700
<212> TYPE: DNA
<213> ORGANISM: Zea mays
```

-continued

```
<220> FEATURE:
<221> NAME/KEY: misc_feature
<222> LOCATION: (0)...(0)
<223> OTHER INFORMATION: Su1 isoamylase -- Genbank Accession No.
      AF030882
<221> NAME/KEY: CDS
<222> LOCATION: (88)...(2457)

<400> SEQUENCE: 15
cgtctcgtca cacactccac tcgaacgcac tacttgatcg gccaaagcca aacgaactgg      60
gctccctccc ctccacttcc tctcccc atg gcg cag cag ctc ccc tgc gtc tcg    114
                                Met Ala Gln Gln Leu Pro Cys Val Ser
                                  1               5 tcg ccg cgc ccg ctg ctc gcc gtg ccc gcg ggc cgg tgg cgc gcc ggc      162
Ser Pro Arg Pro Leu Leu Ala Val Pro Ala Gly Arg Trp Arg Ala Gly
 10              15                  20                  25 gtg cgg ggc cgg ccc aat gtg gcg gga ctg ggg cgg ggg cgg ctg tct      210
Val Arg Gly Arg Pro Asn Val Ala Gly Leu Gly Arg Gly Arg Leu Ser
                 30                  35                  40 ctc cac gcc gcc gcc gcg cgg ccc gtg gcc gag gcg gtg cag gcg gag      258
Leu His Ala Ala Ala Ala Arg Pro Val Ala Glu Ala Val Gln Ala Glu
             45                  50                  55 gag gac gac gac gac gac gac gag gag gtg gcc gag gag agg ttc gcg      306
Glu Asp Asp Asp Asp Asp Asp Glu Glu Val Ala Glu Glu Arg Phe Ala
         60                  65                  70 ctg ggc ggc gcg tgc cgg gtg ctc gcg gga atg ccc gcg ccg ctc ggc      354
Leu Gly Gly Ala Cys Arg Val Leu Ala Gly Met Pro Ala Pro Leu Gly
 75                  80                  85 gcc acc gcg ctc cgc ggc ggt gtc aac ttc gcc gtc tac tcc agc ggt      402
Ala Thr Ala Leu Arg Gly Gly Val Asn Phe Ala Val Tyr Ser Ser Gly
 90                  95                 100                 105 gcc tcc gcc gcg tcg ctg tgc ctc ttc gct ccc ggc gac ctc aag gcg      450
Ala Ser Ala Ala Ser Leu Cys Leu Phe Ala Pro Gly Asp Leu Lys Ala
                110                 115                 120 gat agg gtg acc gag gag gtg ccc ctc gat ccc ctg ctc aac cga acg      498
Asp Arg Val Thr Glu Glu Val Pro Leu Asp Pro Leu Leu Asn Arg Thr
            125                 130                 135 gga aac gtg tgg cac gtg ttc atc cac ggg gac cag ctg cac ggc atg      546
Gly Asn Val Trp His Val Phe Ile His Gly Asp Gln Leu His Gly Met
        140                 145                 150 ctc tac gga tac agg ttc gat ggc gtg ttc gcc cct gag cgc gga cag      594
Leu Tyr Gly Tyr Arg Phe Asp Gly Val Phe Ala Pro Glu Arg Gly Gln
    155                 160                 165 tac tac gat gtg tcc aac gtt gtg gtg gat cca tac gct aag gca gtg      642
Tyr Tyr Asp Val Ser Asn Val Val Val Asp Pro Tyr Ala Lys Ala Val
170                 175                 180                 185 gta agc cga ggt gaa tat ggt gtg cct gcg cct ggt ggt agt tgt tgg      690
Val Ser Arg Gly Glu Tyr Gly Val Pro Ala Pro Gly Gly Ser Cys Trp
                190                 195                 200 cct caa atg gct ggt atg atc cct ctt ccc tat aat aag ttt gat tgg      738
Pro Gln Met Ala Gly Met Ile Pro Leu Pro Tyr Asn Lys Phe Asp Trp
            205                 210                 215 caa ggt gac cta ccc ctt ggg tac cat cag aag gac ctt gtc ata tat      786
Gln Gly Asp Leu Pro Leu Gly Tyr His Gln Lys Asp Leu Val Ile Tyr
        220                 225                 230 gaa atg cat ttg cgt gga ttc aca aag cac aac tca agc aag aca aaa      834
Glu Met His Leu Arg Gly Phe Thr Lys His Asn Ser Ser Lys Thr Lys
    235                 240                 245 cac cca gga act tac att ggt gct gtg tca aag ctt gac cat cta aag      882
His Pro Gly Thr Tyr Ile Gly Ala Val Ser Lys Leu Asp His Leu Lys
250                 255                 260                 265
```

```
gaa ctt gga gtg aac tgt ata gag cta atg ccc tgc cat gag ttc aat     930
Glu Leu Gly Val Asn Cys Ile Glu Leu Met Pro Cys His Glu Phe Asn
            270                 275                 280 gag cta gag tac ttc agc tcc tct tcg aag atg aac ttc tgg gga tat     978
Glu Leu Glu Tyr Phe Ser Ser Ser Ser Lys Met Asn Phe Trp Gly Tyr
                285                 290                 295 tcc aca ata aat ttt ttc tca cca atg gca aga tat tct tca agt ggc    1026
Ser Thr Ile Asn Phe Phe Ser Pro Met Ala Arg Tyr Ser Ser Ser Gly
            300                 305                 310 ata aga gac tct gga tgt ggt gcc ata aat gaa ttt aaa gct ttt gta    1074
Ile Arg Asp Ser Gly Cys Gly Ala Ile Asn Glu Phe Lys Ala Phe Val
    315                 320                 325 agg gag gcc cac aaa cgg gga att gag gtg atc atg gat gtt gtc ttc    1122
Arg Glu Ala His Lys Arg Gly Ile Glu Val Ile Met Asp Val Val Phe
330                 335                 340                 345 aat cat aca gct gaa ggt aat gag aaa ggc cca ata tta tcc ttt agg    1170
Asn His Thr Ala Glu Gly Asn Glu Lys Gly Pro Ile Leu Ser Phe Arg
                350                 355                 360 ggg ata gat aat agt aca tac tac atg ctt gca cct aag gga gag ttt    1218
Gly Ile Asp Asn Ser Thr Tyr Tyr Met Leu Ala Pro Lys Gly Glu Phe
            365                 370                 375 tat aat tat tct ggt tgt gga aat acc ttc aat tgt aat cat cct gta    1266
Tyr Asn Tyr Ser Gly Cys Gly Asn Thr Phe Asn Cys Asn His Pro Val
        380                 385                 390 gtc cgt gaa ttt ata gtg gat tgc ttg aga tac tgg gta aca gaa atg    1314
Val Arg Glu Phe Ile Val Asp Cys Leu Arg Tyr Trp Val Thr Glu Met
    395                 400                 405 cat gtt gat ggt ttt cgt ttt gac ctt gca tct ata ctg acc aga gga    1362
His Val Asp Gly Phe Arg Phe Asp Leu Ala Ser Ile Leu Thr Arg Gly
410                 415                 420                 425 tgc agt cta tgg gat cca gtt aat gtg tat gga agt cca atg gaa ggt    1410
Cys Ser Leu Trp Asp Pro Val Asn Val Tyr Gly Ser Pro Met Glu Gly
                430                 435                 440 gac atg att acg aca ggg aca cct ctt gtt gcc cca cca ctt att gac    1458
Asp Met Ile Thr Thr Gly Thr Pro Leu Val Ala Pro Pro Leu Ile Asp
            445                 450                 455 atg att agc aat gac cca att ctt gga aat gtc aag ctc att gct gaa    1506
Met Ile Ser Asn Asp Pro Ile Leu Gly Asn Val Lys Leu Ile Ala Glu
        460                 465                 470 gca tgg gat gca gga ggt ctc tat caa gtt ggt cag ttt cct cac tgg    1554
Ala Trp Asp Ala Gly Gly Leu Tyr Gln Val Gly Gln Phe Pro His Trp
    475                 480                 485 aac gtt tgg tca gag tgg aat gga aag tat cgc gat acc gtg cgt cag    1602
Asn Val Trp Ser Glu Trp Asn Gly Lys Tyr Arg Asp Thr Val Arg Gln
490                 495                 500                 505 ttc atc aaa ggc aca gat gga ttt gct ggt gct ttt gct gaa tgc cta    1650
Phe Ile Lys Gly Thr Asp Gly Phe Ala Gly Ala Phe Ala Glu Cys Leu
                510                 515                 520 tgt gga agt cca cag tta tac cag gca ggg ggg agg aag cct tgg cac    1698
Cys Gly Ser Pro Gln Leu Tyr Gln Ala Gly Gly Arg Lys Pro Trp His
            525                 530                 535 agt atc aac ttt gta tgt gca cac gat gga ttt aca ctg gct gat ttg    1746
Ser Ile Asn Phe Val Cys Ala His Asp Gly Phe Thr Leu Ala Asp Leu
        540                 545                 550 gtc aca tac aat agc aag tac aac ttg tca aat ggt gag gac aac aga    1794
Val Thr Tyr Asn Ser Lys Tyr Asn Leu Ser Asn Gly Glu Asp Asn Arg
    555                 560                 565 gat ggg gaa aat cat aat ctt agc tgg aat tgt ggg gag gaa gga gaa    1842
Asp Gly Glu Asn His Asn Leu Ser Trp Asn Cys Gly Glu Glu Gly Glu
```

-continued

```
ttt gca agt ctg tca gtc cga aga tta agg aag agg caa atg cgc aat    1890
Phe Ala Ser Leu Ser Val Arg Arg Leu Arg Lys Arg Gln Met Arg Asn
                590                 595                 600 ttc ttt gtt tgt ctt atg gtt tct cag gga gtt cca atg ttc tac atg    1938
Phe Phe Val Cys Leu Met Val Ser Gln Gly Val Pro Met Phe Tyr Met
            605                 610                 615 ggc gat gaa tat ggt cac aca aag gga ggg aac aac aat acg tac tgc    1986
Gly Asp Glu Tyr Gly His Thr Lys Gly Gly Asn Asn Asn Thr Tyr Cys
        620                 625                 630 cat gac cat tat gtc aac tat ttc cgt tgg gat aag aag gaa gaa caa    2034
His Asp His Tyr Val Asn Tyr Phe Arg Trp Asp Lys Lys Glu Glu Gln
    635                 640                 645 tcc tct gat ttg tac aga ttc tgc cgt ctc atg acc aaa ttc cgc aag    2082
Ser Ser Asp Leu Tyr Arg Phe Cys Arg Leu Met Thr Lys Phe Arg Lys
650                 655                 660                 665 gaa tgt gaa tct ctt ggc ctt gag gac ttc ccg act tca gaa cgg ttg    2130
Glu Cys Glu Ser Leu Gly Leu Glu Asp Phe Pro Thr Ser Glu Arg Leu
                670                 675                 680 aaa tgg cac ggt cat cag ccc ggg aag cct gac tgg tca gag gca agc    2178
Lys Trp His Gly His Gln Pro Gly Lys Pro Asp Trp Ser Glu Ala Ser
            685                 690                 695 cga ttc gtt gcc ttc acc atg aag gac gaa acc aaa ggc gag atc tac    2226
Arg Phe Val Ala Phe Thr Met Lys Asp Glu Thr Lys Gly Glu Ile Tyr
        700                 705                 710 gtg gcc ttc aac acc agt cac ctt ccg gtg gtt gtc ggg ctt cca gag    2274
Val Ala Phe Asn Thr Ser His Leu Pro Val Val Val Gly Leu Pro Glu
    715                 720                 725 cgc tct ggg ttc cga tgg gag ccg gtg gtg gac acc ggc aag gag gca    2322
Arg Ser Gly Phe Arg Trp Glu Pro Val Val Asp Thr Gly Lys Glu Ala
730                 735                 740                 745 cca tat gac ttc ctc acc gat ggc cta cca gat cgt gct gtc acc gtc    2370
Pro Tyr Asp Phe Leu Thr Asp Gly Leu Pro Asp Arg Ala Val Thr Val
                750                 755                 760 tac cag ttc tct cat ttc ctc aac tcc aat ctc tat cct atg ctc agc    2418
Tyr Gln Phe Ser His Phe Leu Asn Ser Asn Leu Tyr Pro Met Leu Ser
            765                 770                 775 tac tcc tcc atc atc ctt gta ttg cgc cct gat gtc tga aagaagcgga    2467
Tyr Ser Ser Ile Ile Leu Val Leu Arg Pro Asp Val *
        780                 785 tacaatagag tatactgtag cggttgttct ctaggctgta gcatgcagtg gaaactggaa   2527
aatgttgggg ttgctctgtt gtcggtagtt tacatgcgca tgtcggtatg tgtagctaaa   2587
gctggtggat ctcagttctc agatcggact cgagccgggg aaaaccattg cccggttggc   2647
tggttctctg aagttgtgtt tggtgtaaag aaatggtggt ccatcatcta ctc          2700

<210> SEQ ID NO 16
<211> LENGTH: 789
<212> TYPE: PRT
<213> ORGANISM: Zea mays

<400> SEQUENCE: 16

Met Ala Gln Gln Leu Pro Cys Val Ser Ser Pro Arg Pro Leu Leu Ala
 1               5                  10                  15

Val Pro Ala Gly Arg Trp Arg Ala Gly Val Arg Gly Arg Pro Asn Val
            20                  25                  30

Ala Gly Leu Gly Arg Gly Arg Leu Ser Leu His Ala Ala Ala Ala Arg
        35                  40                  45
```

-continued

```
Pro Val Ala Glu Ala Val Gln Ala Glu Asp Asp Asp Asp Asp
 50                  55                  60
Glu Glu Val Ala Glu Glu Arg Phe Ala Leu Gly Gly Ala Cys Arg Val
 65                  70                  75                  80
Leu Ala Gly Met Pro Ala Pro Leu Gly Ala Thr Ala Leu Arg Gly Gly
                 85                  90                  95
Val Asn Phe Ala Val Tyr Ser Ser Gly Ala Ser Ala Ser Leu Cys
            100                 105                 110
Leu Phe Ala Pro Gly Asp Leu Lys Ala Asp Arg Val Thr Glu Glu Val
            115                 120                 125
Pro Leu Asp Pro Leu Leu Asn Arg Thr Gly Asn Val Trp His Val Phe
        130                 135                 140
Ile His Gly Asp Gln Leu His Gly Met Leu Tyr Gly Tyr Arg Phe Asp
145                 150                 155                 160
Gly Val Phe Ala Pro Glu Arg Gly Gln Tyr Tyr Asp Val Ser Asn Val
                165                 170                 175
Val Val Asp Pro Tyr Ala Lys Ala Val Val Ser Arg Gly Glu Tyr Gly
            180                 185                 190
Val Pro Ala Pro Gly Gly Ser Cys Trp Pro Gln Met Ala Gly Met Ile
        195                 200                 205
Pro Leu Pro Tyr Asn Lys Phe Asp Trp Gln Gly Asp Leu Pro Leu Gly
        210                 215                 220
Tyr His Gln Lys Asp Leu Val Ile Tyr Glu Met His Leu Arg Gly Phe
225                 230                 235                 240
Thr Lys His Asn Ser Ser Lys Thr Lys His Pro Gly Thr Tyr Ile Gly
                245                 250                 255
Ala Val Ser Lys Leu Asp His Leu Lys Glu Leu Gly Val Asn Cys Ile
            260                 265                 270
Glu Leu Met Pro Cys His Glu Phe Asn Glu Leu Glu Tyr Phe Ser Ser
        275                 280                 285
Ser Ser Lys Met Asn Phe Trp Gly Tyr Ser Thr Ile Asn Phe Phe Ser
290                 295                 300
Pro Met Ala Arg Tyr Ser Ser Ser Gly Ile Arg Asp Ser Gly Cys Gly
305                 310                 315                 320
Ala Ile Asn Glu Phe Lys Ala Phe Val Arg Glu Ala His Lys Arg Gly
                325                 330                 335
Ile Glu Val Ile Met Asp Val Val Phe Asn His Thr Ala Glu Gly Asn
            340                 345                 350
Glu Lys Gly Pro Ile Leu Ser Phe Arg Gly Ile Asp Asn Ser Thr Tyr
        355                 360                 365
Tyr Met Leu Ala Pro Lys Gly Glu Phe Tyr Asn Tyr Ser Gly Cys Gly
        370                 375                 380
Asn Thr Phe Asn Cys Asn His Pro Val Val Arg Glu Phe Ile Val Asp
385                 390                 395                 400
Cys Leu Arg Tyr Trp Val Thr Glu Met His Val Asp Gly Phe Arg Phe
                405                 410                 415
Asp Leu Ala Ser Ile Leu Thr Arg Gly Cys Ser Leu Trp Asp Pro Val
            420                 425                 430
Asn Val Tyr Gly Ser Pro Met Glu Gly Asp Met Ile Thr Gly Thr
            435                 440                 445
Pro Leu Val Ala Pro Pro Leu Ile Asp Met Ile Ser Asn Asp Pro Ile
450                 455                 460
Leu Gly Asn Val Lys Leu Ile Ala Glu Ala Trp Asp Ala Gly Gly Leu
```

```
465                 470                 475                 480
Tyr Gln Val Gly Gln Phe Pro His Trp Asn Val Trp Ser Glu Trp Asn
                485                 490                 495
Gly Lys Tyr Arg Asp Thr Val Arg Gln Phe Ile Lys Gly Thr Asp Gly
            500                 505                 510
Phe Ala Gly Ala Phe Ala Glu Cys Leu Cys Gly Ser Pro Gln Leu Tyr
            515                 520                 525
Gln Ala Gly Gly Arg Lys Pro Trp His Ser Ile Asn Phe Val Cys Ala
        530                 535                 540
His Asp Gly Phe Thr Leu Ala Asp Leu Val Thr Tyr Asn Ser Lys Tyr
545                 550                 555                 560
Asn Leu Ser Asn Gly Glu Asp Asn Arg Asp Gly Glu Asn His Asn Leu
                565                 570                 575
Ser Trp Asn Cys Gly Glu Glu Gly Glu Phe Ala Ser Leu Ser Val Arg
            580                 585                 590
Arg Leu Arg Lys Arg Gln Met Arg Asn Phe Phe Val Cys Leu Met Val
        595                 600                 605
Ser Gln Gly Val Pro Met Phe Tyr Met Gly Asp Glu Tyr Gly His Thr
    610                 615                 620
Lys Gly Gly Asn Asn Thr Tyr Cys His Asp His Tyr Val Asn Tyr
625                 630                 635                 640
Phe Arg Trp Asp Lys Lys Glu Glu Gln Ser Ser Asp Leu Tyr Arg Phe
            645                 650                 655
Cys Arg Leu Met Thr Lys Phe Arg Lys Glu Cys Glu Ser Leu Gly Leu
            660                 665                 670
Glu Asp Phe Pro Thr Ser Glu Arg Leu Lys Trp His Gly His Gln Pro
        675                 680                 685
Gly Lys Pro Asp Trp Ser Glu Ala Ser Arg Phe Val Ala Phe Thr Met
        690                 695                 700
Lys Asp Glu Thr Lys Gly Glu Ile Tyr Val Ala Phe Asn Thr Ser His
705                 710                 715                 720
Leu Pro Val Val Val Gly Leu Pro Glu Arg Ser Gly Phe Arg Trp Glu
                725                 730                 735
Pro Val Val Asp Thr Gly Lys Glu Ala Pro Tyr Asp Phe Leu Thr Asp
            740                 745                 750
Gly Leu Pro Asp Arg Ala Val Thr Val Tyr Gln Phe Ser His Phe Leu
            755                 760                 765
Asn Ser Asn Leu Tyr Pro Met Leu Ser Tyr Ser Ser Ile Ile Leu Val
    770                 775                 780
Leu Arg Pro Asp Val
785
```